US010590498B2

(12) United States Patent
Valdez et al.

(10) Patent No.: US 10,590,498 B2
(45) Date of Patent: Mar. 17, 2020

(54) COMPOUNDS FOR REACTIVATION OF ACETYLCHOLINESTERASE AND RELATED COMPOSITIONS METHODS AND SYSTEMS

(71) Applicant: LAWRENCE LIVERMORE NATIONAL SECURITY, LLC, Livermore, CA (US)

(72) Inventors: Carlos A. Valdez, San Ramon, CA (US); Nicholas A. Be, Oakland, CA (US); Brian Bennion, Tracy, CA (US); Tim Carpenter, Livermore, CA (US); Heather Ann Enright, Livermore, CA (US); Felice Lightstone, Fremont, CA (US); Mike Malfatti, San Ramon, CA (US); Margaret Windy McNerney, Pleasanton, CA (US); Tuan H. Nguyen, Livermore, CA (US)

(73) Assignee: Lawrence Livermore National Security, LLC, Livermore, CA (US)

( * ) Notice: Subject to any disclaimer, the term of this patent is extended or adjusted under 35 U.S.C. 154(b) by 139 days.

(21) Appl. No.: 15/595,400

(22) Filed: May 15, 2017

(65) Prior Publication Data

US 2017/0335415 A1 Nov. 23, 2017

Related U.S. Application Data

(60) Provisional application No. 62/337,734, filed on May 17, 2016.

(51) Int. Cl.

*A61K 31/15* (2006.01)
*C07C 251/58* (2006.01)
(Continued)

(52) U.S. Cl.

CPC ...... *C12Y 301/01007* (2013.01); *A61K 31/15* (2013.01); *A61K 31/4192* (2013.01);
(Continued)

(58) Field of Classification Search

CPC ............ C12Y 301/01007; A61K 31/15; A61K 31/4192; A61K 45/06; C07C 251/58
(Continued)

(56) References Cited

U.S. PATENT DOCUMENTS

| | | | | |
|---|---|---|---|---|
| 2013/0035351 A1* | 2/2013 | Mchardy | C07D 219/12 | 514/274 |
| 2014/0024690 A1* | 1/2014 | Abramite | C07D 261/08 | 514/380 |

(Continued)

FOREIGN PATENT DOCUMENTS

WO WO-2014127315 A1 * 8/2014 ........... C07D 221/22

OTHER PUBLICATIONS

Radic; J. Biol. Chem. 2012, 11798-11809. (Year: 2012).*
(Continued)

*Primary Examiner* — Daniel R Carcanague
(74) *Attorney, Agent, or Firm* — Steinfl + Bruno

(57) ABSTRACT

Described herein are oxime compounds capable of inactivating a nerve agent, blood brain barrier (BBB)-penetration, and/or reactivation of nerve agent-inhibited acetylcholinesterase (AChE) and related methods, systems and compositions for inactivation of one or more nerve agents, therapeutic and/or prophylactic treatment of an individual, and/or decomposition of nerve agent for decontamination.

30 Claims, 19 Drawing Sheets

(51) Int. Cl.
*A61K 31/4192* (2006.01)
*A61K 45/06* (2006.01)
*C07D 241/04* (2006.01)
*C07D 213/20* (2006.01)
*A61K 31/221* (2006.01)

(52) U.S. Cl.
CPC ............ *A61K 45/06* (2013.01); *C07C 251/58* (2013.01); *A61K 31/221* (2013.01); *C07D 213/20* (2013.01); *C07D 241/04* (2013.01)

(58) Field of Classification Search
USPC .......................................................... 548/255
See application file for complete search history.

(56) References Cited

U.S. PATENT DOCUMENTS

2014/0051712 A1* 2/2014 Cashman ............. C07D 233/24 514/256
2019/0152920 A1 5/2019 Valdez et al.

OTHER PUBLICATIONS

Malfatti; Chemico-Biological Interactions 277 (2017) 159-167. (Year: 2017).*
McHardy; Bioorganic and Medicinal Chemistry Letters 2014, 24, 1711-1714. (Year: 2014).*
Somin; Khimiko-Farmatsevticheskii Zhurnal, vol. 2, Issue 8, pp. 39-44, 1968, Scifinder Abstract. (Year: 1968).*
Mukaiyama; Chem Lett 1992, 181-184. (Year: 1992).*
Chemical Abstracts STN Registry Database, record for RN 22078-33-7, entered STN Nov. 16, 1984. (Year: 1984).*
Chemical Abstracts STN Registry Database, record for RN 364615-27-0, entered STN Oct. 25, 2001. (Year: 2001).*
Kalisiak; J. Med. Chem. 2012, 55, 465-474. (Year: 2012).*
Chemical Abstracts STN Registry Database, record for RN 1883191-36-3, entered STN Mar. 10, 2016. (Year: 2016).*
Chemical Abstracts STN Registry Database, record for 1843492-56-7, Entered into Database on Jan. 10, 2016. (Year: 2016).*
Chemical Abstracts STN Registry Database, record for 1883040-24-1, Entered into Database on Mar. 10, 2016. (Year: 2016).*
Chemical Abstracts STN Registry Database, record for 1883127-28-3, Entered into Database on Mar. 10, 2016. (Year: 2016).*
Sharma; Mini-Reviews in Medicinal Chemistry, 2015, 15, 58-72. (Year: 2015).*
Ajami, D. et al., "Chemical Approaches for Detection and Destruction of Nerve Agents.", Org. Biomol. Chem., vol. 11, No. 4, pp. 3936-3942, (2013), 8 pages.
Bennion, B.J. et al., "Predicting a Drug's Membrane Permeability: A Computational Model Validated With in Vitro Permeability Assay Data.", The Journal of Physical Chemistry B, 121(20), pp. 5228-5237, (2017).
Carpenter, T.S. et al., "A Method to Predict Blood-Brain Barrier Permeability of Drug-Like Compounds Using Molecular Dynamics Simulations.", Biophysical Journal, vol. 107, Issue 3, pp. 630-641, (2014).
Chen, X. et al., "A Novel Design of Artificial Membrane for Improving the PAMPA Model.", Pharmaceutical Research, vol. 25, Nol. 7, pp. 1511-1520, (2008).
Dolgin, E., "Syrian Gas Attack Reinforces Need for Better Anti-Sarin Drugs.", Nature Medicine, vol. 19, No. 10, pp. 1194-1195, (2013).
Ekström, F. et al., "Structure of HI-6●Sarin-Acetylcholinesterase Determined by X-Ray Crystallography and Molecular Dynamics Simulation: Reactivator Mechanism and Design.", PLOS ONE, vol. 4, Issue 6, e5957, (2009), 19 pages.
Ellman, GL. Et al., "A New and Rapid Colorimetric Determination of Acetylcholinesterase Activity.", Biochemical Pharmacology, vol. 7, pp. 88-95, (1961), 9 pages.
Feng, B. et al., "In Vitro P-glycoprotein Assays to Predict the in Vivo Interactions of P-glycoprotein with Drugs in the Central Nervous System.", Drug Metabolism and Disposition, vol. 36, No. 2, pp. 268-275, (2008).
Haines, D.D. et al., "Acute and Long-Term Impact of Chemical Weapons: Lessons from the Iran-Iraq War.", Forensic Science Review, vol. 26, No. 2, pp. 97-114, (2014), 19 pages.
Okamura, T. et al., "The Tokyo Subway Sarin Attack—Lessons Learned.", Toxicology and Applied Pharmacology, vol. 207, pp. S471-S476, (2005), 6 pages.
Okamura, T. et al., "Report on 640 Victims of the Tokyo Subway Sarin Attack.", Ann. Emerg. Med. 28, pp. 129-135, (1996).
Singh, B. et al., "Decontamination of Chemical Warfare Agents.", Defense Science Journal, vol. 60, No. 4, pp. 428-441, (2010).
Tu, A.T. et al., "Aum Shinrikyo's Chemical and Biological Weapons: More Than Sarin.", Forensic Science Review, vol. 26, No. 2, pp. 115-120, (2014).
Yang, Y-C. et al., "Decontamination of Chemical Warfare Agents.", Chemical Reviews, vol. 92, No. 8, pp. 1729-1743, (1992).
Zhang, X. et al., "Molecular Dynamics Simulations of Ligand Recognition Upon Binding Antithrombin: A MM/GBSA Approach.", Bioinformatics and Biomedical Engineering, 9044, pp. 584-593, (2015).
"Guides for the Use of Environmental Marketing Claims", retrieved on Dec. 4, 2017 from https://www.ftc.gov/sites/default/files/attachments/press-releases/ftc-issues-revised-green-guide/greenguides.pdf), pp. 1-36.
Ajami, D., et al., "Chemical approaches for detection and destruction of nerve agents," Org. Biomol. Chem. 2013, 11, 3936-3942.
Bennion, et al., "Predicting a Drug's Membrane Permeability: A Computational Model Validated With in Vitro Permeability Assay Data," The Journal of Physical Chemistry B 121(20): 5228-5237, 2017.
Carpenter, T.S., et al., "A Method to Predict Blood-Brain Barrier Permeability of Drug-Like Compounds Using Molecular Dynamics Simulations," Biophysical Journal, vol. 107, Issue 3, Aug. 5, 2014, pp. 630-641, ISSN 0006-3495.
Chen, X., et el., "A Novel Design of Artificial Membrane for Improving the PAMPA Model," Pharmaceutical Research, vol. 25, No. 7, Jul. 7, 2008, 10 pages.
Dolgin, E., "Syrian gas attack reinforces need for better anti-sarin drugs," Nat, Med. 19 (2013) 1194-1195.
Ekstrom, F., et al., "Structure of HI-6•Sarin-Acetylcholinesterase Determined by X-Ray Crystallography and Molecular Dynamics Simulation: Reactivator Mechanism and Design," PLoS ONE, 2009, 4(6): e5957. doi:10.1371/journal.pone.0005957.
Ellman, GL, et al., "A new and rapid colorimetric determination of acetylcholinesterase activity," Biochem Pharmacol, 1961, 7:88-95.
Haines, D.D., et al., "Acute and Long-Term Impact of Chemical Weapons: Lessons from the Iran-Iraq War," Forensic Sci. Rev. 26 (2014) 97-114.
Loscher, et al., "Blood-Brain Barrier Active Efflux Transporters: ATPBindino Cassette Gene Family," NeuroRx. Jan. 2005; 2(1): 86-98.
Okumura, T., et al., "Report on 640 victims of the Tokyo subway sarin attack," Ann. Emerg. Med. 28 (1996) 129-135.
Okumura, T., et al., "The Tokyo subway sarin attack—lessons learned," Toxicol. Appl. Pharmacol. 207 (2005) 471-476.
Singh, B., et al., "Decontamination of chemical warfare agents" Def. Sci. J. 2010,60, 428-441.
Tu, A.T., "Aum Shinrikyo's Chemical and Biological Weapons: More Than Sarin," Forensic Sci. Rev. 26 (2014) 115-120.
Yang, Y-C., et al., "Decontamination of chemical warfare agents" Chem. Rev. 1992, 92, 1729-1743.
Zhang, X., et al., "Molecular Dynamics Simulations of Ligand Recognition Upon Binding Antithrombin: A MM/GBSA Approach Bioinformatics and Biomedical Engineering," 2015, 9044, 584-593.

* cited by examiner

Atropine

2-PAM

CV9-048
[RS-41A]

CV9-043
[RS-194B]

CV9-076

CV9-086

CV9-087

16

Protonation at the triazole ring DN3>DN1>DN2

17

R54 = a linear or branched, optionally additional one to six heteroatoms or one to three substituents containing, alkyl, alkenyl, alkynyl, aryl, arylalkyl or alkylaryl carbon atom or a heteroatom having equal to or less than 18 carbon atoms including methyl, ethyl, iso-propyl, n-butyl, s-butyl, i-butyl, and

17

18

Formula (IIIp)

Formula (IIIq)

Formula (III)

n11 = 0, 1, 2 and 3

5 n12 = 0, 1, 2, or 3

6

7a 7

8a 8

9a 9

10a 10

15a

15

COMPOUNDS FOR REACTIVATION OF ACETYLCHOLINESTERASE AND RELATED COMPOSITIONS METHODS AND SYSTEMS

CROSS-REFERENCE TO RELATED APPLICATIONS

This application claims priority to provisional application 62/337,734 entitled "Compounds for Reactivation of Acetylcholinesterase And Related Compositions Methods And Systems" filed on May 17, 2016 with the contents of which is incorporated herein by reference.

STATEMENT OF GOVERNMENT GRANT

The invention was made with Government support under Contract No. DE-AC52-07NA27344 between the U.S. Department of Energy and Lawrence Livermore National Security, LLC, for the operation of Lawrence Livermore National Security. The Government may have certain rights to the invention.

FIELD

The present disclosure relates to compositions and methods for inactivation of nerve agents and/or for reactivation of acetylcholinesterase.

BACKGROUND

Acetylcholinesterase (AChE) is an enzyme that catalyzes the breakdown of acetylcholine that functions as a neurotransmitter. AChE is the primary target of inhibition by organophosphorus-based compounds such as nerve agents and pesticides or other acetylcholinesterase inhibitors. Acetylcholinesterase inhibitors (AChEI) or anti-cholinesterase in particular operate to inhibit the acetylcholinesterase enzyme from breaking down acetylcholine, thereby increasing both the level and duration of action of the neurotransmitter acetylcholine.

Despite efforts made towards the neutralization and/or destruction of acetylcholinesterase inhibitors, however, the current standard of care for exposure to acetylcholinesterase inhibitors, in particular organophosphorus-based agents, has changed very little in the past decades.

Accordingly, effective inactivation of nerve agents and/or reactivation of the nerve agent-inhibited acetylcholinesterase (AChE) is still highly desirable and a challenging goal in the areas of chemical warfare agent (CWA) defeat and medical countermeasures against these toxic chemicals.

SUMMARY

Provided herein are oximes of general formula (I)

(I)

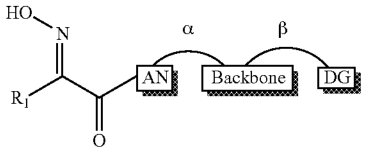

wherein

R1 is H, or $CH_3$;

"AN" is a nitrogen;

"Backbone" is formed by at least 1 carbon atom forming together with AN and/or DG an aromatic or an aliphatic cyclic moiety, α and β are independently one or more single, double or triple bonds covalently linking AN and DG with Backbone respectively, DG is a distal group formed by a moiety of formula (II)

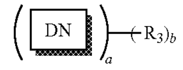

in which DN is a nitrogen,

R3 is a H or an substituted or unsubstituted linear or branched alkyl chain, aromatic or aliphatic cyclic group, a is an integer from 0 to 3 b is an integer from 0 to 2 and at least one of a and b is equal to or higher than 1.

and related compositions, methods and systems, in several embodiments are capable of reactivating inhibited acetylcholinesterase (AChE) and/or inactivating a nerve agent. In some embodiments, the oximes herein described are also capable of crossing the blood brain barrier (BBB) and/or to reach the peripheral nervous system (PNS).

According to a first aspect, a compound of Formula (III) is described,

Formula (III)

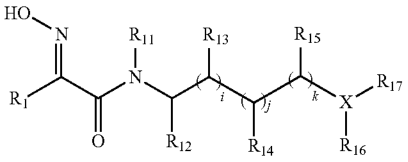

wherein

X is N or C—R10;

j and k are independently 0 or 1;

R1=H, or $CH_3$; and

R10, R11, R12, R13, R14, R15, R16 and R17 are independently H, a linear or branched, alkyl, alkenyl, alkynyl, aryl, arylalkyl or alkylaryl groups having equal to or less than 18 carbon atoms, wherein R11 and one of R12, R13, R14, R15, R16 and R17 or R12 and one of R13, R14, R15, R16 and R17 moieties are linked to form an aromatic or aliphatic cycle, wherein the alkyl, alkenyl, alkynyl, aryl, arylalkyl or alkylaryl groups can optionally independently include one to six heteroatoms and/or one to three substituents.

According to a second aspect, a compound of Formula (III) is described, in which X is N or C—R10;

j and k are independently 0 or 1;

R1=H, or $CH_3$; and

R10, R11, R12, R13, R14, R15, R16 and R17 are independently H, a linear or branched, alkyl, alkenyl, alkynyl, aryl, arylalkyl or alkylaryl groups having equal to or less than 18 carbon atoms, wherein the alkyl, alkenyl, alkynyl, aryl, arylalkyl or alkylaryl groups can optionally independently include one to six heteroatoms and/or one to three substituents, and wherein R14 and one of R15, R16 and R17, or R15 and one of R16 and R17 moieties are linked to form a backbone cyclic moiety.

According to a third aspect, a method to reactivate an inactivated acetylcholinesterase in an individual is described. The method comprises administering to the individual at least one oxime compound herein described for a time and under a condition to allow contact between the at least one oxime compound and the inactivated acetylcholinesterase in the individual. In the method, the at least one oxime compound is administered in an amount effective to allow contact between the at least one oxime compound and the inactivated acetylcholinesterase resulting in reactivation of the inactivated acetylcholinesterase.

According to a fourth aspect, a composition for reactivating an inactivated acetylcholinesterase is described. The composition comprises an effective amount of at least one oxime compound herein described and an acceptable vehicle, such as a buffer or a saline solution.

According to a fifth aspect, a method to inactivate a nerve agent in an individual is described. The method comprises administering to the individual an effective amount of at least one oxime compound herein described for a time and under condition to allow contact between the at least one oxime compound and the nerve agent in the individual thus resulting in inactivation of the nerve agent.

According to a sixth aspect, a composition for inactivating an nerve agent is described.

The composition comprises an effective amount of at least one oxime compound herein described and an acceptable vehicle, such as a buffer or saline solution.

According to a seventh aspect, a method of treating and/or preventing a condition in an individual is described. In the method, the condition is associated to exposure of the individual to a nerve agent. The method comprises administering to the individual at least one oxime compound herein described for a time and under condition to allow contact between the at least one oxime compound and AChE molecule in the nervous system of the individual or a portion thereof. In the method the at least one oximes is administered in an effective amount to treat and/or prevent the condition associated to the exposure of the individual to the nerve agent.

According to an eighth aspect, a method to prevent in an individual a condition associated to exposure of the individual to a nerve agent. The method comprises administering to the individual an effective amount of at least one oxime capable of inactivating one or more nerve agent. In the method, the administering is performed to allow the at least one oxime to contact the nervous system of the individual or a portion thereof and/or to contact the vascular system of the individual or a portion thereof, such as blood.

According to a ninth aspect, a method of decontaminating an environment from one or more nerve agent possibly present in the environment is described. The method comprises, contacting at least one oxime herein described with an environment, for a time to allow contacting and chemical reaction of the at least one oxime compound with one or more nerve agent possibly present in the environment, thus resulting in the inactivation of the nerve agent when present in the environment.

According to a tenth aspect, a composition of decontaminating an environment from one or more nerve agent possibly present in the environment is described. The composition comprises an effective amount of at least one oxime compound herein described and an acceptable vehicle.

The compounds, compositions, methods and systems herein described herein described allow in several embodiments to penetrate and cross the Blood Brain Barrier (BBB), allowing the compounds to reach the synapse in the brain The compounds, compositions, methods and systems herein described allow in several embodiments to protect an individual from damages by nerve agents not only in the Peripheral Nervous System (PNS), but also for the Central Nervous System (CNS).

The compounds, and compositions herein described are formulated in several embodiments for prophylactic administration to a subject suspected of potential exposure to a nerve agent.

The compounds, and compositions herein described are formulated in several embodiments for decontamination of a nerve agent in an environment.

The compounds, compositions, methods and systems herein described allow in several embodiments to prevent or mitigate medical complications associated with exposure of an individual to a nerve agent, including recurring complications occurring after survival of the initial exposure that are observed in chronic neurological disease.

The compounds, compositions, methods and systems herein described herein described can be used in connection with various applications wherein reactivation of an inactivated acetylcholinesterase is desired. For example, compounds, compositions, methods and systems herein described can be used to treat individuals that have been exposed to AChE-inhibiting organophosphate nerve agents via terror attack, occupational exposure, and attempted suicide. Additional exemplary applications include uses of the compounds herein described in several fields including basic biology research, applied biology, bio-engineering, bio-energy, medical research, therapeutics, and in additional fields identifiable by a skilled person upon reading of the present disclosure.

The details of one or more embodiments of the disclosure are set forth in the accompanying drawings and the description below. Other features, objects, and advantages will be apparent from the description and drawings, and from the claims.

BRIEF DESCRIPTION OF THE DRAWINGS

The accompanying drawings, which are incorporated into and constitute a part of this specification, illustrate one or more embodiments of the present disclosure and, together with the detailed description and the examples, serve to explain the principles and implementations of the disclosure.

DETAILED DESCRIPTION

Figure 1:
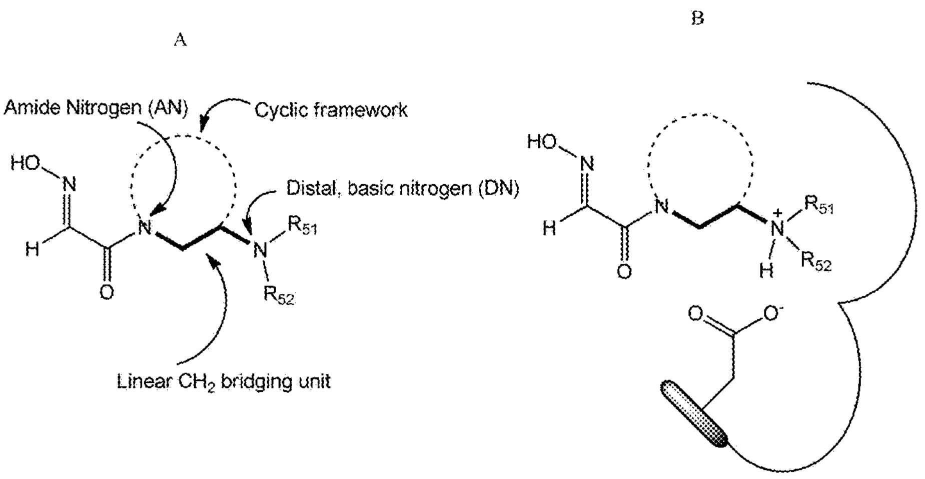
FIG. 1 shows a schematic representation of the structure of an exemplary oxime herein described and a related exemplary reaction with a target compound in accordance with an embodiment of the disclosure. In particular, FIG. 1 Panel A shows the structure of an oxime where the amide nitrogen (AN) and the distal basic nitrogen (DN) and a related bridging unit FIG. 1 Panel B shows a schematic illustration of possible interactions of the exemplary oxime illustrated in Panel A with a AChE's active site stemming from its possible states (charged and neutral).

Oximes, and related materials, compositions, methods, and systems are described.

The term "oxime", as used herein, refers an organic compound containing a carbon-nitrogen double bond in which the nitrogen also forms a single bond with an oxygen and the carbon additionally forms two single bonds, one of which with hydrogen atom and the other with carbon, or each single bond with carbon. In some cases oxime can be compounds or moieties with general formula (R71)(R72)C═N—O(R73); wherein R71 and R73 are independently selected from the group consisting of H, a linear or branched, alkyl, alkenyl, alkynyl, aryl, arylalkyl or alkylaryl carbon atom having equal to or less than 18 carbon atoms and optionally containing additional one to six heteroatoms or one to three substituents; R72 can be selected from the group consisting of a linear or branched, optionally additional one to six heteroatoms or one to three substituents containing, alkyl, alkenyl, alkynyl, aryl, arylalkyl or alkylaryl carbon atom having equal to or less than 18 carbon atoms. An oxime compound can be detected and/or characterized by any of the methods including but not limited to infrared spectroscopy, proton or carbon nuclear magnetic resonance spectroscopy, mass spectroscopy, UV-vis absorption spectroscopy and additional techniques identifiable by a skilled person.

The term "neutral oxime," as used herein, refers to an uncharged organic molecule containing a oxime moiety. The uncharged organic molecule may contain at least one neutral basic nitrogen, such as in a primary, secondary or a tertiary amino group or in a heteroaromatic ring such as imidazole or triazole, which could become protonated under physiological conditions or which may be present as a protonated salt and become a corresponding positively charged nitrogen. Alternatively or in addition, the uncharged organic molecule may contain at least one amide of a primary or a secondary amine.

In embodiments herein described, neutral oximes of the disclosure have a general formula (I)

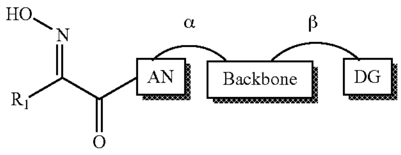

wherein

R1 is H, or $CH_3$;

"AN" is a nitrogen;

"Backbone is formed by at least 1 carbon atom forming together with AN and/or DG an aromatic or an aliphatic cyclic moiety, α and β are independently one or more single, double or triple bonds covalently linking AN and DG with Backbone respectively, DG is a distal group formed by a moiety of formula (II)

(II)

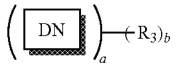

in which DN is a nitrogen,

R3 is a H or an substituted or unsubstituted linear or branched alkyl chain, aromatic or aliphatic cyclic group, a is an integer from 0 to 3, b is an integer from 0 to 2, and at least one of a and b is equal to or higher than 1.

Accordingly, the term "AN" as used herein in connection with oximes identifies the nitrogen of an amide moiety the carbon of which is directly covalently bonded to the carbon of an oxime moiety of a neutral oxime as will be understood by a skilled person. The term "DN" as used herein in connection with oximes identifies a nitrogen that is distal to the oxime moiety. The term "backbone atoms," as used herein, refers to carbon atoms of an oxime, constituting the chemical bond connection of the minimum number of intervening atoms between the carbon of an oxime moiety and a DN and/or an aromatic or aliphatic cyclic moiety.

In some embodiments, the backbone cyclic moiety comprises at least 2 carbon atoms. In some embodiments, the backbone cyclic moiety is an aliphatic cycle. In some embodiments, the backbone cyclic moiety is an aromatic cycle. In some embodiments, the backbone cyclic moiety is a heteroaromatic cycle.

In some embodiments, neutral oximes herein described comprise AN and DN within a backbone piperazine moiety.

In some embodiments, in neutral oximes herein described DN is linked to the backbone cyclic moiety comprising AN. In some of those embodiments, DN forms a part of a triazole moiety linked to the backbone cyclic moiety further comprising AN.

In embodiments herein described, the lipophilicity of an oxime compound of the disclosure can be quantified by a c log P value which refers to the logarithm of its partition coefficient between n-octanol and water $\log(c_{octanol}/c_{water})$ as is known by a person skilled in the art. High lipophilicity corresponds to a high c Log P value. Oximes of the present disclosure can be configured with a combination of moieties and/or substituents to have specific c log P values as will be understood by a skilled person upon reading of the present disclosure.

In some embodiments, oximes of the present disclosure can be configured with a combination of moieties and/or substituents to have specific c log P values in a range of 2.0 to 4.5.

In some embodiments, oximes of the present disclosure can be configured with a combination of moieties and/or substituents to have specific c log P values in a range of 0. to 3.0.

In some embodiments, oximes of the present disclosure can be configured with a combination of moieties and/or substituents to have specific c log P values in a range of in a range of 0 to 2.

In some embodiments, oximes of the present disclosure can be configured with a combination of moieties and/or substituents to have specific c log P values in a range of less than 0.

In embodiments herein described, the equilibrium between protonated and non-protonated forms of an oxime of the disclosure can be indicated with a pKa value with pKa being the acid dissociation constant (also known as acidity constant, or acid-ionization constant) a quantitative measure of the strength of an acid A in solution, defined by the equation $$K_a = \frac{[A^-][H_3O^+]}{[HA][H_2O]}$$

and with pKa being $$pK_a = -\log_{10} K_a$$

as will be understood by a skilled person.

Oximes of the present disclosure can be configured with a combination of moieties and/or substituents to have specific pKa values of the protonated form of the oximes herein described, as will be understood by a skilled person upon reading of the present disclosure. In some embodiments, the pKa values for protonated form of the oximes herein described can range between 7 and 11. In some embodiments, the equilibrium of protonated vs. unprotonated oximes can be shifted by modulating the pKa value of the oxime with inclusion of appropriate moieties in the oximes as will be understood by a skilled person.

In some embodiments, oximes herein described comprise a compound of Formula (III)

Formula (III)

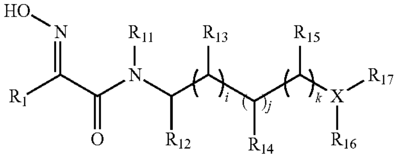

wherein

X is N or C—R10;

j and k are independently an integer from 0 or 1;

R1=H, $CH_3$; and

R10, R11, R12, R13, R14, R15, R16 and R17 are independently H, a linear or branched, alkyl, alkenyl, alkynyl, aryl, arylalkyl or alkylaryl groups having equal to or less than 18 carbon atoms, optionally containing additional one to six heteroatoms and/or one to three substituents, and wherein R11 and one of R12, R13, R14, R15, R16 and R17 or R12 and one of R13, R14, R15, R16 and R17 moieties are bonded to form at least one aromatic or aliphatic cycle.

In some embodiments, the compound of Formula (III) includes i=1, j=0, k=0, R12 and R16 are bonded to form an aromatic or aliphatic cycle, optionally R16 and R17 are further bonded to form an aromatic or aliphatic cycle, optionally R11 and R13 are bonded to form an aromatic or aliphatic cycle, or optionally R13 and R16 are bonded to form an aromatic or aliphatic cycle.

In some embodiments, the compound of Formula (III) includes i=1, j=0, k=0, R11 and R12 are bonded to form an aromatic or aliphatic cycle, optionally R12 and R16 are bonded to form an aromatic or aliphatic cycle.

In some embodiments, the compound of Formula (III) includes R16 and R17 are bonded to form an aromatic or aliphatic cycle, optionally R12 and R16 are bonded to form an aromatic or aliphatic cycle, optionally i=1, j=1, R11 and R14 are bonded to form an aromatic or aliphatic cycle.

In some embodiments, the compound of Formula (III) includes R16 and R17 are bonded to form an aromatic or aliphatic cycle, optionally R12 and R16 are bonded to form an aromatic or aliphatic cycle, optionally i=1, j=1, k=1, R11 and R14 are bonded to form an aromatic or aliphatic cycle.

In some embodiments, the compound of Formula (III) includes R16 and R17 are bonded to form an aromatic or aliphatic cycle, optionally R12 and R16 are bonded to form an aromatic or aliphatic cycle, optionally i=1, j=1, k=1, R11 and R14 are bonded to form an aromatic or aliphatic cycle and R16 and R17 are bonded to form an aromatic or aliphatic cycle.

In some embodiments, the compound of Formula (III) includes R16 and R17 are bonded to form an aromatic or aliphatic cycle, optionally R12 and R16 are bonded to form an aromatic or aliphatic cycle, optionally i=1, j=1, k=1, R11 and R14 are bonded to form an aromatic or aliphatic cycle and R16 and R17 are bonded to form an aromatic cycle.

In some embodiments, the compound of Formula (III) includes R16 and R17 are bonded to form an aromatic or aliphatic cycle, optionally R12 and R16 are bonded to form an aromatic or aliphatic cycle, optionally i=1, j=1, k=1, R11 and R14 are bonded to form an aromatic or aliphatic cycle.

In some embodiments, the compound of Formula (III) includes i=1, j=0, k=0, R12 and R16 are bonded to form an aromatic or aliphatic cycle and R16 and R17 are bonded to form an aromatic or aliphatic cycle.

In some embodiments, the compound of Formula (III) includes j=0, k=0, R11 and R16 are bonded to form part of an aromatic or aliphatic cycle, preferably R11 and R16 are bonded to form part of an aromatic or aliphatic cycle.

In some embodiments, the compound of Formula (III) includes i=1, j=0, k=0, R11 and R13 are bonded to form an aromatic or aliphatic, preferably cycle R11 and R13 are bonded to form an aromatic or aliphatic cycle.

In some embodiments, the compound of Formula (III) includes i=1, R13 and R16 are bonded to form an aromatic or aliphatic cycle.

In some embodiments, the compound of Formula (III) includes i=1, R11 and R13 are bonded to form an aromatic or aliphatic cycle.

In some embodiments, the compound of Formula (III) includes i=1, j=1, R11 and R14 are bonded to form an aromatic or aliphatic cycle.

In some embodiments, the compound of Formula (III) includes j=1, and R14 and one of R15, R16, and R17 are bonded to form a cycle, optionally R12 is a linear or branched, alkyl, alkenyl, alkynyl, aryl, arylalkyl or alkylaryl group having equal to or less than 18 carbon atoms and optionally containing additional one to six heteroatoms and/or one to three substituents.

In some embodiments, the compound of Formula (III) includes k=1, and R15 and one of R16 and R17 are bonded to form a cycle, optionally the cycle is an aliphatic cycle.

As used herein, the term "aliphatic" refers to that is an alkyl, alkenyl or alkynyl group which can be substituted or unsubstituted, linear, branched or cyclic.

As used herein the term "alkyl" as used herein refers to a linear, branched, or cyclic, saturated hydrocarbon group formed by a carbon chain. As used herein the term "carbon chain" indicates a linear or branched line of connected carbon atoms. An alkyl carbon chain can contain in some embodiments, 1 to about 18 carbon atoms, preferably 1 to about 6 carbon atoms. In particular the alkyl carbon chain can be an acyclic alkyl chain, which is an open-chain alkyl, such as methyl, ethyl, n-propyl, isopropyl, n-butyl, isobutyl, t-butyl, octyl, decyl, and the like, as well as cycloalkyl groups (groups derived from a cycloalkane by removal of a hydrogen atom from a ring and has the general formula $C_nH_{(2n-1)}$ such as cyclopentyl, cyclohexyl and the like and acyclic alkyl such as methyl, ethyl, propyl and the like. In particular, the term "cycloalkyl" encompasses a cyclic alkyl group, typically having 4 to 8, preferably 5 to 7, carbon atoms with exemplary cyclic alkyl comprising cyclopropyl, cyclobutyl, cyclohexyl, cycloheptyl, cyclooctyl; aryl includes phenyl, tolyl, xylyl, napthyl, biphenyl; heteroaryl includes pyridyl, furanyl, thiophenyl; aralkyl includes benzyl, phenethyl, phenpropyl, phenbutyl. The term "acyclic alkyl" encompasses groups such as methyl, ethyl, propyl, isopropyl, n-butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl and the various isomeric forms.

As used herein the term "alkenyl" indicates a linear, branched, or cyclic hydrocarbon group that contains at least one carbon-carbon double bond. As used herein the term "alkynyl" indicates a linear, branched, or cyclic hydrocarbon group that contains at least one carbon-carbon triple bond.

The term "aryl" as used herein, and unless otherwise specified, refers to an aromatic substituent containing a single aromatic ring or multiple aromatic rings that are fused together, directly linked, or indirectly linked (such that the different aromatic rings are bound to a common group such as a methylene or ethylene moiety). Preferred aryl groups contain 5 to 12 carbon atoms, and particularly preferred aryl groups contain 5 to 6 carbon atoms. Exemplary aryl groups contain one aromatic ring or two fused or linked aromatic rings, e.g., phenyl, naphthyl, biphenyl, diphenylether, diphenylamine, benzophenone, and the like. "Substituted aryl" refers to an aryl moiety substituted with one or more substituent groups, and the terms "heteroatom-containing aryl" and "heteroaryl" refer to aryl substituents in which at least one carbon atom is replaced with a heteroatom, such as nitrogen, oxygen or sulfur.

The term "aralkyl" as used herein refers to an alkyl group with an aryl substituent, and the term "alkaryl" as used herein refers to an aryl group with an alkyl substituent, wherein "aryl" and "alkyl" are as defined above. In some embodiments, alkaryl and aralkyl groups contain 6 to 12 carbon atoms, and particularly alkaryl and aralkyl groups contain 6 to 16 carbon atoms. Alkaryl groups include, for example, p-methylphenyl, 2,4-dimethylphenyl, p-cyclohexylphenyl, 3-ethyl-cyclopenta-1,4-diene, and the like. Examples of aralkyl groups include, without limitation, benzyl, 2-phenyl-ethyl, 3-phenyl-propyl, 4-phenyl-butyl, 5-phenyl-pentyl, 4-phenylcyclohexyl, and the like. The terms "alkaryloxy" and "aralkyloxy" refer to substituents of the formula —OR wherein R is alkaryl or aralkyl, respectively, as defined.

The terms "cyclic", "cycle" and "ring" when referred to a group of atoms refer to alicyclic or aromatic groups that in some cases can be substituted and/or heteroatom containing, and that may be monocyclic, bicyclic, or polycyclic. The term "alicyclic" is used in the conventional sense to refer to an aliphatic cyclic moiety, as opposed to an aromatic cyclic moiety, and may be monocyclic, bicyclic or polycyclic.

Unless otherwise indicated, the term "substituted" as in "substituted alkyl," "substituted aryl," and the like, is meant that in the, alkyl, aryl, or other moiety, at least one hydrogen atom bound to a carbon (or other) atom is replaced with one or more non-hydrogen substituents. As used herein, a "substituent" is an atom or group of atoms substituted in place of a hydrogen atom on the main chain of a hydrocarbon. Examples of substituents include, without limitation: functional groups such as, hydroxyl, sulfhydryl, $C_1$-$C_{12}$ alkoxy, $C_2$-$C_{12}$ alkenyloxy, $C_2$-$C_{12}$ alkynyloxy, $C_5$-$C_{12}$ aryloxy, $C_6$-$C_{12}$ aralkyloxy, $C_6$-$C_{12}$ alkaryloxy, acyl (including $C_2$-$C_{12}$ alkylcarbonyl (—CO-alkyl) and $C_6$-$C_{12}$ arylcarbonyl (—CO-aryl)), acyloxy (—O-acyl, including $C_2$-$C_{12}$ alkylcarbonyloxy (—O—CO-alkyl) and $C_6$-$C_{12}$ arylcarbonyloxy (—O—CO-aryl)), $C_2$-$C_{12}$ alkoxycarbonyl (—(CO)—O-alkyl), $C_6$-$C_{12}$ aryloxycarbonyl (—(CO)—O-aryl), $C_2$-$C_{12}$ alkylcarbonato (—O—(CO)—O-alkyl), $C_6$-$C_{12}$ arylcarbonato (—O—(CO)—O-aryl), carboxy (—COOH), carboxylato (—$COO^-$), carbamoyl (—(CO)—$NH_2$), mono-($C_1$-$C_{12}$ alkyl)-substituted carbamoyl (—(CO)—NH($C_1$-$C_{12}$ alkyl)), di-($C_1$-$C_{12}$ alkyl)-substituted carbamoyl (—(CO)—N($C_1$-$C_{12}$ alkyl)$_2$), mono-($C_5$-$C_{12}$ aryl)-substituted carbamoyl (—(CO)—NH-aryl), di-($C_5$-$C_{12}$ aryl)-substituted carbamoyl (—(CO)—N($C_5$-$C_{12}$ aryl)$_2$), alkyl), N—($C_5$-$C_{12}$ aryl)-substituted carbamoyl, thiocarbamoyl (—(CS)—$NH_2$), mono-($C_1$-$C_{12}$ alkyl)-substituted thiocarbamoyl (—(CO)—NH ($C_1$-$C_{12}$ alkyl)), di-($C_1$-$C_{12}$ alkyl)-substituted thiocarbamoyl (—(CO)—N($C_1$-$C_6$ alkyl)$_2$), mono-($C_5$-$C_{12}$ aryl)-substituted thiocarbamoyl (—(CO)—NH-aryl), di-($C_5$-$C_6$ aryl)-substituted thiocarbamoyl (—(CO)—N($C_5$-$C_6$ aryl)$_2$), alkyl), N—($C_5$-$C_6$ aryl)-substituted thiocarbamoyl, carbamido (—NH—(CO)—$NH_2$), cyano (—C≡N), cyanato thiocyanato formyl (—(CO)—H), thioformyl (—(CS)—H), amino (—$NH_2$), mono-($C_1$-$C_{12}$ alkyl)-substituted amino, di-($C_1$-$C_{12}$ alkyl)-substituted amino, mono-($C_5$-$C_{12}$ aryl)-substituted amino, di-($C_5$-$C_6$ aryl)-substituted amino, $C_2$-$C_{12}$ alkylamido (—NH—(CO)-alkyl), $C_6$-$C_{12}$ arylamido (—NH—(CO)-aryl), imino (—CR═NH where R=hydrogen, $C_1$-$C_{12}$ alkyl, $C_5$-$C_{12}$ aryl, $C_6$-$C_{12}$ alkaryl, $C_6$-$C_{12}$ aralkyl, etc.), $C_2$-$C_{12}$ alkylimino (—CR═N(alkyl), where R=hydrogen, $C_1$-$C_{12}$ alkyl, $C_5$-$C_{12}$ aryl, $C_6$-$C_{12}$ alkaryl, $C_6$-$C_2$ aralkyl, etc.), arylimino (—CR═N(aryl), where R=hydrogen, $C_1$-$C_{12}$ alkyl, $C_5$-$C_{12}$ aryl, $C_6$-$C_{12}$ alkaryl, $C_6$-$C_{12}$ aralkyl, etc.), nitro (—$NO_2$), nitroso (—NO), sulfo (—$SO_2$—OH), sulfonato (—$SO_2$-01, $C_1$-$C_{12}$ alkylsulfanyl (—S-alkyl; also termed "alkylthio"), $C_5$-$C_{12}$ arylsulfanyl (—S-aryl; also termed "arylthio"), $C_1$-$C_{12}$ alkylsulfinyl (—(SO)-alkyl), $C_5$-$C_{12}$ arylsulfinyl (—(SO)-aryl), $C_1$-$C_{12}$ alkylsulfonyl (—$SO_2$-alkyl), $C_5$-$C_{12}$ arylsulfonyl (—$SO_2$-aryl), boryl (—$BH_2$), borono (—B(OH)$_2$), boronato (—B(OR)$_2$ where R is alkyl or other hydrocarbyl), phosphono (—P(O)(OH)$_2$), phosphonato (—P(O)($O^-$)$_2$), phosphinato (—P(O)($O^-$), phospho (—$PO_2$), phosphino (—$PH_2$), silyl (—$SiR_3$ wherein R is hydrogen or hydrocarbyl), and silyloxy (—O-silyl); and the hydrocarbyl moieties $C_1$-$C_{12}$ alkyl (preferably $C_1$-$C_{12}$ alkyl, more preferably $C_1$-$C_6$ alkyl), $C_2$-$C_{12}$ alkenyl (preferably $C_2$-$C_{12}$ alkenyl, more preferably $C_2$-$C_6$ alkenyl), $C_2$-$C_{12}$ alkynyl (preferably $C_2$-$C_{12}$ alkynyl, more preferably $C_2$-$C_6$ alkynyl), $C_5$-$C_{12}$ aryl (preferably $C_5$-$C_{12}$ aryl), $C_6$-$C_{12}$ alkaryl (preferably $C_6$-$C_{12}$ alkaryl), and $C_6$-$C_{12}$ aralkyl (preferably $C_6$-$C_{12}$ aralkyl), halo (such as F, Cl, Br, I), haloalkyl (such as $CCl_3$ or $CF_3$). Exemplary substituents also comprise one or more of the following groups: halo (such as F, Cl, Br, or I), haloalkyl (such as $CCl_3$ or $CF_3$), alkoxy, alkylthio, hydroxy, carboxy, carbonyl, epoxy, alkyloxycarbonyl, alkylcarbonyloxy, amino, carbamoyl, urea, alkylurea or thiol and additional groups identifiable by a skilled person upon reading of the present disclosure.

As used herein the terms "heteroatom-containing" or "hetero-" indicated in connection with a group, refers to a hydrocarbon group in which one or more carbon atoms is replaced with an atom other than carbon, e.g., nitrogen, oxygen, sulfur, phosphorus or silicon, typically nitrogen, oxygen or sulfur. Exemplary "heteroatoms" comprise as N, O, S and P, and can be present in a compound by a covalent bond to each of two carbon atoms, thus interrupting the two carbon atoms. Accordingly, the term "heteroalkyl" refers to an alkyl substituent or group that is heteroatom-containing, the term "heterocyclic" refers to a cyclic substituent that is heteroatom-containing, the terms "heteroaryl" and "heteroaromatic" respectively refer to "aryl" and "aromatic" substituents or groups that are heteroatom-containing, and the like. It should be noted that a "heterocyclic" group or compound may or may not be aromatic, and further that "heterocycles" may be monocyclic, bicyclic, or polycyclic as described above with respect to the term "aryl." Examples of heteroalkyl groups include alkyl ethers, secondary and tertiary alkyl amines, amides, alkyl sulfides, alkoxyaryl, alkylsulfanyl-substituted alkyl, N-alkylated amino alkyl, and the like. Examples of heteroaryl substituents include pyrrolyl, pyrrolidinyl, pyridinyl, quinolinyl, indolyl, pyrimidinyl, imidazolyl, 1,2,4-triazolyl, tetrazolyl, etc., and examples of heteroatom-containing alicyclic groups are pyrrolidino, morpholino, piperazino, piperidino, and addition group identifiable by a skilled person. Accordingly, as an example, the term "substituted alkyl" refers to alkyl substituted with one or more substituent groups.

If not otherwise indicated, the terms "alkyl" and "lower alkyl" include linear, branched, cyclic, unsubstituted, substituted, and/or heteroatom-containing alkyl and lower alkyl, respectively. As used herein, a lower alkyl has 1-4 carbon atoms on the alkyl chain.

"Heterocycloalkyl" refers to a saturated or partially saturated monocyclic, bicyclic, or polycyclic ring in which at least one carbon atom is replaced with a heteroatom selected from S, O, P and N, preferably from 1 to 3 heteroatoms in at least one ring.

In some embodiments, oximes herein described comprise one or more compounds of Formula (II), wherein i=1, j=0, k=0, R12 and R16 are linked to form an aromatic or aliphatic cycle.

In some embodiments, oximes herein described comprise one or more compounds of Formula (II), wherein i=1, j=0, k=0, R11 and R12 are linked to form an aromatic or aliphatic cycle.

In some embodiments, oximes herein described comprise one or more compounds of Formula (II), wherein R16 and R17 are linked to form an aromatic or aliphatic cycle.

In some embodiments, the alkyl, alkenyl, alkynyl, aryl, arylalkyl or alkylaryl groups can optionally comprise one to six heteroatoms or one to three substituents.

In some embodiments, oximes herein described comprise one or more compounds of Formula (II), wherein j=1, k=1; and R14 and one of R15, R16 and R17, or R15 and one of R16 and R17 moieties are linked to form a backbone cyclic moiety.

In some embodiments, oximes herein described comprise a compound of Formula (III), wherein i=1, j=0, k=0, R11 and R12 are linked to form part of aliphatic cycle.

In some embodiments, oximes herein described comprise a compound of Formula (III), wherein i=1, j=1, k=1, R11 and R12 are linked to form an aliphatic cycle.

In some embodiments, oximes herein described comprise a compound of Formula (III), wherein i=1, j=0, k=0, R11 and R13 are linked to form aliphatic cycle.

In some embodiments, oximes herein described comprise a compound of Formula (III), wherein i=1, R12 and R13 are linked to form an aliphatic cycle.

In some embodiments, oximes herein described comprise a compound of Formula (III), wherein i=1, R11 and R13 are linked to form an aliphatic cycle.

In some embodiments, oximes herein described comprise compounds of Formula (IIIa)

Formula (IIIa)

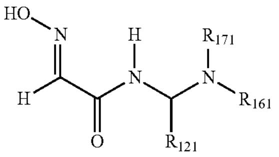

wherein

R121, R161 and R171 are independently H, a linear or branched, alkyl, alkenyl, alkynyl, aryl, arylalkyl or alkylaryl groups having equal to or less than 18 carbon atoms, optionally additional one to six heteroatoms or one to three substituents containing, wherein R121 and one of R161 and R171 moieties are bonded to form an aromatic or aliphatic cycle.

The compounds of Formula (IIIa) are relatively small, preferably having a molecular weight of under 700, more preferably a molecular weight of under 500, and are hydrophilic with a cogP of 2.0 or less.

In some embodiments, oximes herein described comprise compounds of Formula (IIa1)

Formula (IIIa1)

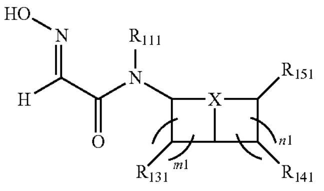

wherein

X is N or C—R102;

R102, R111, R131, R141 and R151 independently are H, a linear or branched, alkyl, alkenyl, alkynyl, aryl, arylalkyl or alkylaryl groups having equal to or less than 18 carbon atoms, optionally additional one to six heteroatoms or one to three substituents containing, and ml and n1 are independently an integer from 0 to 5, preferably an integer from 1 to 3.

The compounds of Formula (IIIa1) preferably have a molecular weight of under 700, more preferably a molecular weight of under 500, and are hydrophilic with a c log P of 2.0 or less.

In some embodiments, oximes herein described comprise compounds of Formula (IIIb)

Formula (IIIb)

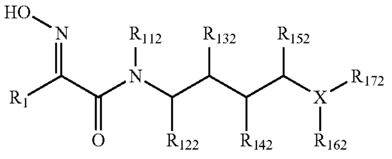

wherein

X is N or C—R102;

R1=H, CH3; and

R102, R112, R122, R132, R142, R152, R162 and R172 independently are H, a linear or branched, alkyl, alkenyl, alkynyl, aryl, arylalkyl or alkylaryl groups having equal to or less than 18 carbon atoms, optionally additional one to six heteroatoms or one to three substituents containing, wherein R112 and one of R122, R132, R142, R152, R162 and R172 or R122 and one of R132, R142, R152, R162 and R172 moieties are bonded to form an aromatic or aliphatic cycle.

In some embodiments, compounds of Formula (IIIb) have c log P in a range of 2.0-4.5.

In some embodiments, oximes herein described comprise compounds of Formula (IIIb1)

Formula (IIIb1)

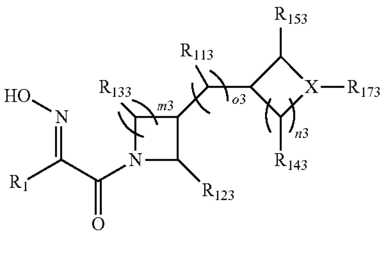

wherein

X is N or C—R102;

R1=H, CH3;

R102, R113, R123, R133, R143, R152 and R173 independently are H, a linear or branched, alkyl, alkenyl, alkynyl, aryl, arylalkyl or alkylaryl groups having equal to or less than 18 carbon atoms, optionally additional one to six heteroatoms or one to three substituents containing; and m3 and n3 are independently an integer from 0 to 5, preferably an integer from 1 to 3, and o3 is an integer from 0 to 2.

In some embodiments, compounds of Formula (IIIb1) have c log P in a range of 2.0-4.5.

In some embodiments, oximes herein described comprise compounds of Formula (IIIc)

Formula (IIIc)

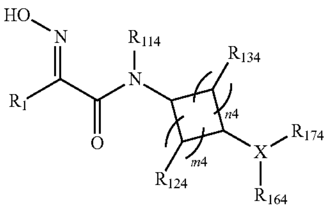

wherein

X is N or C—R102;

R1=H, CH3;

R102, R114, R124, R134, R164 and R174 independently are H, a linear or branched, alkyl, alkenyl, alkynyl, aryl, arylalkyl or alkylaryl groups having equal to or less than 18 carbon atoms, optionally additional one to six heteroatoms or one to three substituents containing, and m4 and n4 are independently an integer from 0 to 5, preferably an integer from 1 to 3 and wherein m4+n4 is an integer equal 0 to 6.

In some embodiments, compounds of Formula (IIIc) have c log P in a range of 2.0-4.5.

In some embodiments, oximes herein described comprise compounds of Formula (IIId)

Formula (IIId)

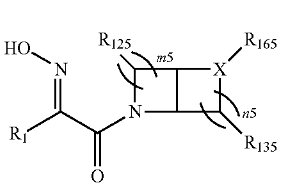

wherein

X is N or C—R102;

R1=H, CH3; and

R102, R125, R135, and R165 are independently H, a linear or branched, alkyl, alkenyl, alkynyl, aryl, arylalkyl or alkylaryl groups having equal to or less than 18 carbon atoms, optionally additional one to six heteroatoms or one to three substituents containing, and m5 and n5 are independently an integer from 0-5, preferably an integer from 1 to 3.

In some embodiments, compounds of Formula (IIId) have c log P in a range of 2.0-4.5.

In some embodiments, oximes herein described comprise one or more compounds of Formula (IV)

Formula (IV)

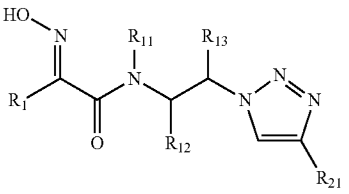

wherein R21=H, a linear or branched, optionally additional one to six heteroatoms or one to three substituents containing, alkyl, alkenyl, alkynyl, aryl, arylalkyl or alkylaryl carbon atom having equal to or less than 18 carbon atoms and R1, R11, R12, and R13 are as defined for Formula (III).

In some embodiments, of Formula (IV), R11 and one of R12, R13, are bonded to form an aromatic or aliphatic cycle.

In some embodiments, oximes herein described comprise a compound of Formula (IV), wherein, R11 and R13 are linked to form an aliphatic cycle.

In some embodiments, oximes herein described comprise a compound of Formula (IV), wherein R11 and R12 are linked to form an aliphatic cycle.

In some embodiments, oximes herein described comprise a compound of Formula (IV), wherein R11 and R13 are linked to form an aliphatic cycle.

In some embodiments, oximes herein described comprise one or more compounds of Formula (V)

Formula (V)

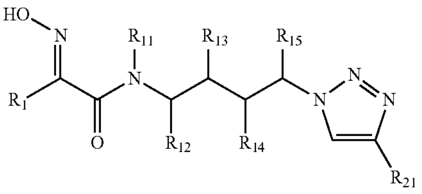

wherein R21=H, a linear or branched, optionally additional one to six heteroatoms or one to three substituents containing, alkyl, alkenyl, alkynyl, aryl, arylalkyl or alkylaryl carbon atom having equal to or less than 18 carbon atoms, and optionally containing additional one to six heteroatoms or one to three substituents, and R1, R11, R12, R13, R14 and R15 are as defined for Formula (III).

In some embodiments, of Formula (V), R11 and one of R12, R13, R14 and R15 are bonded to form an aromatic or aliphatic cycle.

In some embodiments, functionalities that can be used as a labile protective group can be added to the oxime oxygen of an oxime of the present disclosure. The wording "labile protective group" as used herein refers to an organic chemical moiety that can form a covalent bond with the oxime oxygen which can be broken chemically or enzymatically under normal physiological conditions to release oxime hydroxyl group. In some embodiments, it is expected that the oxime oxygen can be protected as an ester (e.g. acetyl, trifluoroacetyl or even as a pivaloyl ester).

In some embodiments, an oxime with a labile protective group can have the structure of Formula (VI)

Formula (VI)

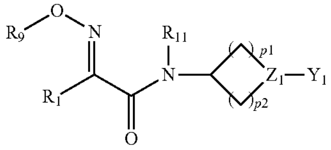

wherein

R1, and R11 are as defined for Formula (III), R9 is H, a linear or branched, optionally one to three substituents containing, alkyl, alkenyl, alkynyl, aryl, arylalkyl, alkylaryl, heteroalkyl, heteroalkenyl, heteroalkynyl, heteroaryl, heteroarylalkyl or heteroalkylaryl, each having 18 or less carbon atoms and 0-12 heteroatoms, and is convertible to H in vivo, p1 is an integer from 0 to 5, p2 is an integer from 0 to 5 and p1+p2 is an integer from 1 to 5, Z1 is N or C—R20, wherein R20=H, a linear or branched, optionally one to three substituents containing, alkyl, alkenyl, alkynyl, aryl, arylalkyl, alkylaryl, heteroalkyl, heteroalkenyl, heteroalkynyl, heteroaryl, heteroarylalkyl or heteroalkylaryl, each having 12 or less carbon atoms and 0-6 heteroatoms, Y1=H, a linear or branched, optionally one to three substituents containing, alkyl, alkenyl, alkynyl, aryl, arylalkyl, alkylaryl, heteroalkyl, heteroalkenyl, heteroalkynyl, heteroaryl, heteroarylalkyl or heteroalkylaryl, each having 12 or less carbon atoms and 0 to 6 heteroatoms.

In oximes of Formula (VI) R9 provides an exemplary labile protective group for the oxygen of the oxime moiety. Preferably, R9 is selected from the group consisting of R9a, R9b, R9c, R9d, R9e and R9f as represented by the following corresponding formulas:

R9a

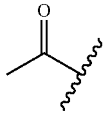

R9b

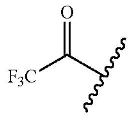

R9c

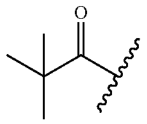

R9d

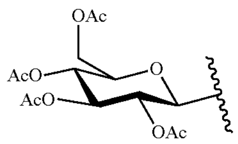

R9e

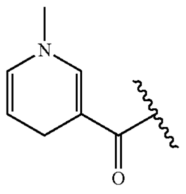

-continued

R9f

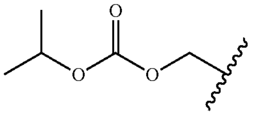

wherein the wavy line indicates a point of attachment to the oxime oxygen

In embodiments wherein the oximes comprise labile protective groups, the labile protective group can be cleaved by a hydrolase such as non-specific esterases within the brain tissue lumen. Regarding this class of compounds, the propensity towards hydrolysis can be modulated by choosing a particular labile protective group such as an ester. Thus, pivaloyl esters are more long-lived than their acetyl and trifluoroacetyl counterparts as they are degraded more slowly by esterases. Alternatively, protecting the oxime oxygen can be performed with a carbohydrate motif, for example glucose as shown in formula R9d. The example in formula R9d features a peracetylated glucose unit which has a high lipophilicity relative to their deacetylated counterparts.

Exemplary compounds of formula IV following release of the labile protective groups have structures (VIa) to (VId) below (VIa)

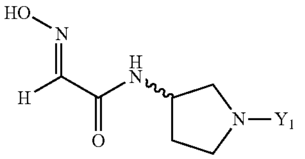

(VIb)

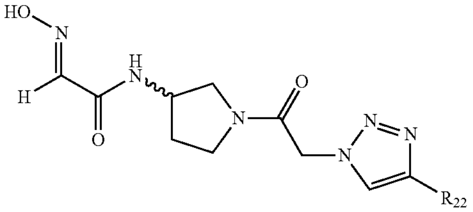

(VIc)

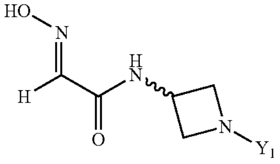

(VId)

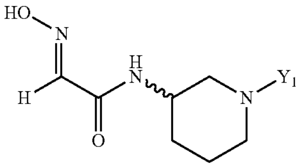

In some embodiment, an oxime with a labile protective group can have the structure of Formula (VII)

Formula (VII)

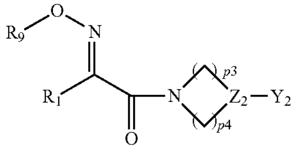

wherein

R9 is H, a linear or branched, optionally one to three substituents containing, alkyl, alkenyl, alkynyl, aryl, arylalkyl, alkylaryl, heteroalkyl, heteroalkenyl, heteroalkynyl, heteroaryl, heteroarylalkyl or heteroalkylaryl, each having 18 or less carbon atoms and 0-12 heteroatoms, and is convertible to H in vivo, R1 is as defined for Formula (III), p3 is an integer from 0 to 5, p4 is an integer from 0 to 5 and p3+p4 is equal to an integer from 1 to 5, Z2 is N or C—R20, wherein R20=H, a linear or branched, optionally one to three substituents containing, alkyl, alkenyl, alkynyl, aryl, arylalkyl, alkylaryl, heteroalkyl, heteroalkenyl, heteroalkynyl, heteroaryl, heteroarylalkyl or heteroalkylaryl, each having 12 or less carbon atoms and 0-6 heteroatoms, Y2=H, a linear or branched, optionally one to three substituents containing, alkyl, alkenyl, alkynyl, aryl, arylalkyl, alkylaryl, heteroalkyl, heteroalkenyl, heteroalkynyl, heteroaryl, heteroarylalkyl or heteroalkylaryl, each having 12 or less carbon atoms and 0 to 6 heteroatoms.

Exemplary oximes of formula (VII) following release of the labile protective group can have the formulas from (VIIa) to (VIII) below.

(VIIa)

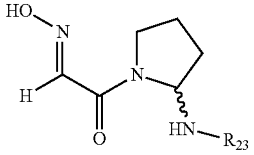

(VIIb)

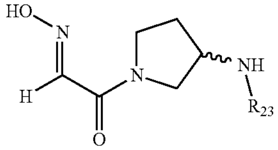

(VIIc)

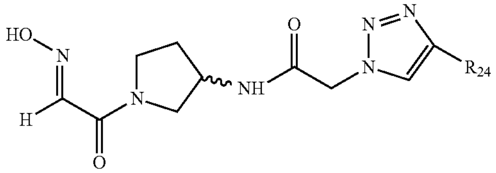

(VIId)

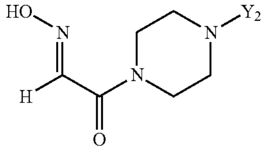

-continued (VIIe)

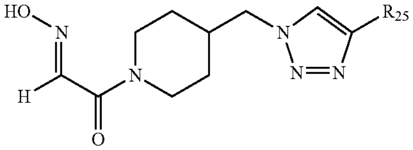

(VIIf)

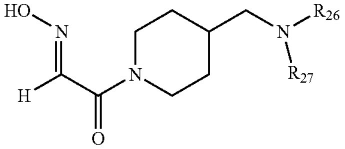

In some embodiments the oximes herein described can be optically active, wherein an optically active neutral oxime can prepared as an optically pure enantiomer or as a racemate. In the case a racemate neutral oxime is obtained as a final reaction product, the racemate neutral oxime can be resolved into enantiomers, for example, through chromatography with a chiral stationary phase of a separation column.

Figure 11:
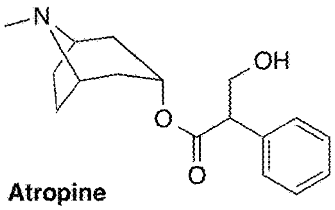
FIG. 11 shows chemical structures of exemplary compounds described in the application.
Figure 11:
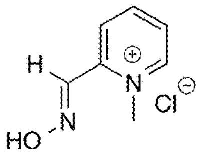
Figure 11:
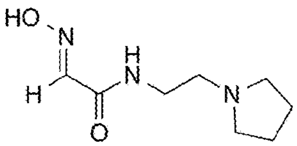
Figure 11:
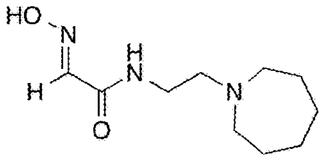
Figure 11:
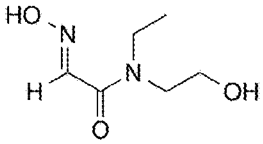
Figure 11:
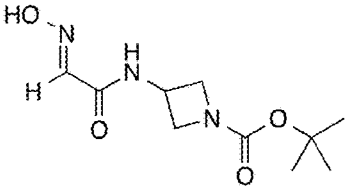
Figure 11:
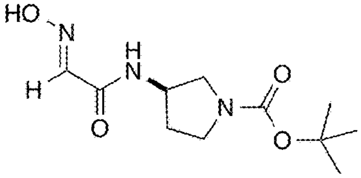
Figure 12:
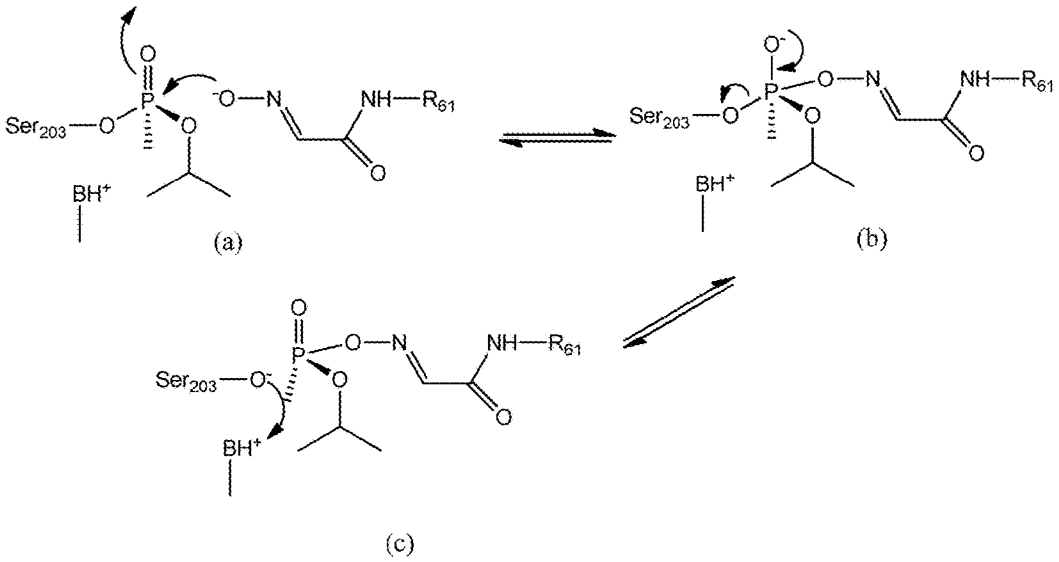
FIG. 12 shows an exemplary schematic illustration of the reactivation of sarin-adducted human AChE by an neutral oxime: (a) model of a co-complex of sarin-adducted protein active site and an oxime anion, (b) a productive inline attack of oxime anion on sarin phosphorus, and (c) reactivated human AChE with the sarin phosphorus covalently bonded to oxime oxygen.

In some embodiments, neutral oximes include oximes that may not be protonated under physiological conditions as shown by exemplary compounds such as CV9-076, CV9-086 and CV9-087 in FIG. 11. In the exemplary embodiment of CV9-076, no such DN nitrogen exists, only an AN is present. In the case of CV9-086 and CV9-087, the DN is protected as a carbamate, and it will not protonate under physiological conditions.

In several embodiments, oximes herein described can be used for reactivation of a nerve agent-inhibited acetylcholinesterase (AChE) and/or for inactivation of a nerve agent.

The term “nerve agent” refers to a chemical that disrupts the mechanism by which nerves transfer messages to organs. In particular, nerve agent in the sense of the disclosure refers to a class of phosphorus-containing organic chemicals capable of blocking acetylcholinesterase (AChE), an enzyme that is capable of catalyzing the hydrolysis acetylcholine, a neurotransmitter.

All nerve agents belong chemically to the group of organo-phosphorus compounds. Exemplary nerve agents in the sense of the disclosure have the structural Formula (VIII)

(VIII)

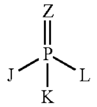

wherein

Z is O or S;

J can be hydrogen, a C1-C6 alkyl group, such as, methyl, ethyl, n-propyl, and isopropyl group, or an amino group NR71R72, wherein R71 and R72 are independently a C1 to C4 alkyl or heteroalkyl group.

K is selected from F, Cl, Br, I, CN and SCH2CH2N[CH(CH3)2]2;

L is a C1 to C8 linear or branched alkoxy group, a O-cyclohexyl, a 3,3-dimethylbutan-2-yl (i.e. O-pinacolyl).

In some embodiments the C1-C8 linear or branched alkoxy group is O—CH3, O—CH2CH3, O—CH2CH2CH3 and O—CH(CH3)2 (herein also indicated O-iPr), In some embodiments, nerve agents in the sense of the disclosure have the structural Formula (IX)

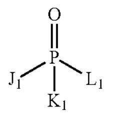

(IX)

wherein,

J1 can be hydrogen or an alkyl group such as, methyl, ethyl and n-propyl, isopropyl.

K1 is selected from F, and CN;

L1 is a C1 to C8 linear or branched alkoxy group such as O—CH3, O—CH2CH3, O—CH2CH2CH3 and O—CH(CH3)2 (i.e. O-iPr), 0-cyclohexyl, 3,3-dimethylbutan-2-yl (i.e. O-pinacolyl).

In some embodiments, nerve agents in the sense of the disclosure have the structural Formula (X)

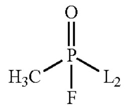

(X)

wherein

L2 is a C1 to C8 linear or branched alkoxy group such as O—CH3, O—CH2CH3, O—CH2CH2CH3 and O—CH(CH3)2 (i.e. O-iPr), O-cyclohexyl, and 3,3-dimethylbutan-2-yl (O-pinacolyl)

In some embodiments, nerve agents in the sense of the disclosure have the structural Formula (XI)

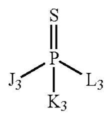

(XI)

wherein,

J3 is an amino group such as N(CH3)2, N(CH3)(C2H5) or N(CH2CH3)2.

K3 is a thiolate group SR75, wherein R75 is a alkyl, alkenyl, alkynyl, aryl, arylalkyl, alkylaryl, heteroalkyl, heteroalkenyl, heteroalkynyl, heteroaryl, heteroarylalkyl or heteroalkylaryl, each having 12 or less carbon atoms and 0-3 heteroatoms. An exemplary R75 includes CH2CH2N[CH(CH3)2]2.

L3 is selected from the group consisting of O—CH3, O—CH2CH3, O—CH2CH2CH3, O—CH(CH3)2, O-cyclohexyl, and 3,3-dimethylbutan-2-yl.

Nerve agents in the sense of the disclosure can comprise G-agents tabun (GA), sarin (GB), soman (GD), GF, V-agents VX (S-2-(diisopropylamino)ethyl O-ethyl methylphosphonothiolate) and Russian-VX (S-2-(diethylamino)ethyl O-isobutyl methylphosphonothiolate) and additional compounds identifiable by a skilled person upon reading of the present disclosure. The reactivation of the adducted serine-agent complex depends on how the neutral oxime works against adducted-AChE and how fast these adducted serine-agent complex "age" within the active site. Aging is the process by which the adducted serine-agent complex loses another leaving group (undergoes hydrolysis) but still remains adducted to the catalytic serine residue of the AChE enzyme.

Nerve agents such as a sarin has been described to be used, for example, in different environmental settings that are amenable to decontamination with the oximes as described herein (Haines et al 2014, Tu et al 2014, Okumara et al 2005, Okumura et al 1996, Dolgin et al 2013).

In some embodiments, oximes herein described can be used to reactivate a nerve agent-inhibited acetylcholinesterase (AChE).

In embodiments, a method to reactivate a nerve agent inhibited acetylcholinesterase in an individual is described, the method comprising:

administering to the individual an effective amount of at least one oxime compound as described herein for a time and under a condition to allow contact between the at least one compound and a nerve agent inhibited acetylcholinesterase in the individual thus resulting in a reactivated acetylcholinesterase.

The term "acetylcholinesterase" or (AChE) as used in the present disclosure indicates an enzyme that catalyzes the breakdown of acetylcholine and possibly of other choline esters. Typically, AChE is a hydrolase that hydrolyzes the neurotransmitter acetylcholine and/or other choline esters. In some cases, one molecule of AChE can degrade about 25000 molecules of acetylcholine (ACh) per second, approaching the limit allowed by diffusion of the substrate. Typically, the active site of AChE comprises 2 subsites—the anionic site and the esteratic subsite. In living organisms, AChE can be found in many types of conducting tissue: nerve and muscle, central and peripheral tissues, motor and sensory fibers, and cholinergic and noncholinergic fibers. Typically the activity of AChE is higher in motor neurons than in sensory neurons. Acetylcholinesterase can also be found on the red blood cell membranes, where different forms constitute the Yt blood group antigens. Acetylcholinesterase exists in multiple molecular forms, which possess similar catalytic properties, but differ in their oligomeric assembly and mode of attachment to the cell surface. In mammals, acetylcholinesterase is encoded by a single AChE gene while some invertebrates have multiple acetylcholinesterase genes. Diversity in the transcribed products from the sole mammalian gene arises from alternative mRNA splicing and post-translational associations of catalytic and structural subunits. There are three known forms: T (tail), R (read through), and H(hydrophobic). Accordingly, exemplary AChE comprise $AChE_T$, $AChE_R$ and $AChE_H$ as will be understood by a skilled person.

In some embodiments herein described, oximes herein described are capable of reactivating an inhibited acetylcholinesterase wherein the term "inhibited acetylcholinesterase" or "nerve agent inhibited", as used herein, refers to acetylcholinesterase with a reduced activity or no detectable activity following formation of a covalent bond between acetylcholinesterase and the phosphorus of a nerve agent.

The term, "reactivating" and "reactivation" when referred to an inhibited acetylcholinesterase indicates a detectable increase of in the enzymatic activity of the inhibited acetylcholinesterase in catalyzing the hydrolysis of acetylcholine to choline and acetate. Reactivation of nerve-agent inhibited acetylcholinesterase generally involves breaking up of a covalent bond between serine oxygen of the enzyme and the phosphorus of nerve agent, without being bound by theory, an example can be an oxime nucleophilic attack on the phosphorus of the nerve agent and releasing the bound serine group.

Oximes of the disclosure capable of reactivating an inhibited AChE have a structure configured to have a pKa of the protonated form of the oxime between 7 and 9. In some of those embodiments the oximes of the disclosure comprise a DN.

Exemplary oximes of the disclosure herein described comprise the following compounds such as (VIId)

(VIId)

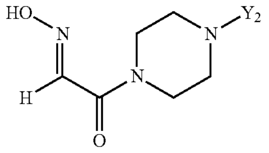

The reactivation of an inhibited AChE can be determined by various techniques identifiable by a skilled person, such as a modified Ellman's assay in which thiol ester acetylthiocholine is used as an enzyme substrate in place of acetylcholine for the reactivated AChE. In the modified Ellman's assay, the reactivated AChE catalyzes the hydrolysis of acetylthiocholine to generate thiocholine which reacts with a colorimetric indicator 5,5'-dithiobis-(2-nitrobenzoic acid) (DTNB) to form 2-nitro-5-thiobenzoic acid which can be detected or quantified in a spectrophotometer by measuring the absorbance of visible light at 410 nm.

Oximes herein described capable of reactivating an inhibited AChE can be used in treatment and/or prevention in an individual of a condition associated with exposure of the individual to a nerve agent, and/or in decontamination of an environment from one or more nerve agents as will be understood by a skilled person upon reading of the present disclosure.

In some embodiments, oximes herein described are capable of inactivating a nerve agent bound or unbound to an AChE. In particular, oximes herein described are capable in some embodiments to inactivate the nerve agent by decomposing one or more nerve agents bound or unbound to AChE. The term "decompose" or "decomposition" refers to the act or process of transforming the chemical structure of a nerve agent to less toxic or non-toxic form. The decomposition of nerve agent as represented by Formula (IX) can, for example, include the substitution of J with an oxime oxygen of Formula (III). The decomposition of a nerve agent could include hydrolysis of a nerve agent catalyzed by any of the oximes as described herein, for example as represented by Formula (III).

In some embodiments, hydrolysis of a nerve agent catalyzed by one or more oximes herein described can have a half-life of 1 hour, preferably 15 minutes. Oximes herein described capable of inactivating one or more nerve agent can be used in treatment and/or prevention in an individual of a condition associated with exposure of the individual to a nerve agent, and/or in decontamination of an environment from one or more nerve agents as will be understood by a skilled person upon reading of the present disclosure.

In some embodiments, the oximes or their resulting reaction products during the hydrolysis of a nerve agent is environmentally-friendly. The term "environmentally-friendly" as used herein refers to oximes and their reaction products during the hydrolysis of a nerve agent is in general compliance with "Guides For The Use Of Environmental Marketing Claims" (available online at the date of filing of the present disclosure at the website, www.ftc.gov/sites/default/files/attachments/press-releases/ftc-issues-revised-green-guides/greenguides.pdf). More specifically, the environmentally-friendly oxime or its products are not toxic to individuals or polluting to the environment in normal use.

Exemplary oximes capable of inactivating a nerve agent comprising;

(VIIa)

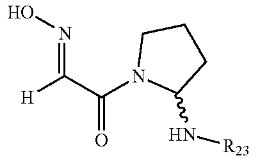

(VIIb)

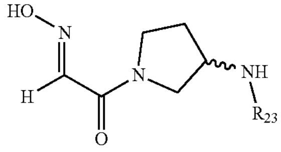

In several embodiments, the oximes herein described are capable of penetrating the blood brain barrier (BBB). The term "blood brain barrier (BBB)-penetrating" as used herein refers a physiological property of an molecule such as a neutral oxime to transport from circulating blood to brain extracellular fluid (BECF) in the central nervous system (CNS) of a subject. BBB-penetrating compounds should ideally be neutral, and partially hydrophobic to the point where they can easily pass through the core of the membrane without encountering a high energetic barrier.

In some embodiments, oximes capable of crossing the BBB can be configured such that the pKa, and thus the overall equilibrium of protonated/unprotonated forms of the oximes, are modulated through inductive effects in target environments before and after crossing the BBB. These inductive effects can be provided into an oxime molecule by electron-rich or electron-poor functionality located on a carbon atom zero to three carbon atoms, preferably zero to one carbon atom, away from the DG (and possibly the DN nitrogen if present) to be protonated. In some embodiments, electron donating group, i.e. electron-rich functionality, is selected from the group consisting of phenoxide, ether, amide nitrogen, ester carboxylate, phenyl, and vinyl. In some embodiments, an electron withdrawing group, i.e. electron-poor functionality, is selected from the group consisting of ketone, ester, amide carbonyl, halides, trihchloromethyl, trifluoromethyl, cyano, and nitro.

In embodiments herein described, electron donating or electron withdrawing groups can be included in on a carbon atom zero to three carbon atoms, preferably zero to one carbon atom, away from the DG (and possibly the DN nitrogen if present) to be protonated, to switch the general equilibrium between the protonated/unprotonated form of the compound (at the DG and in particular at the DN if present) under physiological conditions (at pH 7.4) so that the pKa is selected between 7 and 9, preferably between 7 and 8, and most preferably 7.5 and 8, to allow passage of the BBB and an equilibrium between protonated and unprotonated forms of oxime after passage that is allows the electrostatic interactions between the oxime and the AChE.

In some embodiments, the pKa of the oximes before passing the BBB is expected to have a direct effect on the compound's overall BBB permeability since if the compound exists mainly in its protonated form (e.g. 4:1 over the unprotonated form) the ability of the compound to cross the BBB would be severely hampered. The opposite is true for the unprotonated compound that would exhibit a more lipophilic-like behavior resulting in an enhanced BBB permeability profile. A skilled person will be able to identify the specific combinations of atoms and substituents, and in particular electron donating groups and electron withdrawing groups that can be included in the oximes of the disclosure to provide compounds capable of crossing the BBB also in view of the oximes lipophilicity and in particular of the oximes c log P value.

In some oximes of the disclosure, at least 20% of the compound is in the un-protonated form under physiological conditions.

In some embodiments, oximes of the disclosure capable of crossing the BBB have c log P values that range between 0.5-3.0.

In embodiments wherein the oximes comprise labile protective groups, these groups would help increase the BBB permeability of the oxime and can be cleaved readily by a hydrolase such as non-specific esterases within the brain tissue lumen. In those embodiments the propensity towards hydrolysis can be modulated by choosing a particular labile protective group such as an ester. For example, pivaloyl esters are more long-lived than their acetyl and trifluoroacetyl counterparts as they are degraded more slowly by esterases. Alternatively, it is expected that protecting the oxime oxygen with a carbohydrate motif, for example glucose as shown in formula R9d. The example in formula R9d features a peracetylated glucose unit which can be used to introduce modified versions of this sugar into cells due to their high lipophilicity relative to their deacetylated counterparts. It is expected that once inside the lumen, these acetyl groups would get removed once again, for example, by non-specific esterases while the glycosidic linkage joining the sugar to the oxime would get cleaved by glycosyl hydrolases present in the lumen as well. Both of these groups seek to protect and increase the BBB permeability of the parent oxime and once this function has been accomplished, their immediate removal releases the oxime within the brain.

A configuration of oximes capable of crossing the BBB can also be tested with computational models, using molecular dynamics simulations, that are predictive of BBB permeability.

Exemplary oximes capable of crossing the BBB comprising VIIc (VIIc)

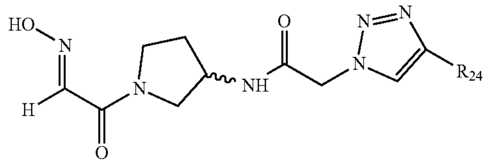

In some embodiments, oximes herein described can be used in a method to reactivate an inactivated acetylcholinesterase in an individual. In particular, in some embodiments, method herein described comprises administering to the individual at least one oxime compound herein for a time and under condition to allow contact between the at least one oxime compound herein described and the inactivated acetylcholinesterase in the individual, the at least one in an amount effective to reactivate the inactivated acetylcholinesterase.

In particular, in embodiments of method to for reactivation of an inhibited AChE in an individual, oximes of the disclosure have a structure configured to have a pKa of a protonated form of the oxime between 7 and 9. In some of those embodiments the oxime herein described provide a direct reactivation at the active site by attacking the adducted serine vs. some type of allosteric inhibition. In some of those embodiments the oximes of the disclosure comprise a DN.

In some embodiments of method for reactivation of an inhibited AChE in an individual, the at least one oxime compound herein described are administered to obtain an oxime concentration in a therapeutically effective amount of the oxime of the disclosure in a protonated form in the individual.

In some embodiments of method for reactivation of an inhibited AChE in an individual, the at least one oxime compound herein described is administered to obtain a total oxime concentration of between 300 and 1200 micromolar in the synaptic cleft to reactivate 10-30% of the AChE enzyme in the individual.

In some embodiments, preferred oximes to be administered to reactive an inhibited AChE comprising (VIIc)

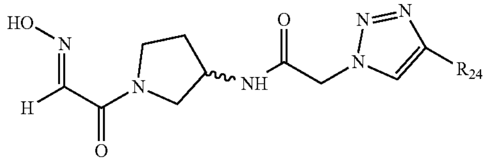

(VIId)

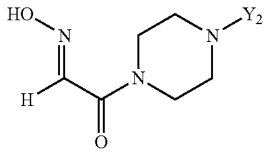

In some embodiments, oximes herein described can be used in a method of treating or preventing a condition of an individual, the condition associated with exposure of the individual to a nerve agent. In particular, in some embodiments the method comprises administering to the individual a therapeutically effective amount of at least one oxime herein described and in particular at least one compound of Formula (III) for a time and under condition to allow contact between the at least one oxime and the nervous system of the individual, and more in particular an acetylcholinesterase bound-neuron of the individual.

The term "nervous system" indicates the part of an individual body that coordinates its voluntary and involuntary actions and transmits signals to and from different parts of its body. Nervous systems in the sense of the disclosure comprises acetylcholine as a neurotransmitter and biochemical mechanisms related to its synthesis and its conversion. In particular the enzyme acetylcholinesterase is part of the acetylcholine biochemical mechanisms which converts acetylcholine into the inactive metabolites choline and acetate. AChE enzyme is abundant in the synaptic cleft, and its role in rapidly clearing free acetylcholine from the synapse is essential for proper muscle function. In embodiments herein described vertebrate species, the nervous system it consists of two main parts, the central nervous system (CNS) and the peripheral nervous system (PNS), wherein the peripheral nervous system (PNS) is the part of the nervous system that consists of the nerves and ganglia on the outside of the brain and spinal cord and is not protected by the blood-brain barrier, and the central nervous system (CNS) is the part of the nervous system consisting of the brain and spinal cord.

The term "treatment" as used herein indicates any activity that is part of a medical care for, or deals with, a condition, medically or surgically.

The term "prevention" as used herein indicates any activity which reduces the burden of mortality or morbidity from a condition in an individual, the condition associated with exposure of the individual to one or more nerve agents. This takes place at primary, secondary and tertiary prevention levels, wherein: a) primary prevention reduces the development of a disease; b) secondary prevention activities are aimed at early disease treatment, thereby increasing opportunities for interventions to prevent progression of the disease and emergence of symptoms; and c) tertiary prevention reduces the negative impact of an already established disease by restoring function and reducing disease-related complications.

The term "condition" as used herein indicates a physical status of the body of an individual (as a whole or as one or more of its parts), that does not conform to a standard physical status associated with a state of complete physical, mental and social well-being for the individual. Conditions herein described include but are not limited disorders and diseases wherein the term "disorder" indicates a condition of the living individual that is associated to a functional abnormality of the body or of any of its parts, and the term "disease" indicates a condition of the living individual that impairs normal functioning of the body or of any of its parts and is typically manifested by distinguishing signs and symptoms.

The term "individual" as used herein in the context of treatment includes a single biological organism having a nervous system, including but not limited to, animals and in particular higher animals and in particular vertebrates such as mammals and in particular human beings In some embodiments, a method of treating and/or preventing a condition of an individual, the condition associated with exposure of the individual to a nerve agent includes administering performed parenterally, intramuscularly, intraperitoneally, subcutaneously, or intravenously. In some of those embodiment, a method of treating or preventing a condition of an individual, herein described comprises injecting the at least one oxime of the disclosure intramuscularly, e.g. into the mid-lateral thigh and/or the arm of the individual.

In some embodiments, a composition including at least one oxime as disclosed herein is formulated in a solution, suspension or aerosol for nasal or mouth inhalation for targeting a brain of a subject directly. In some embodiments, the formulation comprises at least one oxime and a fluid propellant, and optionally one or more excipients and/or adjuvants. The propellant is typically a CFC (chlorofluorocarbons) free propellant, suitably a liquid propellant, and preferably is a HFA (hydrofluoroalkane) propellant, such as HFA-134a (1,1,1,2-tetrafluoroethane) or HFA-227 (1,1,1,2,3,3,3-heptafluoropropane) or a combination thereof.

In some embodiments of the method of treating and/or preventing a condition herein described, at least one oxime of the disclosure is administered at approximately 600 mg of oxime per injection as it is carried as described herein.

In some embodiments of the method of treating and/or preventing a condition of an individual, the administering can be performed by administering at least one oxime herein described alone or in combination with other active agent (such as an antimuscarinics) as a component A and a component B of a combination of active agents to be administered sequentially or simultaneously. The antimuscarinics comprise Atropine, Scopolamine, Pirenzepine, Diphenhydramine, Solifenacin or a combination thereof.

In some embodiments, of the method of treating and/or preventing a condition of an individual, the administering can be performed by administering at least one oxime herein described alone or in combination with other active agent (such as anxiolytics) as a component A and a component B of a combination of active agents to be administered sequentially or simultaneously. The anxiolytics comprise Diazepam, Alprazolam, Clonazepam, Lorazepam, Midazolam or a combination thereof.

In some embodiments, the sequential injection of a component A and a component B can be administered in a given interval of 5 to 30 minutes, preferably 15 minutes, preferably intramuscularly.

In some embodiments of the method of treating and/or preventing a condition of an individual, herein described the at least one oxime of the disclosure can be selected to treatment and/or protection against the nerve agent in the peripheral nervous system (PNS), and/or the central nervous system (CNS). In some of those embodiments, the neutral oxime compounds herein described can be selected to provide protection against nerve agents for both the PNS and the CNS. Accordingly, the at least one oxime of the disclosure targeting the PNS are preferably the oxime capable of inactivating and/or reactivate AChE and do not need to be able to cross the BBB. The at least one oxime of the disclosure targeting the CNS are preferably the oxime capable of inactivating and/or reactivate AChE and further capable of crossing the BBB.

Accordingly, in some embodiments, a method of treating and/or preventing a condition associated with exposure of an individual to a nerve agent comprises administering an oxime herein described is able to reactive the AChE. In some of those embodiments the compounds administered are also capable of crossing the BBB. In some of those embodiments preferred compounds to be administered to an individual to treat and/or prevent a condition associated with exposure of an individual to a nerve agent comprising all structures VIIa-f with sub structures denoted by R and Y groups.

In some embodiments, a method of treating and/or preventing a condition associated with exposure of an individual to a nerve agent comprises administering an oxime herein described is able to inactivate the nerve agent e.g. by decomposition. In particular, oximes capable of inactivating the nerve agent can be used as a prophylactic medicament for the treatment or prevention of nerve agent poisoning. In some of those embodiments preferred compounds to be administered to an individual to treat and/or prevent a condition associated with exposure of an individual to a nerve agent comprise.

In some embodiments, a method of preventing a condition associated with exposure of an individual to a nerve agent comprises administering an oxime to the individual, the oxime capable of inactivating the nerve agent to allow contact of the at least one oxime with the nervous system and/or vascular system of the individual or portions thereof. In some embodiments, the administering can be performed before known or possible contact of the individual with the nerve agent. The term "vascular system", also called the "circulatory system", is made up of the vessels that carry blood and lymph through the body. The arteries and veins carry blood throughout the body, delivering oxygen and nutrients to the body tissues and taking away tissue waste matter.

For example a human can be administered a dosage of an oxime by injection that is long-lived in the blood stream and would in principle provide an immediate level of protection if a nerve agent gains entrance into the subject. Preferably, the half-life of the oxime is longer than 30 minutes, preferably 2 hours, and most preferably 24 hours.

In some embodiments, oximes herein described used for preventing a condition associated with exposure of an individual to a nerve agent can be oximes configured to include moieties and/or substituents that makes them more hydrophilic in order to increase their plasma half-life as will be understood by a skilled person. An exemplary configuration directed to increase plasma half-life of the oxime is obtained by attaching a carbohydrate unit to the drug in free form, not acetylated or modified in any other way, such that the hydroxyl groups of the carbohydrate are comprised in the oxime as alcohols. A modification of this nature provide free circulating oximes in a controlled release manner to protect a human in areas suspected of nerve agent contamination as will be understood by a skilled person.

In some embodiments, method to prevent a condition herein described comprise administering an oxime capable of inactivating one or more nerve agent, possibly also capable of crossing the BBB can be performed in amounts from to 600 to 1000 mg preferably intramuscularly.

In some of those embodiments preferred compounds to be administered to an individual to prevent a condition associated with exposure of an individual to a nerve agent comprising the Rd9 moiety R9d

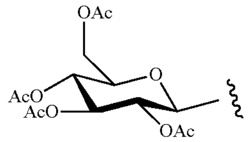

In some embodiments of methods of treating and/or preventing a condition associated with exposure of an individual to a nerve agent herein described comprises administering an oxime herein described having a labile protective group, the oxime administered as a prodrug.

A prodrug as used herein is an oxime compound of the disclosure in which the oxime oxygen is covalently bonded to a carbon atom of another organic moiety that is releasable in vivo to provide the oxime hydroxyl group. The release can be a hydrolysis reaction or a metabolic process in vivo. In some embodiments, an oxime compound can be released from a prodrug in the body's circulatory system, particularly in the blood. In some of those embodiments, the oximes are expected to have an increased BBB permeability profile due to an increased c log P value (e.g. acylation of the oxime moiety) and to be converted into the actual drug after crossing the BBB, by cleaving of the protective labile group or other pro-drug functionality after BBB crossing. Several approaches may be undertaken to provide pro-drugs of the oximes herein described. Preferably, an oxime compound can be released from a prodrug after the prodrug crosses blood brain barrier (BBB) to a brain.

Figure 18:
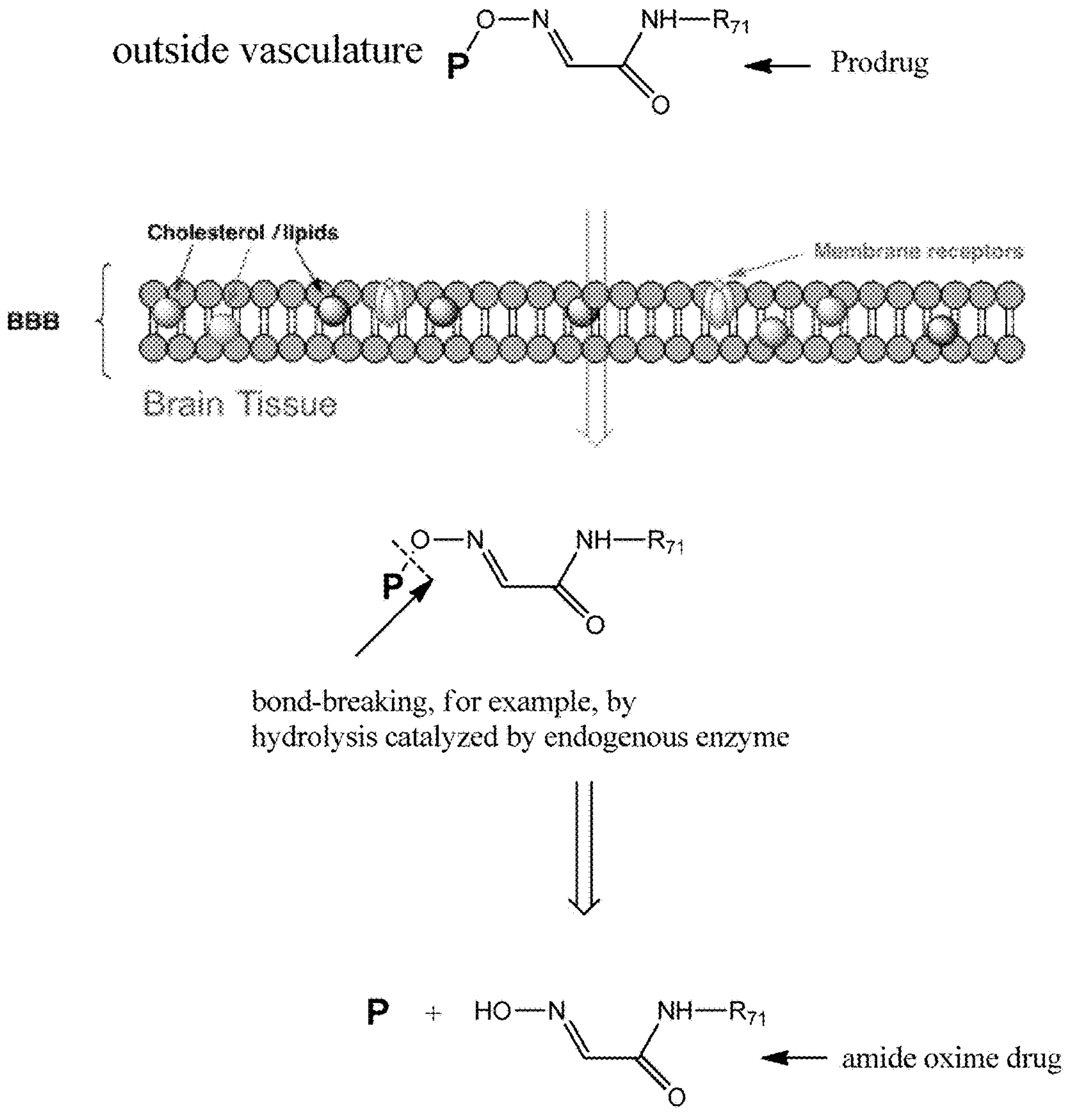
FIG. 18 shows a schematic illustration of a prodrug approach for the delivery of neutral oximes across blood brain barrier to brain tissue with AChE, wherein the "P" in the prodrug is an organic moiety that is releasable in vivo to provide the oxime hydroxyl group and exemplary P includes R9a, R9b, R9c, R9d, R9e and R9f as disclosed herein.
Figure 19:
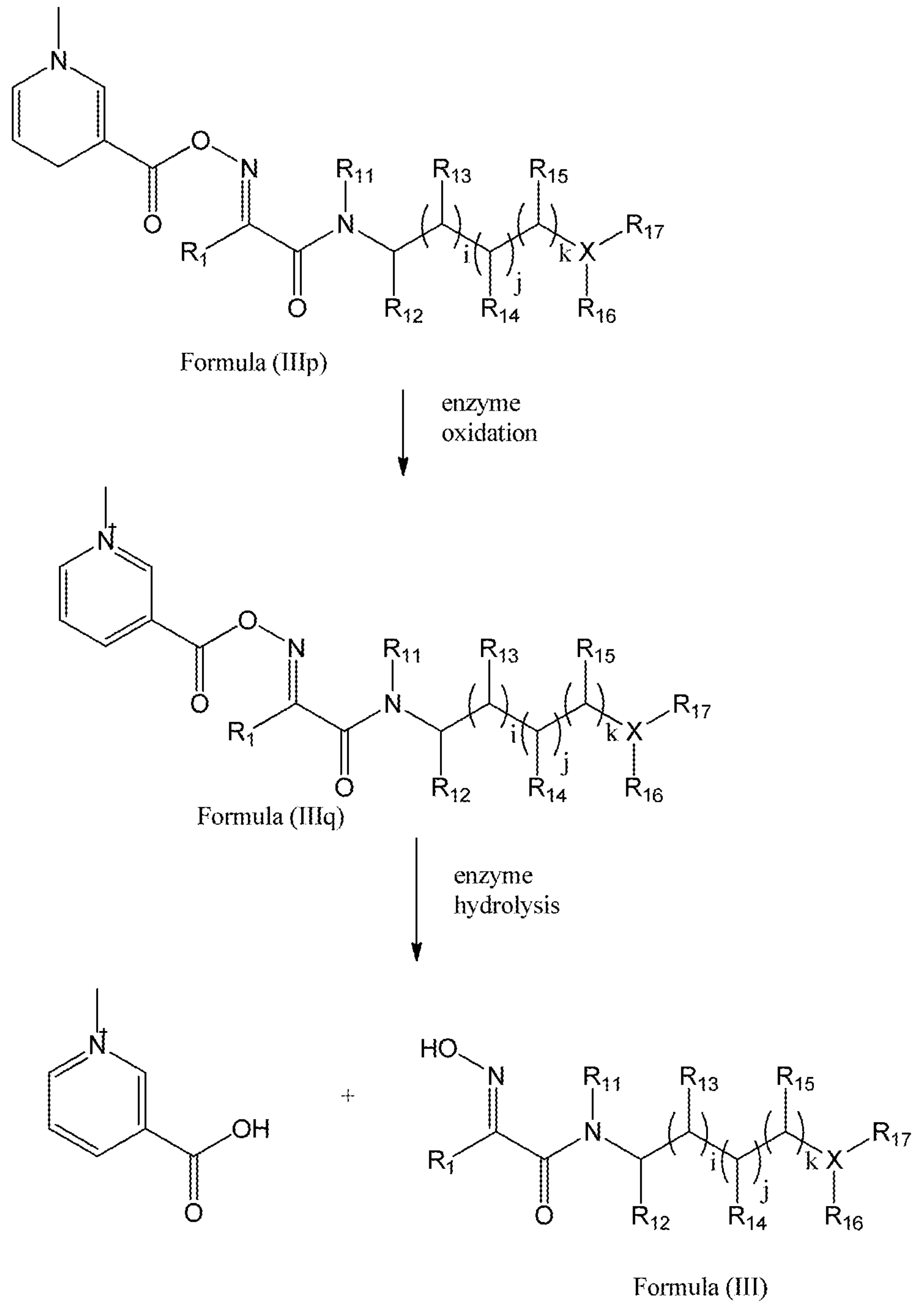
FIG. 19 shows a schematic illustration of an exemplary prodrug of Formula (IIIp) as an ester of oxime Formula (III) which is released by in vivo enzymatic oxidation and hydrolysis via nicotinic acid ester intermediate Formula (IIIq).

A schematic illustration of exemplary approaches to use a prodrug according to some embodiments here described is provided in FIGS. 18 and 19. In particular, an exemplary overall approach is described schematically in FIG. 18, where we have an oxime parent compound that has been modified at its oxime oxygen in order to protect it and increase the overall BBB permeability profile of the drug by increasing its c log P, thus increasing its lipophilicity. Once this pro-drug has crossed the BBB, it is expected to be subjected to the action of a number of metabolizing enzymes such as esterases and glycosyl hydrolases (in the case of the carbohydrate protected oxime). Some of these enzymes such as esterases are non-specific in nature which allows any ester at the oxime oxygen as a pro-drug to be hydrolyzed.

Exemplary oximes comprising a protective labile group that can be administered as a prodrug in methods of treating and/or preventing a condition associated with exposure of an individual to a nerve agent comprise oximes of Formula (VIa)-(VId); (VIIa)-(VIIf), (IIIb1), (IIIc), (IIId) and/or (V) with protecting groups R9a-R9f.

In some embodiments, one or more oximes herein described and related compositions can be used to decontaminate an environment. The term "decontamination" or "decon" as used herein refers to a process of removing, neutralizing or decomposing a nerve agent that are present in the environment. An "environment" as used herein indicates the complex of physical, chemical, and biotic factors (as climate, soil, and living things) that act upon an organism or parts thereof an ecological community. Environments comprise individuals or other organisms or portions therefore (e.g. organs, tissues or cells) as well as physical objects Exemplary physical objects includes protective clothing, respiratory equipment, tools, automobile and building. In an environment, one or more nerve agent can be present on skin of an individual or on a surface of a physical object or permeate at least in part the physical object and/or the individual.

In some embodiments, oximes as disclosed herein can be used for decontamination of nerve agents. The decontamination profile of the oxime compounds include those that lack DN or any H-bonding moieties for interaction with any enzymes and their capability to destroy the nerve agent, such as by decomposition.

In embodiments, wherein decontamination is desired, an oxime herein described capable of inactivating one or more nerve agent is typically selected be selected to also have, 1) high efficiency and rate of reaction of the oxime with one or more nerve agents, 2) non-toxicity of the materials after the agent destruction, and/or 3) eco-friendliness, such as being non-persistent in the environment. Accordingly, in some embodiments, oximes herein described used for decontamination are not capable of crossing the BBB and/or of providing AChE reactivation. Accordingly, preferred compounds for decontamination are oximes capable of inactivating a free nerve agent faster than the ability of the AChE to bind the nerve agent. this characteristic was used as a screening tool to identify potential candidates for decontamination technologies (Yang et al 1992, Singh et al 2010 and Ajami et al, 2013).

In some embodiments, the method of decontaminating an environment can be performed by contacting the environment with one or more oximes herein described prior to the entrance into the environment where the use of nerve agents is suspected. Preferably, the half-life of the oxime is longer than 30 minutes, preferably 2 hours, and most preferably 24 hours.

In method to decontaminate herein described one or more oxime can be contacted with an environment to be decontaminated in an amount depending on the concentration of the contaminant.

In some embodiments, one or more oximes herein described are comprised in a composition together with a suitable vehicle. The term "vehicle" as used herein indicates any of various media acting usually as solvents, carriers, binders or diluents for the oximes that are comprised in the composition as an active ingredient. In particular, the composition including the one or more oximes can be used in one of the methods or systems herein described.

In embodiments, one or more oximes herein described are comprised in a composition further comprising an antagonist of a muscarinic acetylcholine receptor, preferably, the antagonist of a muscarinic acetylcholine receptor comprises atropine.

In embodiments, wherein compositions comprising one or more oximes are formulated for decontamination, the related a formulation can comprise the one or more oximes in a carrier solution that can be a buffer, preferably organic or phosphate-based buffer, that has a pH value that allows the oxime to perform decontamination as optimally as possible base on the three characteristics as described herein.

In some embodiments, the composition for decontamination comprises at least one oxime compound further comprising at least one metal ion selected from the group consisting of $Cu^{2+}$, $Pt^{2+}$, $Pd^{2+}$, $Zn^{2+}$, $Y^{3+}$, $Sc^{3+}$, $Ce^{3+}$, $La^{3+}$, $Pr^{3+}$, $Nd^{3+}$, $Sm^{3+}$, $Eu^{3+}$, $Gd^{3+}$, $Tb^{3+}$, $Dy^{3+}$, $Ho^{3+}$, $Er^{3+}$, $Tm^{3+}$, $Yb^{3+}$, and combinations thereof. In some embodiments, the concentration of the at least one metal ion is 0.01 to 0.50 mM, preferably 0.05-0.20 mM.

In some embodiment, in compositions for decontamination, the at least one metal ion is present in a solution further comprising a solvent selected from the group consisting of methanol, ethanol, n-propanol, iso-propanol, n-butanol, 2-butanol, methoxyethanol, and combinations thereof. In some embodiments, the solution further comprise corresponding sodium or potassium alkoxide of methanol, ethanol, n-propanol, iso-propanol, n-butanol, 2-butanol, methoxyethanol, and combinations thereof.

In some further embodiments, in compositions for decontamination, the molar ratio of the alkoxide ion to the at least one metal ion selected from the group consisting of $Cu^{2+}$, $Pt^{2+}$, $Pd^{2+}$, $Zn^{2+}$, $Y^{3+}$, $Sc^{3+}$, $Ce^{3+}$, $La^{3+}$, $Pr^{3+}$, $Nd^{3+}$, $Sm^{3+}$, $Eu^{3+}$, $Gd^{3+}$, $Tb^{3+}$, $Dy^{3+}$, $Ho^{3+}$, $Er^{3+}$, $Tm^{3+}$, $Yb^{3+}$, and combinations thereof, is about 0.10 to 3.0, preferably 1.0 to 2.0.

In some embodiments, a method for decontamination of a surface or area having a nerve agent comprises providing a composition having a water-based carrier vehicle, preferably an aqueous buffer at a suitable pH, preferably in a range between pH 7-11, wherein the oxime would be suspended or solubilized. The composition of oxime solution or suspension would then be sprayed on a contaminated surface or area and as the oxime comes into contact with the nerve agent, it will catalyze the hydrolysis of the nerve agent almost immediately.

In embodiments of methods for decontamination herein described, the rate of the hydrolysis reaction is dependent on the temperature of the environment in which the contaminated surface or area is located. For example, the rate of hydrolysis will be higher in certain hot areas, e.g. desert. On the other, in the winter season, the rate of hydrolysis will be slower than in the summer.

In some embodiments, the compositions for decontamination, is adjusted according to the specific environmental condition of the contaminated surface or area. In some situations, an additional ingredient such as diethylene glycol can be added to compensate extreme environmental conditional to avoid freezing or evaporation of the oxime composition. The diethylene can be present in 1 to 50% by weight, preferably 5 to 10% by weight.

In some embodiments, the oximes herein described to be used in a method herein described can be included in pharmaceutical compositions together with an excipient or diluent. In particular, in some embodiments, disclosed are pharmaceutical compositions which contain at least one oxime as herein described, in combination with one or more compatible and pharmaceutically acceptable vehicles, and in particular with pharmaceutically acceptable diluents or excipients. In those pharmaceutical compositions the oxime can be administered as an active ingredient for treatment or prevention of a condition in an individual.

As used herein, the term "pharmaceutically acceptable" means not biologically or otherwise undesirable, in that it can be administered to a subject without excessive toxicity, irritation, or allergic response, and does not cause unacceptable biological effects or interact in a deleterious manner with any of the other components of the composition in which it is contained.

The term "excipient" as used herein indicates an inactive substance used as a carrier for the active ingredients of a medication. Suitable excipients for the pharmaceutical compositions herein described include any substance that enhances the ability of the body of an individual to absorb one or more oximes herein described or combinations thereof. Suitable excipients also include any substance that can be used to bulk up formulations with the oximes or combinations thereof, to allow for convenient and accurate dosage. In addition to their use in the single-dosage quantity, excipients can be used in the manufacturing process to aid in the handling of the oximes or combinations thereof concerned. Depending on the route of administration, and form of medication, different excipients can be used. Exemplary excipients include, but are not limited to, antiadherents, binders, coatings, disintegrants, fillers, flavors (such as sweeteners) and colors, glidants, lubricants, preservatives, sorbents.

The term "diluent" as used herein indicates a diluting agent which is issued to dilute or carry an active ingredient of a composition. Suitable diluents include any substance that can decrease the viscosity of a medicinal preparation.

In some embodiments, a pharmaceutical composition to treat a condition associated with exposure of an individual with a nerve agent includes at least one oxime compound of Formula (III) in a therapeutically effective amount and a pharmaceutically acceptable vehicle. In some embodiments, 50-100 mg of the at least one oxime compound of Formula (III) are formulated in a pyrogen-free aqueous solution. In some embodiment, 600 mg of the at least one oxime compound of Formula (III) are dissolved or suspended in 2 mL of sterile, pyrogen-free solution containing 40 mg benzyl alcohol, 22.5 mg glycine, and Water for Injection, the pH is adjusted with hydrochloric acid to a pH range which is 2.0 to 3.0, as component A.

In some embodiment, the pharmaceutical composition to treat a condition associated with exposure of an individual with a nerve agent can further include 2.1 mg of atropine in 0.7 mL of sterile, pyrogen-free solution containing 12.47 mg glycerin and not more than 2.8 mg phenol, citrate buffer, and Water for Injection, the pH range is 4.0-5.0, as component B.

In some embodiments, the oximes herein described can be provided in the form of kits of parts. In a kit of parts, the one or more oximes can be provided in various combinations one with another. In some embodiments, the kits can also comprise one or more oximes of the disclosure in combination with one or more active agent for treatment of a condition associated to exposure of an individual to a nerve agent (e.g. atropine). In some embodiments, the kits can also comprise one or more oximes of the disclosure in combination with one or more active agent for inactivating a nerve agent and/or decontaminate an environment. In the kits of parts the components can be comprised in the kit independently possibly included in a composition together with suitable vehicle carrier or auxiliary agents.

Additional components can also be included and comprise, reference standards, and additional components identifiable by a skilled person upon reading of the present disclosure.

In the kit of parts herein disclosed, the components of the kit can be provided, with suitable instructions and other necessary reagents, in order to perform the methods here disclosed. In some embodiments, the kit can contain the compositions in separate containers. Instructions, for example written or audio instructions, on paper or electronic support such as tapes or CD-ROMs, for carrying out the assay, can also be included in the kit. The kit can also contain, depending on the particular method used, other packaged reagents and materials.

In embodiments herein described wherein the nerve agent has formula (IX) preferred oximes comprise oximes of formula (IIIa)

Further properties and characteristics of the present disclosure will become more apparent hereinafter from the following detailed disclosure by way or illustration only with reference to an experimental section.

EXAMPLES

The compounds, materials, compositions, methods system herein described are further illustrated in the following examples, which are provided by way of illustration and are not intended to be limiting.

In particular, the following examples illustrate exemplary compounds and related methods and systems in accordance with the disclosure. A person skilled in the art will appreciate the applicability and the necessary modifications to adapt the features described in detail in the present section, to additional compounds, compositions, methods and systems according to embodiments of the present disclosure.

In the examples the following materials and methods can be used.

Example 1: Synthesis of Neutral Oximes

The following oximes compounds were synthesized

Compound CV9-067

CV-067

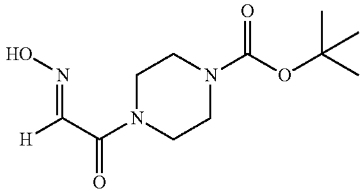

In a 25 mL round bottom flask equipped with a stir bar, 1-BOC-piperazine (200 mg, 1.07 mmol) and ethyl glyoxylate oxime (125 mg, 1.07 mmol) were dissolved in EtOH (10 mL). The mixture was heated to 65° C. and stirred vigorously overnight. The following day, the mixture was cooled to ambient temperature, and the ethanol removed under reduced pressure and at 60° C. to yield a yellow oil that was purified by flash column chromatography on silica gel (hexane→EtOAc) to yield the title oxime CV9-067 as a white solid (159 mg, 58%). Rf=0.25 (1:1 EtOAc/hexane, silica gel TLC); 1H NMR (600 MHz) DMSO-Δ6; d 1.40 (s, 9H), 3.28-3.31 (m, 4H), 3.33-3.37 (m, 4H), 8.12 (s, 1H), 11.4 (s, 1H).

CV9-085

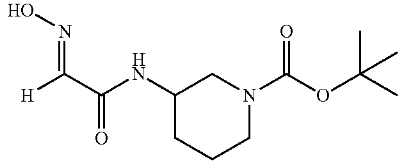

In a 25 mL round bottom flask equipped with a stir bar, 1-BOC-3-aminopiperidine (100 mg, 0.45 mmol) and ethyl glyoxylate oxime (53 mg, 0.45 mmol) were dissolved in EtOH (10 mL). The mixture was heated to 65° C. and stirred vigorously overnight. The following day, the mixture was cooled to ambient temperature, and the ethanol removed under reduced pressure and at 60° C. to yield a yellow oil that was purified by flash column chromatography on silica gel (hexane→EtOAc) to yield the title oxime CV9-085 as a colorless oil (63 mg, 52%). Rf=0.22 (1:1 EtOAc/hexane); 1H NMR (600 MHz) DMSO-Δ6; d 1.41 (9H), 1.88-1.93 (m, 2H), 1.95-1.99 (m, 2H), 3.51-3.66 (m, 2H), 3.69-3.80 (m, 3H), 7.89 (br s, 1H), 8.43 (s, 1H), 11.9 (br s, 1H).

Compound CV9-086

CV9-086

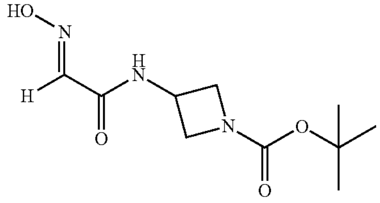

In a 25 mL round bottom flask equipped with a stir bar, 1-BOC-3-aminoazetidine (150 mg, 0.87 mmol) and ethyl glyoxylate oxime (102 mg, 0.87 mmol) were dissolved in EtOH (10 mL). The mixture was heated to 65° C. and stirred vigorously overnight. The following day, the mixture was cooled to ambient temperature, and the ethanol removed under reduced pressure and at 60° C. to yield a yellow oil that was purified by flash column chromatography on silica gel (hexane→EtOAc) to yield the title oxime CV9-086 as a white solid (121 mg, 57%). Rf=0.25 (1:1 EtOAc/hexane); 1H NMR (600 MHz) DMSO-Δ6; d 1.44 (9H), 3.65-3.90 (m, 4H), 4.12-4.17 (m, 1H), 7.91 (br s, 1H), 8.42 (s, 1H), 12.9 (br s, 1H).

Compound CV9-087

CV9-087

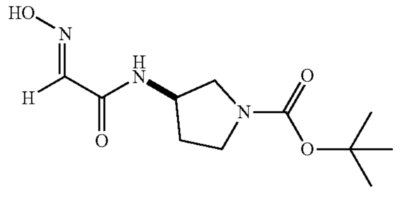

In a 25 mL round bottom flask equipped with a stir bar, (R)-(+)-1-BOC-3-aminopyrrolidine (150 mg, 0.81 mmol) and ethyl glyoxylate oxime (95 mg, 0.81 mmol) were dissolved in EtOH (10 mL). The mixture was heated to 65° C. and stirred vigorously overnight. The following day, the mixture was cooled to ambient temperature, and the ethanol removed under reduced pressure and at 60° C. to yield a yellow oil that was purified by flash column chromatography on silica gel (hexane→EtOAc) to yield the title oxime CV9-087 as a white powder (131 mg, 63%). Rf=0.27 (1:1 EtOAc/hexane); 1H NMR (600 MHz) DMSO-Δ6; d 1.42 (9H), 1.97-2.15 (m, 2H), 3.44-3.50 (m, 2H), 3.68-3.94 (m, 2H), 3.99-4.05 (m, 1H), 7.73 (br s, 1H), 8.40 (s, 1H), 12.4 (br s, 1H).

Example 2: AChE-Oxime Interaction

An exemplary compound herein described and related interaction with acetylcholinesterase is illustrated by the schematics in FIG. 1.

In particular, FIG. 1 panel A shows an oxime compound in which an amide nitrogen (AN) of a 2-hydroxyimino acetamido moiety is linked to a distal basic nitrogen (DN) by a bridging unit. The bridging unit can be an aliphatic moiety and could include a ring structure. The ring structure can be a aliphatic cyclic or aromatic moiety optionally containing a least one heteroatom. The ring AN, DN or both AN DN nitrogen atoms could be part of the ring structure form in part by the bridging unit.

In the illustration of Panel A of FIG. 1, the cyclic framework constrains the oxime compound configuration for fitting into the active site of the AChE enzyme. The linear methylene bridging unit contributes to the proper positioning of the distal nitrogen for effective electrostatic interaction with the Asp 74 carboxylate group and the side chains of Tyr 124 and Trp 286 of the AChE enzyme peripheral anionic binding site.

FIG. 1 panel B illustrates the resulting oxime compound of FIG. 1 panel A fitting into an active site of the AChE enzyme. The positively charged the protonated DN under physiological pH provides a favorable electrostatic interaction with a negatively charged carboxylate group of the AChE enzyme. In this complex, an active oxime compound would have the oxime hydroxyl group position for chemical interaction with a bound nerve agent for reactivation.

As shown in FIG. 1 the activity of the oxime compound is related to a multitude of variables, including the size and rigidity of the cyclic framework, the number of the linear methylene bridging unit, the nature of the R51 and R52 groups such as charge, size and polarity or aromaticity. In the exemplary compound of FIG. 1, the hydrogen on the oxime carbon can be replaced by a methyl group.

Example 3: Computational Binding Free Energy Calculations for AChE and Oximes Computational docking of exemplary compounds was performed for the following inactivated structures of AChE: a mouse AChE adducted with sarin alone (PDBID:2y2v), a mouse AChE adducted with sarin and with Hi6 removed prior to calculations (PDBID:2WHP), a human AChE adducted with sarin, and a model human AChE adducted with sarin. The last structure of a model human AChE adducted with sarin was derived from a soman adducted human AChE protein. Each protein structure presents differences in the conformations of key active site residues that can affect the docking calculations. Based on the structures in the docking calculations, a consensus in binding modes among the tested ligands was determined.

Known oxime reactivator compounds (2-PAM, HI-6, and MMB4) along with herein disclosed oxime compounds are used in the docking calculations. In addition to the docking calculations a MM/GBSA free energy rescoring algorithm was implemented to improve the odds of finding the most relevant binding pose for each ligand (Zhang et al. 2015). Three criteria were imposed in the calculation to rank order the ligand binding poses, namely phosphorous-oxime oxygen distance less than 7 (+/−1) Å, a ligand efficiency defined as the binding free energy divided by the number of heavy atoms in the molecule of at least −1.0 (+/−0.5) kcal/mole binding free energy per heavy atom, and angular constraint to select for poses that provided for an inline attack vector defined as the oxime oxygen approaches the phosphorous atom at an angle of 180 (+/−20) degrees relative to the Ser203 hydroxyl oxygen atom. Free energy binding values are normalized due to the additive nature of the calculations. That is, on average a larger molecule will in general have a more favorable binding energy just because it contains more atoms.

Table 1. below summarizes the normalized free energy binding results for selected examples of oxime scaffolds as well as control oximes. Compounds that achieve all three criteria described above are annotated with three asterisks (***). Deviations from the ideal are shown with one or two asterisks. Results for 2-PAM, HI-6, and H1ö7 were included as positive controls for the binding calculations and the structures are not highlighted. The calculations show that the binding pose is nearly identical to experimentally determined conformation in the case of HI-6 in the 2WHP protein and that 2-PAM and H1ö7 have energetically favorable binding in the several of the proteins structures. The baseline for binding is based upon the results in the controls, that is, binding of new compounds should be equal to or better than the ligand efficiencies and poses of the control ligands (e.g. HI-6 Ligand efficiency=−0.8). The Adj notation means that the compound bound most favorably in a conformation that was rotated 90 degrees from the proper inline orientation described above. A zero value means no poses were found that met the three criteria or bound favorably in the adjacent conformation.

TABLE 1
Normalized Free Energy Binding Values and Oxime Structures
| Label | Ligand Efficiency hAChEXtal | 2y2v | 2whp | Human Model | Structure |
|---|---|---|---|---|---|
| CV9-067 | 0 | −1.3*** | 0 | −1.0*** | 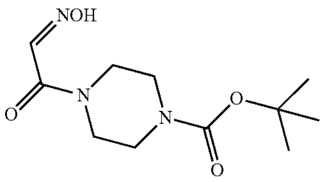 (†) |
| CV9-083 | −0.8*** | 0 | 0 | 0 | 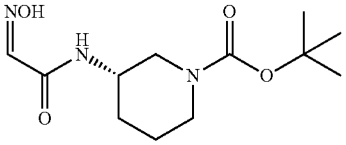 # |
| CV9-084 | 0 | 0 | 0 | 0 | 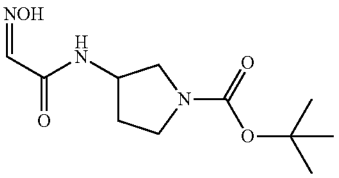 # |
| CV9-087 | Adj | Adj | 0 | −0.4** | # 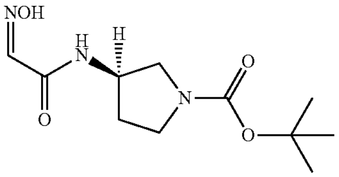 |
| CV9-086 | 0 | 0 | 0 | 0 | # 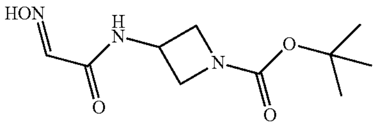 |
| CV9-165F | 0 | 0 | −1.0*** | 0 | (†) 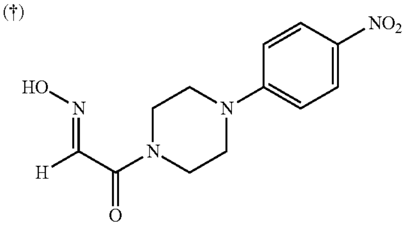 |
| CV10-042B | 0 | 0 | 0 | 0 | 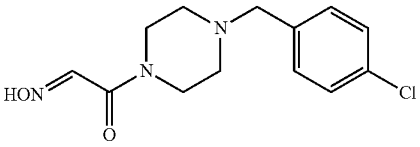 (†) |

TABLE 1-continued

Normalized Free Energy Binding Values and Oxime Structures

| Label | Ligand Efficiency hAChEXtal | 2y2v | 2whp | Human Model | Structure |
|---|---|---|---|---|---|
| CV10-049A | 0 | 0 | −1.48*** | 0 | 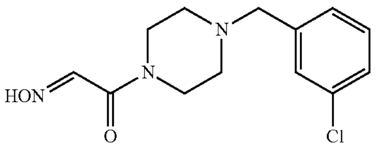 (†) |
| CV10-049B | −1.4*** | −1.1*** | 0 | −1.83*** | 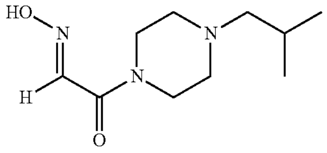 (†) |
| CV10-049E | −1.3*** | −1.2*** | 0 | 0 | 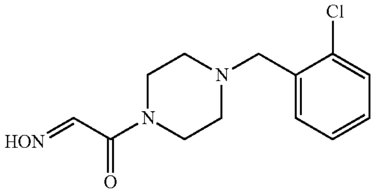 (†) |
| 2PAM | −1.1** | 0 | Adj | 0 | 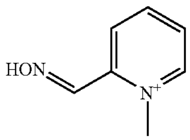 |
| Hlö-7 | −0.6** | 0 | 0 | −0.5** | 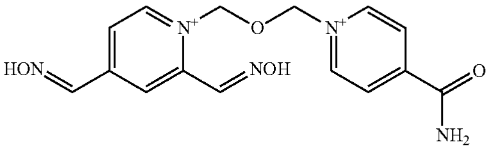 |
| Hi-6 | Adj | Adj | −0.8 | Adj | 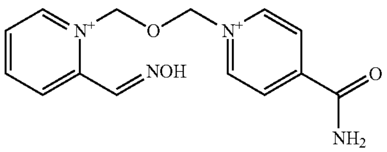 |

Compounds annotated with pound (#), are based on oximes having scaffold with the t-butyl carbamate synthetic handle distal to the oxime nitrogen. These compounds show which scaffold may have the highest probability of binding. Four of these compounds do not show promising binding characteristics in the calculations when compared to the positive controls. The exception is CV9-067 which shows inline attack poses with significant binding energies for two separate AChE crystal structures. Data for CV9-067 analogs are shown in Table 1 and are annotated as CV10-049A, CV10-049E, and CV10-042B from oxime molecules having piperazine scaffold. In contrast to other scaffolds, the piperazine scaffold annotated with dagger (t) does show promise in that all three compounds bind with an inline attack mode in at least one protein structure.

Example 4: Compound CV9-118 Binding a Sarin-Adducted Mouse AChE (2 whp)

Figure 2:
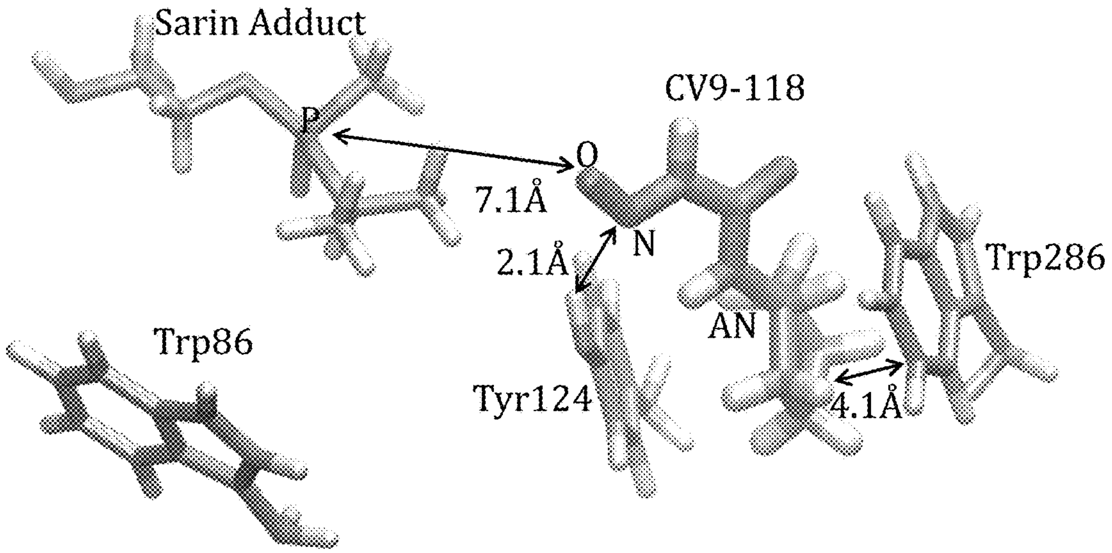
FIG. 2 shows a schematic representation of a binding pose of an exemplary compound CV9-118 herein described in the active site mouse AChE (2y2v)

FIG. 2 shows the most favorable pose of CV9-118 docked into the active site of the mouse AChE (2WHP). Notable is the P—O, phosphorus to oxime oxygen, distance of 7.1 Å. Increased hydrophobic interactions between the side chains of Tyr124 and Trp286 and the oxime cyclopentyl ring have drawn the oxime further from the sarin adduct. There is a 2.1 Å hydrogen bond between the oxime nitrogen atom and the hydroxyl group of Tyr124 as indicated. Also important is the rotation of the sarin isopropyl chain towards Tyr124 and CV9-118.

The conformation of the protein and sarin adduct provided in the illustration of FIG. 2 is proposed to be the canonical Michaelis-Menten binding site known to a person skilled in the art. In the illustration of FIG. 2 the conformation protein-sarin adduct represents an initial step in the progression towards the inline attack required for AChE reactivation.

Example 5: Compound CV9-118 Binding in a Sarin-Adducted Human AChE

Figure 3:
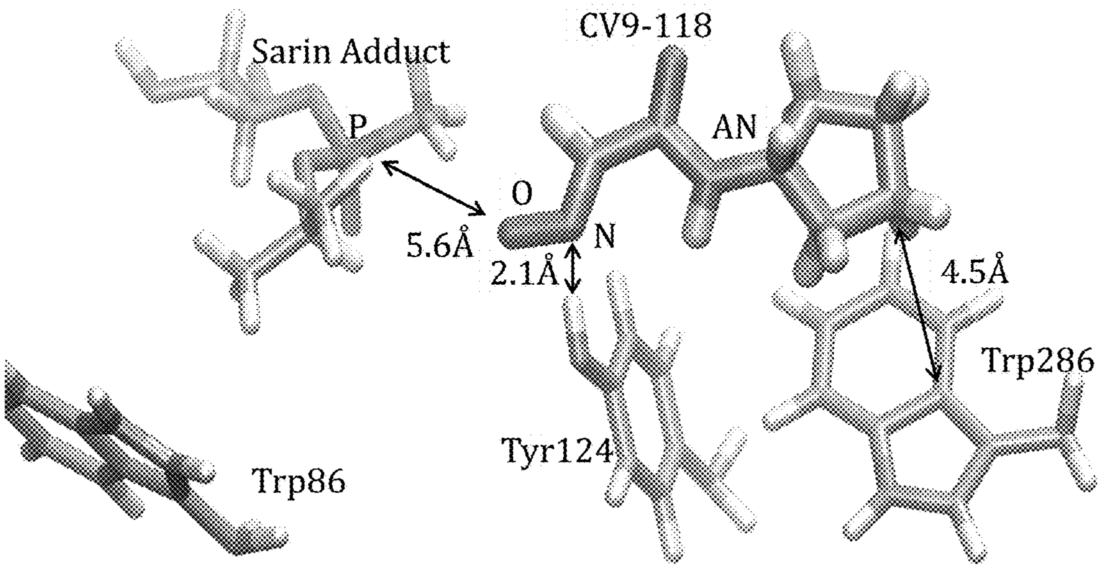
FIG. 3 shows a schematic representation of a binding pose of an exemplary compound herein described in the active site of human AChE.
Figure 4:
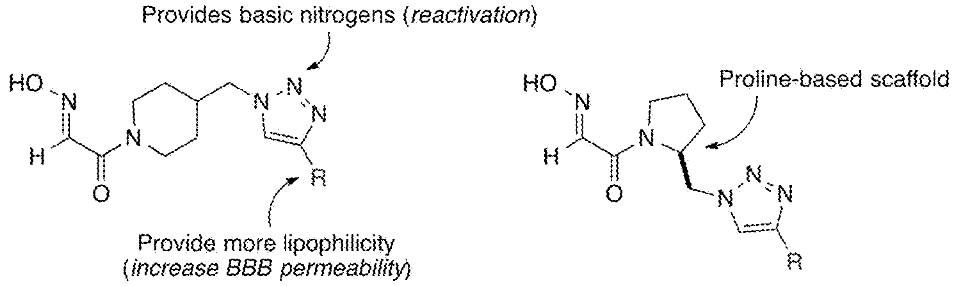
FIG. 4 shows the general structures and characteristics of the two triazole-based compounds of in which the basic nitrogen for binding the active site and the lipophilic R group on the triazole ring providing BBB permeability function and the piperidinyl and prolinyl groups of the respective classes of compound constraining molecules for reactivation of phosphonylated AChE enzymes.

An exemplary schematic of the binding pose of compound CV9-118 in the sarin adducted mouse structure is shown in FIG. 3. The P-Oxime distance is 5.6 Å, which is less than what has been posited for the proposed Michaelis-Menton binding site. Non-polar interactions are found between the oxime pentyl ring and carbons of the indole ring of Trp286. A short hydrogen bond is present between the hydroxyl oxygen of the Tyr124 sidechain and oxime nitrogen atom in CV9-118. The sarin isopropyl sidechain is rotated slightly towards Trp86 and away from the oxime allowing for an inline approach of the oxime oxygen atom towards the sarin phosphorous atom. The conformation of the examplary illustration of FIG. 3 is expected to be the penultimate step before an ecounter complex forms which requires a P-oxime oxygen distance of less than 3.5 Å

Based on the current modeling, the aliphatic ring for example, of 4 to 8 member aliphatic ring in between and/or including AN and DN will favor an inline attack conformation.

Based on the current literature and crystal structures of sarin-adducted mouse AChE, P-oxime oxygen distances of a range between 3 to 8 Å is expected to be indicative of activity all other factors being equal.

Favorable interactions between the DN and Trp286 side chain should be within 5.4 Å.

Example 6: Synthesis of a DN Restrained Oxime 5

An example of DN restrained oxime herein described is provided by compound 5

5

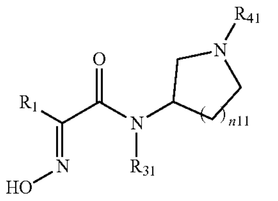

wherein

R1 is H or $CH_3$, R2 and R4 are independently H, a linear or branched alkyl chains, possessing alkenyl, alkynyl, aryl, arylalkyl or alkylaryl carbon atoms or a heteroatom having equal to or less than 18 carbon atoms.

and n11=0, 1, 2, or 3.

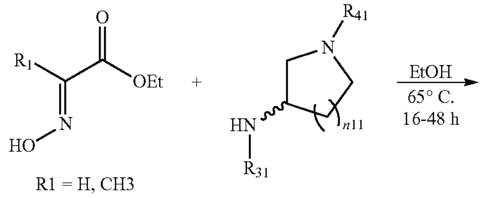

-continued

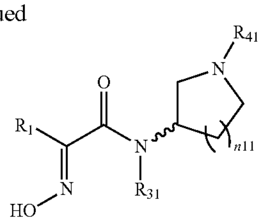

n11 = 0, 1, 2, or 3

5

To synthesize compound 5, the 1-protected 3-aminopyrrolidine (3 mmol) was added to a solution of ethyl glyoxylate oxime (3 mmol) in ethanol (10-20 mL) at ambient temperature. The resulting mixture was heated to 65° C. Depending on the nature of the amine used for the reaction, reaction times range anywhere between 16-48 hours at 65° C. Yields are typically between 50-70% with the remaining material being unreacted ethyl glyoxylate oxime. Depending on the nature of the 1-protected 3-aminopyrrolidine starting material, the product may precipitate during the reaction or would require synthesis by flash chromatography (hexane→EtOAc). The reaction can be monitored by TLC (1:1 EtOAc/hexane) using UV and the disappearance of the ethyl glyoxylate oxime ($R_f$=0.6).

Example 7: Synthesis of AN Restrained Oxime 6

An example of AN restrained oxime herein described is provided by compound 6

6

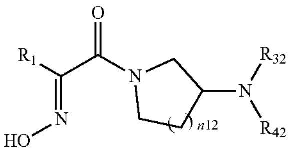

wherein R1=H, $CH_3$; R31, R42=alkyl groups ranging from C1-C18 and n12=0, 1, 2, or 3.

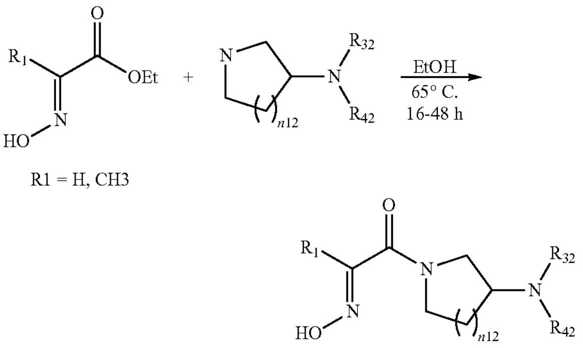

n12 = 0, 1, 2, or 3

6

The 3-protected 1-aminopyrrolidine (3 mmol) was added to a solution of ethyl glyoxylate oxime (3 mmol) in ethanol (10-20 mL) at ambient temperature. The resulting mixture was heated to 65° C. Depending on the nature of the amine used for the reaction, reaction times range anywhere between 16-48 hours at 65° C. Yields are typically between 50-70% with the remaining material being unreacted ethyl glyoxylate oxime. Depending on the nature of the 1-protected 3-aminopyrrolidine starting material, the product may precipitate during the reaction or would require synthesis by flash chromatography (hexane 4 EtOAc). The reaction can be monitored by TLC (1:1 EtOAc/hexane) using UV and the disappearance of the ethyl glyoxylate oxime ($R_f$=0.6).

Example 8: Synthesis of DN Restrained Oxime 7

An example of DN restrained oxime herein described is provided by compound 7

7

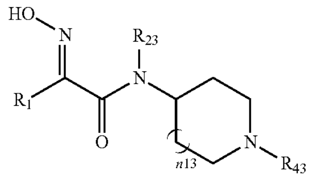

n13 = 0, 1, 2, or 3 wherein R1=H, $CH_3$; R23, R43=a substituted or unsubstituted branched, straight-chain, a heterocyclic, or cyclic alkyl group having 1-18 carbon atoms, an aromatic or a heteroaromatic aryl group including phenyl, biphenyl, benzyl, pyridyl, naphthyl, polynuclear aromatic; and n13=0, 1, 2, or 3.

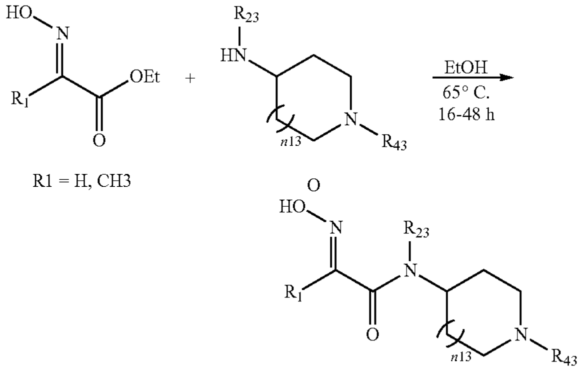

n13 = 0, 1, 2, or 3
7

The 1-protected 4-aminocyclic amine (3 mmol) was added to a solution of ethyl glyoxylate oxime (3 mmol) in ethanol (10-20 mL) at ambient temperature. The resulting mixture was heated to 65° C. Depending on the nature of the amine used for the reaction, reaction times range anywhere between 16-48 hours at 65° C. Yields are typically between 50-70% with the remaining material being unreacted ethyl glyoxylate oxime. Depending on the nature of the 1-protected 3-aminopyrrolidine starting material, the product may precipitate during the reaction or would require synthesis by flash chromatography (hexane 4 EtOAc). The reaction can be monitored by TLC (1:1 EtOAc/hexane) using UV and the disappearance of the ethyl glyoxylate oxime ($R_f$=0.6).

Example 9: Synthesis of DN Restrained Oxime 8

An example of DN restrained oxime herein described is provided by compound 8

8

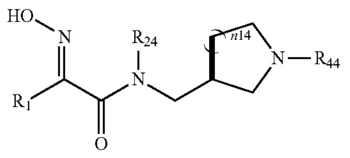

n14 = 0, 1, 2, or 3 wherein R1=H, $CH_3$; R24, R44=a substituted or unsubstituted branched, straight-chain, a heterocyclic, or cyclic alkyl group having 1-18 carbon atoms, an aromatic or a heteroaromatic aryl group including phenyl, biphenyl, benzyl, pyridyl, naphthyl, polynuclear aromatic; and n14=0, 1, 2, or 3.

To synthesize compound 8, the amine (1 mmol) was added to a solution of ethyl glyoxylate oxime (1 mmol) in EtOH (10 mL) in a 50 mL round-bottomed flask equipped with a stir bar. The resulting mixture was heated at 65° C. overnight. The following day, the mixture was cooled to ambient temperature and the EtOH removed under vacuum at 65° C. The resulting residue was purified by silica gel column chromatography (hexane 4 EtOAc) to afford the title compound described by the structure 8. Most of the products have an Rf value between 0.2-0.8 at 1:1 EtOAc/hexane, so the chromatography linearity (hexane 4 EtOAc) is optimal for the recovery of these products from the reaction mixture.

Example 10: Synthesis of AN Restrained Oxime 9

An example of DN restrained oxime herein described is provided by compound 9

9

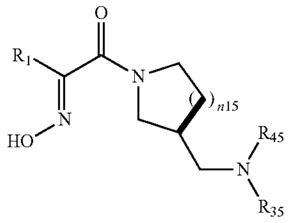

n15 = 0, 1, 2, or 3 wherein R1=H, $CH_3$; R35, R45=a substituted or unsubstituted branched, straight-chain, a heterocyclic, or cyclic alkyl group having 1-18 carbon atoms, an aromatic or a heteroaromatic aryl group including phenyl, biphenyl, benzyl, pyridyl, naphthyl, polynuclear aromatic; and n15=0, 1, 2, or 3.

To synthesize compound 9, the amine (1 mmol) was added to a solution of ethyl glyoxylate oxime (1 mmol) in EtOH (10 mL) in a 50 mL round-bottomed flask equipped with a stir bar. The resulting mixture was heated at 65° C. overnight. The following day, the mixture was cooled to ambient temperature and the EtOH removed under vacuum at 65° C. The reuslting residue was purified by silica gel column chromatography (hexane 4 EtOAc) to afford the title compound described by the structure 9. Most of the products have an Rf value between 0.2-0.8 at 1:1 EtOAc/hexane, so the chromatography linearity (hexane 4 EtOAc) is optimal for the recovery of these products from the reaction mixture.

Example 11: Synthesis of AN Restrained Oxime 10

An example of AN restrained oxime herein described is provided by compound 10

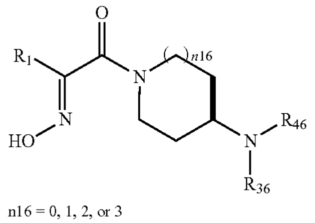

wherein R1=H, $CH_3$; R36, R46=a substituted or unsubstituted branched, straight-chain, a heterocyclic, or cyclic alkyl group having 1-18 carbon atoms, an aromatic or a heteroaromatic aryl group including phenyl, biphenyl, benzyl, pyridyl, naphthyl, polynuclear aromatic; and n16=0, 1, 2, or 3.

The 4-aminoprotected cyclic amine (3 mmol) was added to a solution of ethyl glyoxylate oxime (3 mmol) in ethanol (10-20 mL) at ambient temperature. The resulting mixture was heated to 65° C. Depending on the nature of the amine used for the reaction, reaction times range anywhere between 16-48 hours at 65° C. Yields are typically between 50-70% with the remaining material being unreacted ethyl glyoxylate oxime. Depending on the nature of the 1-protected 3-aminopyrrolidine starting material, the product may precipitate during the reaction or would require synthesis by flash chromatography (hexane 4 EtOAc). The reaction can be monitored by TLC (1:1 EtOAc/hexane) using UV and the disappearance of the ethyl glyoxylate oxime ($R_f$=0.6).

Example 12: Synthesis of Combinatorial Libraries of Formula 5-10

Figure 20:
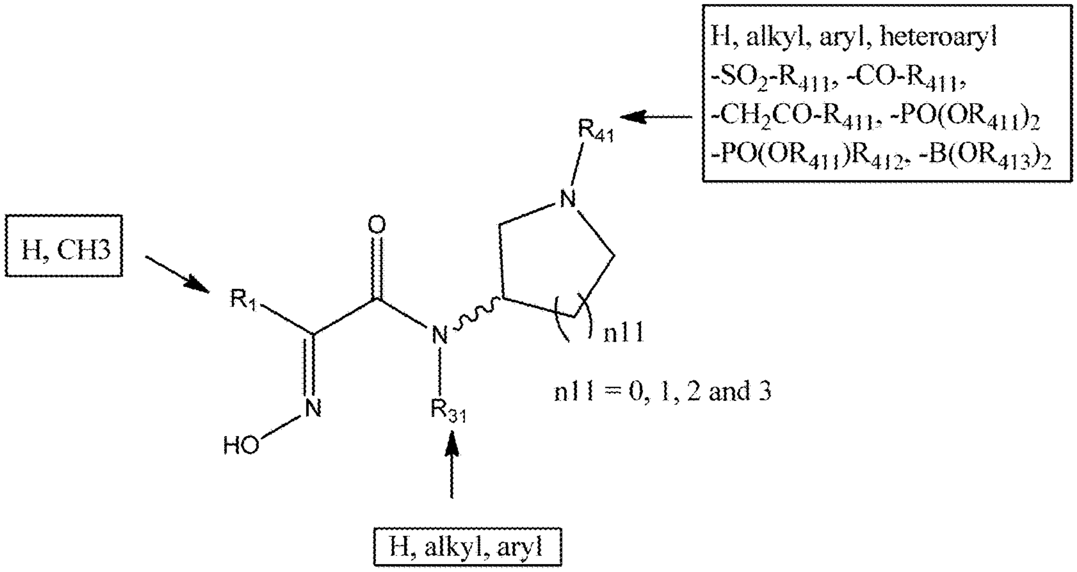
FIG. 20 shows exemplary variations in the substituents on the AN and DN nitrogen atoms of compound 5.
Figure 21:
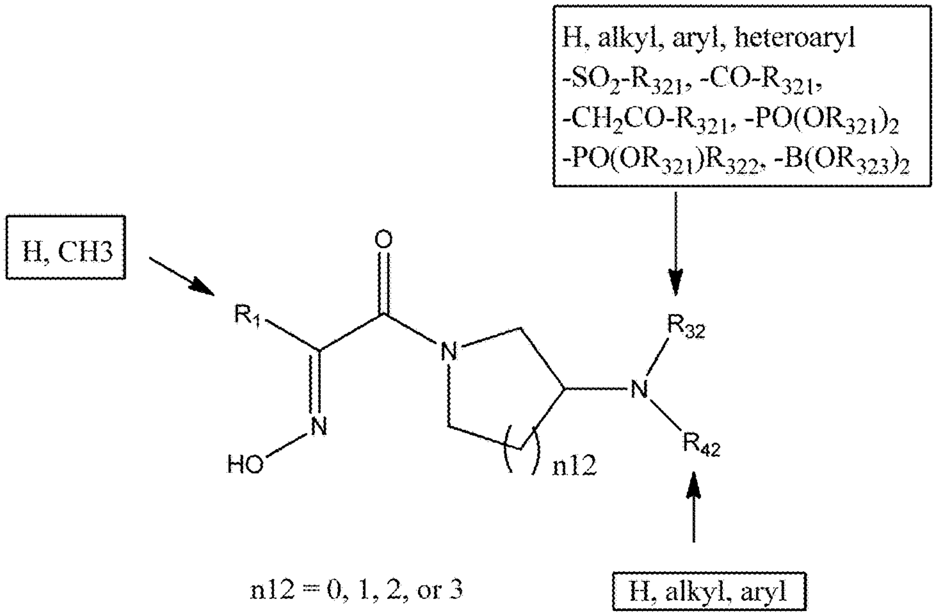
FIG. 21 shows exemplary variations in the substituents on the AN and DN nitrogen atoms of compound 6.

In compounds 5-10 described in Examples 5 to 9, the nature of the $R_1$ group can be the simple hydrogen atom or a methyl group. The nature of the $R_{31}$ group (in compounds like 5) can also be expanded to include the simple hydrogen atom, but it can be adapted to an alkyl group (n-alkyl or branched alkyl moiety), an aryl or heteroaryl group. Regarding the DN moiety in both classes of compounds (5 and 6), the nature of the R groups (i.e. $R_{41}$ in 5 and $R_{32}$ and $R_{42}$ in 6) can be varied more freely due to the basicity of the DN. FIGS. 20 and 21 shows some of the possible variations in the substituents on the nitrogen atoms.

The nature of the $R_{31}$, and $R_{41}$ groups in compound 5 and $R_{32}$, and $R_{42}$ groups in compound 6 is can be any suitable groups that is known to a person of skill in the art. These synthetic chemistry opens up the possibility of tapping into the chemical space that natively comes associated with the modification of a nitrogen center. Thus, alkylations making use of simple or complex alkyl halides, including Cl, Br or I, would provide tertiary nitrogen atoms that can vary in their degree of basicity.

Acylations on the DN employing various commercially available acyl chloride or acyl anhydrides (e.g. acetic anhydride or benzoyl chloride) would yield an amide at the DN position. Acylation, of course, would result in the complete nullification of the basic DN. Other reactions can be carried out off this DN center that are commonly associated with Nitrogen derivatizations. Some of these include: Michael additions (1,4-additions to α,β-unsaturated systems), reactions with ketenes or chloroformates to give carbamates, reactions with isocyanates to produce ureas, and so on.

Library generation from this scaffold can be accomplished at several points in the structure above. For example at R1, one can produce 2 kinds of oximes from these base structures (when R1=H or $CH_3$). Another point for expanding the library, albeit not to a great extent is at the AN (amide nitrogen) exemplified by $R_{31}$. The point at which one can obtain the most diverse library for whichever class of compounds arising from this scaffold is off of the DN (distal nitrogen) via $R_{41}$. Thus, for example when $R_{41}$═H, this compound can be obtained by the trifluoroacetic acid cleavage in dichloromethane of the Boc protecting group originally present in the building block. When $R_{41}$=alkyl, one has two options. The first one is the direct alkylation of the DN with any alkyl bromide (or chloride or even iodide) or the reductive amination of a library of ketones and aldehydes with sodium triacetoxyborohydride in dichloromethane. Note that this alkylation step (that includes the reductive amination maneuver) must be done before the coupling to the oxime, thus these modifications are to yield the amine building blocks used in subsequent steps and not the final one. When $R_{41}$=aryl, heteroaryl; one can invoke the use of palladium-mediated coupling of aryl/heteroaryl iodides (Buchwald coupling) in the presence of phosphine ligands. When $R_{41}$═—$SO_2$—$R_{411}$ and —CO—$R_{411}$, these transformations can be carried out by reacting the DN with the corresponding sulfonyl and acyl chloride respectively. When $R_{41}$═$CH_2$—$COR_{411}$, the compound can be assembled by reacting the DN with the α-bromoketone starting material for which there exists an extensive library of commercially available compounds from reputable vendors such as VWR and Aldrich. Installation of the phosphate and boronate groups, for $R_{41}$═—PO $(OR_{411})_2$, —$PO(OR_{411})R_{412}$ and —$B(OR_{413})_2$, can be accomplished by reacting the DN with the corresponding chloride of the phosphate (e.g. phosphoroyl chloride) or of the boronate (e.g. Cl—$B(OR_{413})_2$).

Application of a same linking approach for the generation of cyclic derivatives from compounds where the distance between the AN and the DN is of 3-carbon atoms (i.e. —$(CH_2)_3$-units).

The same technique can yield additional classes of cyclic compounds 7-10, each one unique with its main carbon framework based on corresponding compound 7a to 10a as illustrated in FIGS. 22A-22D. The arrows indicate the points to connect in order to generate novel cyclic structures exemplified by compounds 7-10.

Figure 22A:
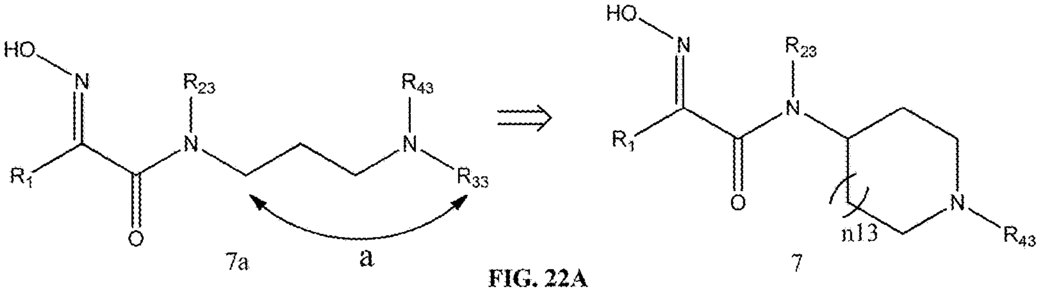
FIG. 22A shows a schematic illustration of the structure of cyclic compound 7 based on the main carbon framework of corresponding compound 7a cyclized as indicated by arrow "a".
Figure 22B:
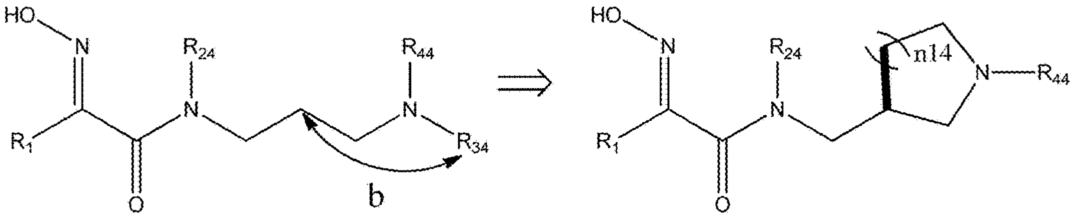
FIG. 22B shows a schematic illustration of the structure of cyclic compound 8 based on the main carbon framework of corresponding compound 8a cyclized as indicated by arrow "b".
Figure 22C:
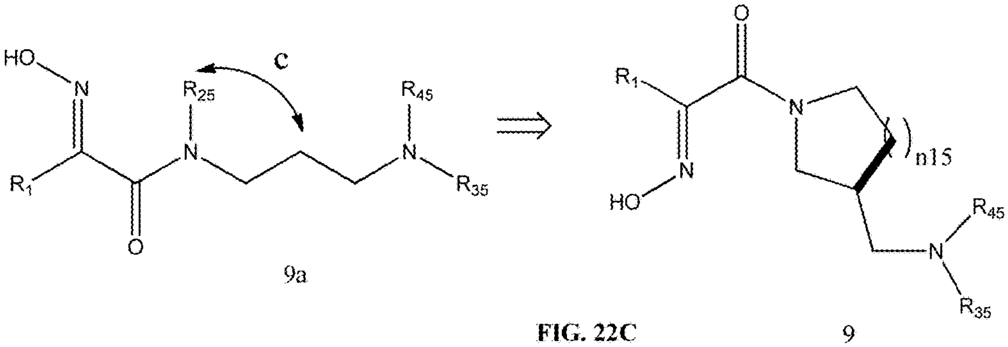
FIG. 22C shows a schematic illustration of the structure of cyclic compound 9 based on the main carbon framework of corresponding compound 9a cyclized as indicated by arrow "c".
Figure 22D:
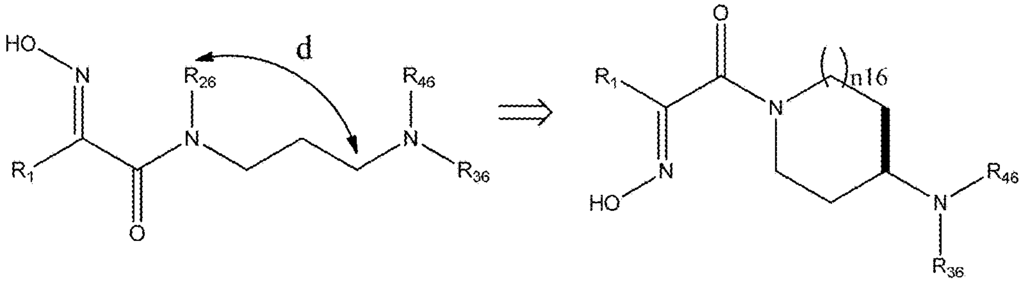
FIG. 22D shows a schematic illustration of the structure of cyclic compound 10 based on the main carbon framework of corresponding compound 10a cyclized as indicated by arrow "d".
Figure 22E:
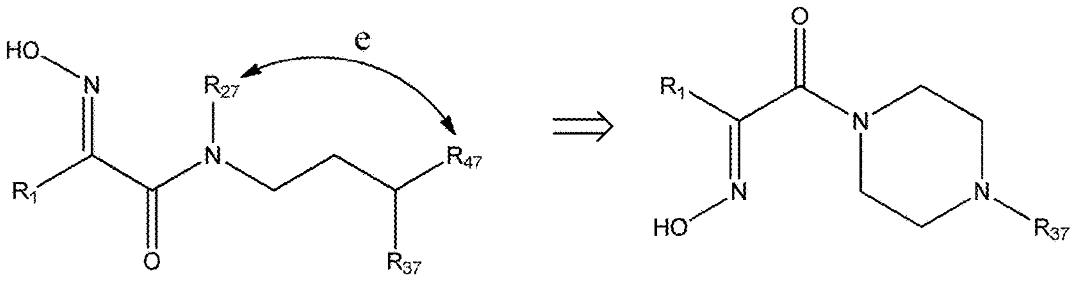
FIG. 22E shows a schematic illustration of the structure of cyclic compound 15 based on the main carbon framework of corresponding compound 15a cyclized as indicated by arrow "e".

The same technique can also yield additional classes of cyclic compound 15, each one unique with its main carbon framework based on corresponding compound 15a as illustrated in FIG. 22E. The arrow "e" indicates the points to connect in order to generate novel cyclic structures exemplified by compound 15. Compound 15 can be made by following the following reaction scheme and described in more detail in Example 13.

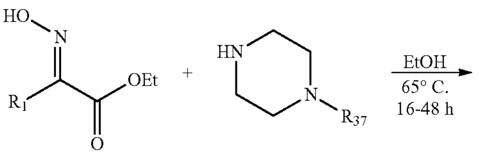

R1 = H, CH3

-continued

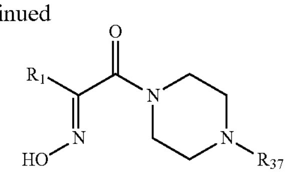

15

The modifications at the AN (amide nitrogen) when there is a substituent groups, R23 and R24 as in compounds 7 and 8 respectively, directly attached to it are H, alkyl and aryl. The modifications for R33 and R43 for expanding the library of compounds at this point will involve the same chemical manipulations that are described in Example 12. Again, these manipulations in R33-R36 and R43-R46 (for all compounds 7-10 above) need to be carried out before the coupling of the amine to the oxime glyoxylate ester.

In some embodiments, library elaboration from each scaffold as illustrated by compounds 7-10 can be accomplished by introducing diversity with each substituent group on the AN and DN nitrogen (i.e. $R_1$, R23-R26, R33-R36 and R43-R46). The procedures as denoted in Example 12 are also applicable for libraries of compounds 7-10. Therefore, in these types of compounds, the nature of the $R_1$ group can again be the simple hydrogen atom or a methyl group. The nature of the R23-R24 groups as in compounds 7-8 can be H, a linear or branched, optionally additional one to six heteroatoms or one to three substituents containing, alkyl, alkenyl, alkynyl, aryl, arylalkyl or alkylaryl carbon atom or a heteroatom having equal to or less than 18 carbon atoms.

With regards to the DN moiety in all these types of compounds (7 through 10), the nature of the DN substituent groups, for example, R35-R36 and R43-R46 in compound 7-10, can be varied more freely due to the basicity of the DN. The nature of the R35-R36 and R45-R46 groups in compounds 9 and 10 are so selected to modify the basicity of DN and thus optimize the activity of these compounds.

Library generation from the scaffold of compounds 5-10 and 15 can be accomplished at several points in the structure shown in FIGS. 20-21 and 22A to 22E. For example at R1, 2 kinds of oximes can be produced from these base structures when R1=H or CH3. Another point for expanding the library, is at the AN (amide nitrogen) exemplified by R31, R23 and R24 in compounds 5, 7 and 8 respectively.

A library can also be diversified at the point of DN (distal nitrogen) of the scaffolds of compounds 5-10 and 15, depending on the selections of R32, R35-R37, R41-R46 in each of the corresponding compounds. Thus, for example when R41-R46=H, these compound can be obtained by the trifluoroacetic acid cleavage in dichloromethane of the Boc (i.e. tert-butyloxycarbonyl) protecting group originally present in the building blocks for all compounds 5-10 and 15 in FIGS. 20-21 and 22A to 22E.

When R33-R36, and R43-R46=alkyl, there are two options for building the diversity on the DN nitrogen. The first one is the direct alkylation of the DN with an alkyl bromide, chloride or iodide or the reductive amination of a library of ketones and aldehydes with a reducing agent including sodium triacetoxyborohydride in dichloromethane for all compounds 7-10. This alkylation step which includes a reductive amination reaction, can be done before the coupling to the oxime, thus these modifications are to yield the amine building blocks used in subsequent steps and not the final one.

When R33-R36, and R43-R46=aryl, heteroaryl, palladium-mediated coupling of aryl/heteroaryl iodides (Buchwald coupling) in the presence of phosphine ligands can be used to diversify the DN nitrogen. When R33-R36, and R43-R46=—SO2-R411 and —CO—R411, these transformations can be carried out by reacting the DN with the corresponding sulfonyl and acyl chloride respectively.

When R33-R36, and R43-R46=CH2-COR411, the compound can be assembled by reacting the DN with the α-bromoketone starting material for which there exists an extensive library of commercially available compounds including those from VWR and Aldrich vendors.

Installation of the phosphate and boronate groups, for R33-R36, and R43-R46=—PO(OR411)2, —PO(OR411) R412 and —B(OR413)2, can be accomplished by reacting the DN nitrogen with the corresponding chloride of the phosphate (e.g. phosphoroyl chloride) or of the boronate (e.g. Cl—B(OR413)2).

With reference to compounds 9 and 10, R35 and R45 on compound 9 and R46 and R36 on compound 10, could be the same or different moieties. They are different in case of asymmetrically substituted amine in the instance where direct alkylation of the DN is carried out. Whereas if the DN is acylated, sulfonylated or boron-protected, only one step modification is practical and that nitrogen will not react further unless it is deprotonated with a strong base in the case of the N-sulfonyl product.

Thus, alkylations making use of simple or complex alkyl halides (R—X, where X is Cl, Br or I) would provide tertiary nitrogen atoms that can vary in their degree of basicity. Acylations on the DN employing various commercially available acyl chloride or acyl anhydrides (e.g. acetic anhydride or benzoyl chloride) would yield an amide at the DN position. Acylation, would result in the complete eradication of the basic DN. Other reactions can be carried out off this DN center that are commonly associated with Nitrogen derivatizations. Some of these include: Michael additions (1,4-additions to α,β-unsaturated systems), reactions with ketenes or chloroformates to give carbamates, reactions with isocyanates to produce ureas, and so on.

Example 13: Synthesis of AN/DN Cyclized Compound 15

An example of an AN/DN cyclized oxime herein described is provided by compound 15 where the amine directly attached to the carbonyl moiety adjacent to the oxime is part of a piperazine ring.

15

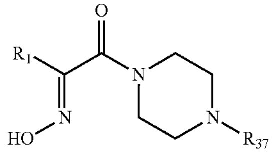

The 4-aminoprotected piperazine (3 mmol) was added to a solution of ethyl glyoxylate oxime (3 mmol) in ethanol (10-20 mL) at ambient temperature. The resulting mixture was heated to 65° C. Depending on the nature of the amine used for the reaction, reaction times range anywhere between 16-48 hours at 65° C. Yields are typically between 50-70% with the remaining material being unreacted ethyl glyoxylate oxime. Depending on the nature of the 1-protected 3-aminopyrrolidine starting material, the product may precipitate during the reaction or would require synthesis by flash chromatography (hexane 4 EtOAc). The reaction can be monitored by TLC (1:1 EtOAc/hexane) using UV and the disappearance of the ethyl glyoxylate oxime ($R_f$=0.6).

Example 14: Synthesis of a AN Piperidinyl/DN Triazole Oxime

An example of an AN/DN piperidinyl/DN triazole oxime herein described is provided by compound 16

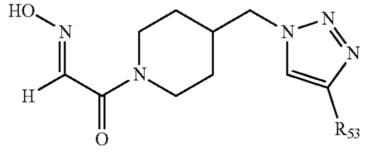

16

The R group in the piperidine-based triazoles can be any alkyl group which is inclusive of simple alkyl chains as well as branched alkyl chains. R53 can also be an aromatic ring directly attached to the DN and as such subject to different patterns of substitution in the rings with various functional triazole ring. The R53 group can act in this sense as well by possessing functional groups that can interact with amino acid residues in the interior of the active site. One relevant aspect of this binding is that good binding it is not expected to necessarily translate into good reactivation, at least in case that i) the oxime binding with the R group is not reversible and does not result in reactivation of the enzyme, thus blocking the active site and thus the adducted serine and 2) the orientation of the binding event does not occur towards the adducted serine residue, and the the reactivation will not occur.

The nature and size of R53 groups on the triazole ring in compound 16 or R54 in compound 17 can be selected to confer lipophilicity while minimizing potential disruption to the binding to the active site. In particular it is expected that small hydrophobic groups (i.e. small alkyl chains, preferably C1-C6) will produce compounds that possess enough lipophilicity (c log P value between 1-2) to cross the BBB. Current computational data support the possible avoidance of aromatic residues for R in these compounds as it enhances tight binding in the active site and prevents the oxime part of the molecule from reaching the adducted serine efficiently.

Compound 16 can be obtained by the following reaction scheme

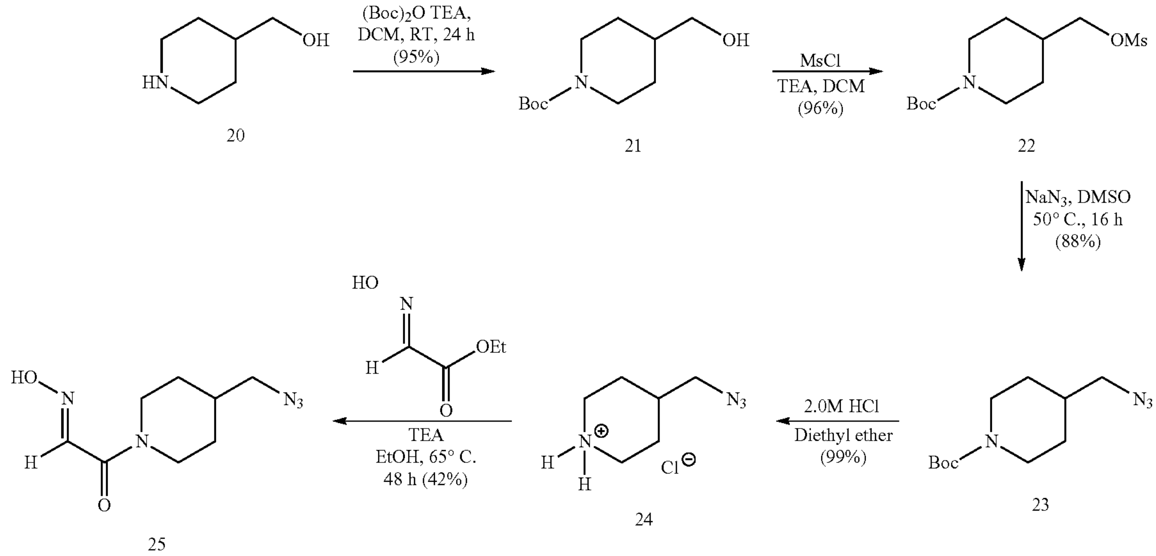

groups (e.g. $NO_2$, OH, $NH_2$, alkyl groups, CF3, halogens such as I, Cl, F and Br, ethers (like $OCH_3$), amides like (NHAc)). The aromatic moiety can be also a heteroaromatic moiety such as pyridine, thiophene, furan, imidazole, oxazole and pyrazole. The size of the carbon chain in these compounds once R53 is an alkyl group ranges anywhere from C1 to C18. However, one expectation from using Carbon chains longer than C8 is that the drug's bioavailability might be diminished due to its increased lipophilicity with carbon lengths over 8 (i.e. C#>C9). Now, long chains (i.e. C9-C18) are expected to procure compounds that can be used for micelle formations (another application).

The two general aspects in the class of compounds represented by triazole compound 16 that make them viable candidates are: 1) the presence of the oxime moiety that may act as a reactivator and 2) the presence of a DN moiety which is filled by one of the nitrogen atoms making up the Synthesis of Compound 21:

To a stirring solution of 4-piperidinemethanol (50.0 g, 500 mmol) and triethylamine (210 mL, 1500 mmol) in DCM (400 mL) in a 1000 mL RB flask equipped with a large stir bar cooled to 0° C. in an ice bath, was added Boc anhydride (120 g, 550 mmol) portionwise. The reaction mixture was allowed to warm to room temperature and stirred vigorously overnight. All volatiles were removed under reduced pressure at 50° C. and the crude residue purified by flash column chromatography (hexane 7:3 EtOAc/hexane) to give tert-butyl 4-(hydroxymethyl)piperidine-1-carboxylate as a white solid, yield 95.1 g, 95%. $^1H$ NMR (600 MHz, $CDCl_3$): 4.16 (2H), 3.54 (2H), 2.70 (2H), 1.75 (2H), 1.50 (9H), 1.45 (1H), 1.19 (2H).

Synthesis of Compound 22:

In a 1000 mL RB flask, tert-butyl 4-(hydroxymethyl) piperidine-1-carboxylate (compound 21) (66 g, 306 mmol)

was dissolved in DCM (300 mL) and treated with triethylamine (52 mL, 368 mmol). The solution was cooled to 0° C. in an ice bath and treated using an addition funnel with mesyl chloride (28 mL, 368 mmol) in DCM (50 mL). The addition was done dropwise over 15 minutes. The resulting suspension was stirred vigorously at room temperature overnight. The white solid was removed using suction filtration and the solid washed with cold DCM (2×50 mL). The light yellow filtrate was extracted with brine (2×200 mL), dried over anhydrous sodium sulfate and evaporated under reduced pressure to give the mesylate as a light yellow oil that was purified by flash column chromatography hexane→1:1EtOAc/hexane) to give mesylate 22 as an off-white solid, yield 86.1 g, 96%.

Synthesis of Compound 23:

Mesylate 22 (27 g, 92 mmol) was dissolved in DMSO (100 mL) in a 250 mL RB flask equipped with a stir bar. To the solution, sodium azide (9 g, 139 mmol) was added and the mixture heated to 50° C. overnight. The reaction was monitored by TLC (Mesylate Rf=0.2; Azido product Rf=0.7 in 1:9 EtOAc/hexane) and found to be completed after the overnight heating. The mixture was extracted with diethyl ether/$H_2O$ and the organic phase extracted copiously with water to get rid of the DMSO, dried over anhydrous sodium sulfate and evaporate under reduced pressure to give a yellow oil that was purified by flash column chromatography (hexane→2:8 EtOAc/hexane) to give the azido compound 23 as a light yellow oil, 19.4 g, 88%.

Synthesis of Compound 24:

Azido compound 23 (25.6 g, 107 mmol) was dissolved in diethyl ether (100 mL) in a 250 mL RB flask equipped with a stir bar. The solution was cooled to 0° C. and treated dropwise using an addition funnel with 2.0 M HCl in diethyl ether (159 mL, 321 mmol). The resulting solution was vigorously stirred at room temperature overnight. The following day, a white suspension was observed with some of the white solid stuck to the sides of the flask. The reaction was filtered and the white solid washed with diethyl ether (3×100 mL), dried under vacuum overnight. The azido compound 24 hydrochloride salt was obtained as a white solid, 18.6 g, 99%.

Synthesis of Azido-Oxime Compound 25:

Azido compound 24 HCl Salt (20 g, 114 mmol) was taken up in EtOH (60 mL) and treated with triethylamine (17 mL, 125 mmol). To this solution, ethyl glyoxylate oxime (13.3 g, 114 mmol) was added. The flask was equipped with a condenser and the reaction mixture heated to 65° C. with vigorous stirring for two days. TLC analysis showed the formation of the more polar product (Ethyl glyoxylate oxime $R_f$=0.7 and product $R_f$=0.4 in 1:1 EtOAc/hexane). The mixture was transferred to a 1000 mL separatory funnel and partitioned (DCM/water). The organic phase was washed with brine (2×200 mL), dried over anhydrous sodium sulfate and evaporated under reduced pressure to give a yellow oil. The mixture was purified by flash column chromatography (1:1→7:3 EtOAc/hexane) to give the azido oxime compound 25 as a light yellow oil, 6.7 g, 28%. Unreacted ethyl glyoxylate was also recovered 8.8 g, 66%.

Figure 13:
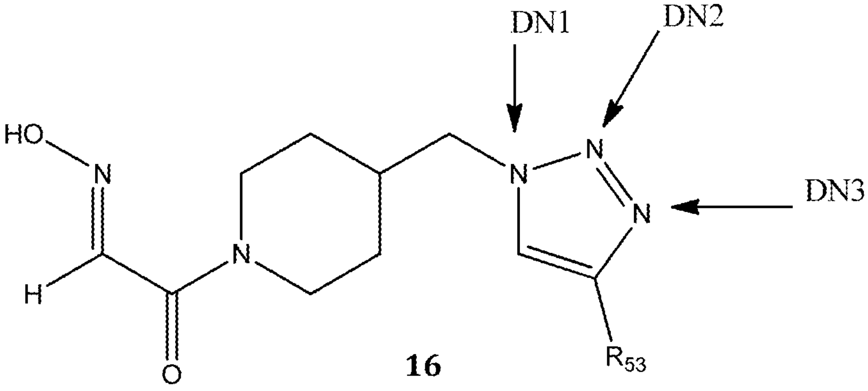
FIG. 13 shows a schematic illustrating presence of a plurality of DN nitrogen atoms, DN1, DN2, and DN3 with increasing basicity on a triazole moiety in compound 16.
Figure 14:
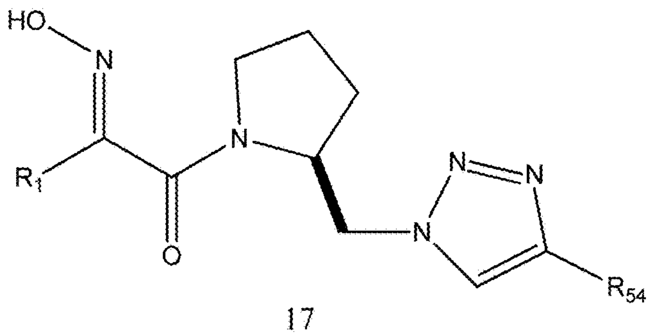
FIG. 14 shows a schematic illustrating an exemplary triazolyl amide oxime compound 17, wherein R3 on the triazole moiety comprises a alkyl groups ranging from C1-C18, such as methyl, ethyl, isopropyl, n-butyl, sec-butyl, and iso-butyl and substituted phenyl group, electron donating group (EDG) substituted phenyl group, electron withdrawing group (EWG) substituted phenyl group, six-membered heteroaromatic rings, substituted or unsubstituted five-membered heteroaromatic rings including thiophene, furan and pyrrole.
Figure 14:
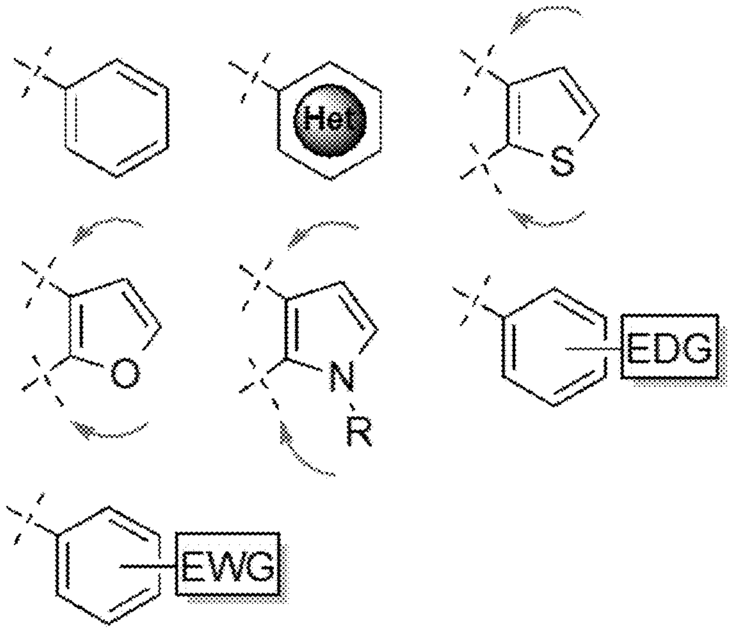

FIG. 13 shows a structure of generalized compound 16 showing its characteristics including the basic DN3, DN1, and DN2 nitrogen atoms with increasing basicity. This group of compounds, includes 3 basic DNs denoted DN1, DN2, and DN3. Basic rules that govern the basicity of triazole nitrogen atoms predict that DN3 should be the first site of protonation in this compound. At pH 0-2, it is expected that DN3 will mostly become protonated. Thus, this signifies that the protonated DN will be far more removed from the AN as in other cases previously touched upon (i.e. compound 5 for example).

To synthesize compound 16, azido oxime compound 25 (1 mmol) was combined with alkyne compound 26 (1 mmol, RCCH) in a 1:2 tBuOH/water mixture (5 mL) and treated sequentially with sodium ascorbate (0.1 mmol) and $CuSO_4$-$5H_2O$ (0.05 mmol). The mixture was stirred vigorously at room temperature overnight. The extent of the reaction is followed by TLC and the disappearance of the azide and/or alkyne can be monitored this way to see the extent of the reaction. The triazole formed is more polar that either component in this procedure and even though it usually precipitates out of the 1:2 tBuOH/water mixture, water may be added to aid in this process, so that column chromatography is avoided. Washing the precipitated triazole product with water and then diethyl ether produces the material in >95% purity which is enough for running the biological assays.

Example 15: Synthesis of AN Pyrrolidinyl/DN Triazole Oxime 17

An example of an AN/piperidinyl/DN triazole oxime herein described is provided by compound 17

17

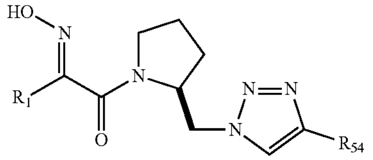

The R1 group, once again can be H or $CH_3$. The $R_{54}$ group can be an alkyl chain (linear or branched), aromatic groups, heterocyclic rings, and these can be bearing any degree of substitution with functional groups that can be electron donating (EDG) or electron withdrawing (EWG) in nature.

Figure 15:
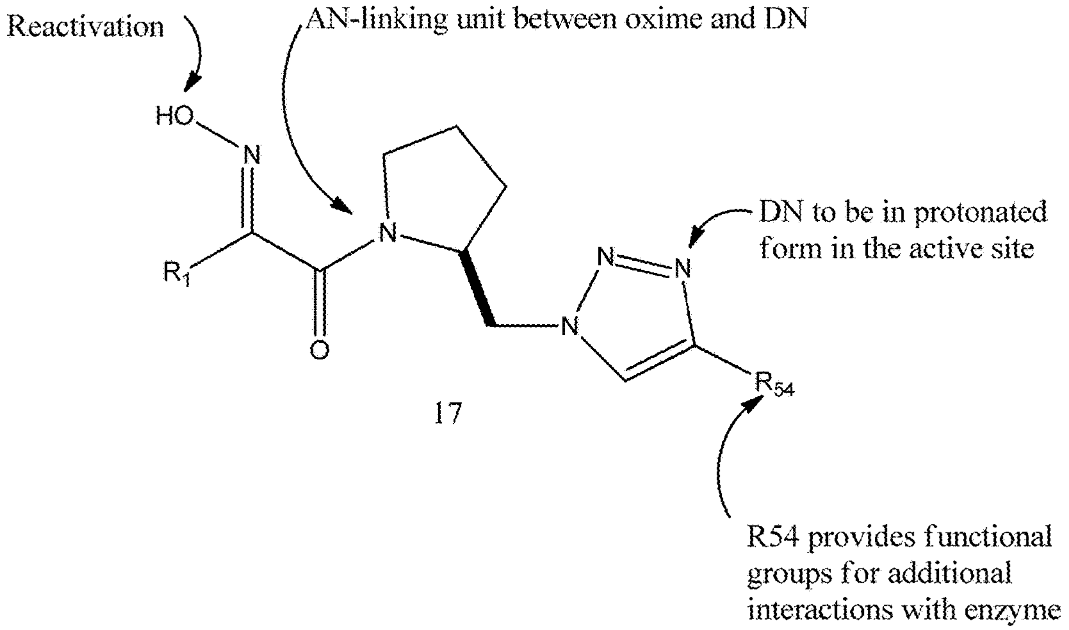
FIG. 15 shows a schematic illustrating different functions of various atoms groups on the oxime compound 17 for binding and reactivation of nerve agent-inhibited acetylcholinesterase (AChE).
Figure 16:
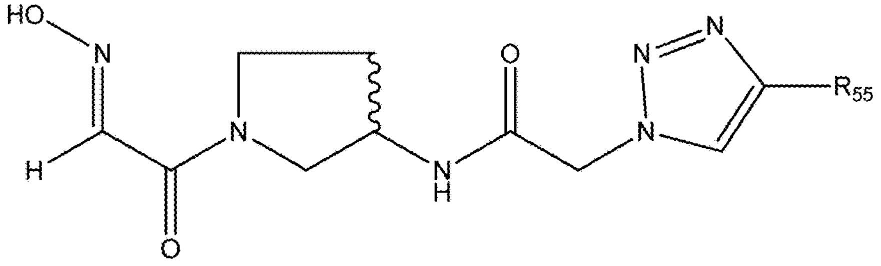
FIG. 16 shows the structure of a triazole amide oxime compound 18 wherein the oxime amide nitrogen is part of a heterocycle and wherein n17=0, 1, 2, or 3.

In some embodiments, R54 on the triazole moiety comprises a alkyl groups ranging from C1-C18, such as methyl, ethyl, isopropyl, n-butyl, sec-butyl, and iso-butyl and substituted phenyl group, electron donating group (EDG) substituted phenyl group, electron withdrawing group (EWG) substituted phenyl group, six-membered heteroaromatic rings, substituted or unsubstituted five-membered heteroaromatic rings including thiophene, furan and pyrrole. Please refer to the figure below for some representative examples:

Using the same line of thought as for the previous compounds, the DN was placed in the triazole moiety of compound 17 which acts to enhance the binding of this compound to the active site and provides it with the right orientation so as to carry out the reactivation. The overall features of this class of compounds is given in FIG. 15.

A schematic of the synthetic route for compound 33 is provided below that will be used for the synthesis of this class of compounds.

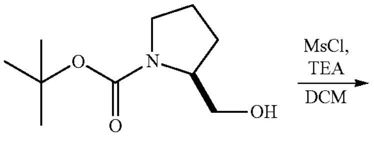

27

-continued

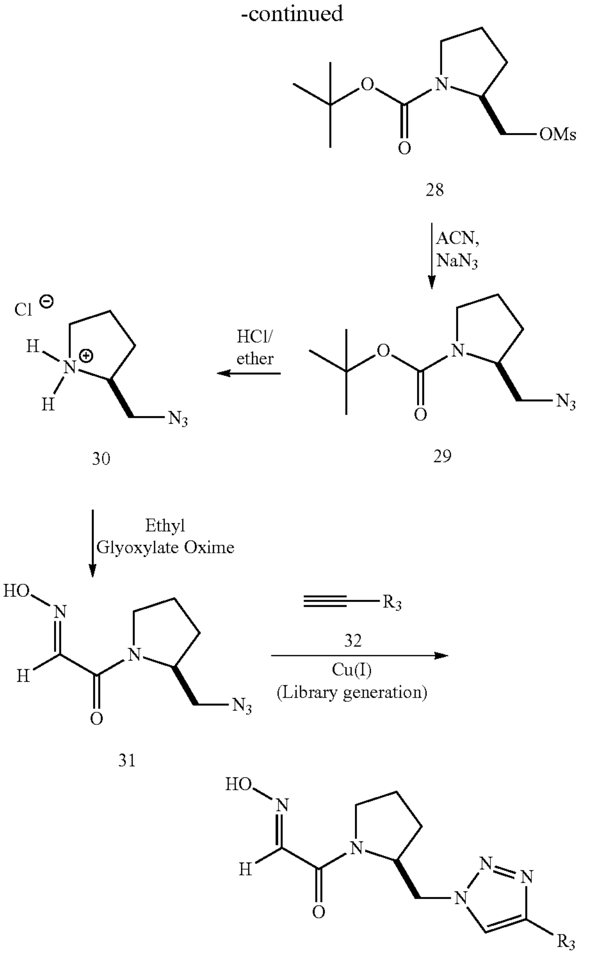

28, 29, 30, 31, 33

This new synthetic route will result in the production of this group of triazole oximes. The synthesis of compound 31 and 33 is in parallel with that of compound 25.

Synthesis of Compound 28:

N-Boc-L-prolinol 27 (11.4 g, 56.6 mmol) was dissolved in DCM (100 mL) in a 250 mL round bottomed flask equipped with a stir bar. Triethylamine (TEA, 12 mL, 84.9 mmol, 1.5 equiv.) was added to the solution and the mixture was cooled to 4° C. using an ice bath. Mesyl chloride (6.6 mL, 84.9 mmol, 1.5 equiv.) as a solution in DCM (15 mL) was added to the alcohol solution dropwise using an addition funnel at 4° C. After the addition, the mixture was allowed to warm up to ambient temperature and this was stirred overnight. The next day, the mixture was partitioned ($H_2O$/DCM) and the organic phase extracted with brine (NaCl/$H_2O$, 2×100 mL), dried with anhydrous $Na_2SO_4$ and volatiles evaporated in vacuum at 50° C. to yield a tan-colored solid. The solid was purified by silica gel flash column chromatography (hexane→1:1 EtOAc/hexane) to furnish mesylate 28 as a white solid (15.1 g, 96%). Rf=0.6 (1:1 EtOAc/hexane). HRMS (CI) m/z calculated for $C_{11}H_{21}NO_5S$ [M+]: 279.1140; found 279.1137.

Synthesis of Compound 29:

Mesylate 28 (15.1 g, 54.1 mmol) was dissolved in acetonitrile (100 mL) in a 250 mL round bottomed flask equipped with stir bar. To the solution, sodium azide ($NaN_3$, 4.21 g, 64.9 mmol, 1.2 equivalent to mesylate) was added in small portions and the resulting mixture was heated to 60° C. overnight. The next day, the mixture was partitioned ($H_2O$/EtOAc) and the organic phase extracted with brine (NaCl/$H_2O$, 2×100 mL), dried with anhydrous $Na_2SO_4$ and volatiles evaporated in vacuum at 60° C. to yield a light yellow-colored oil. The oil was purified by silica gel flash column chromatography (hexane→3:7 EtOAc/hexane) to give azide 29 as a colorless oil (10.9 g, 89%). Rf=0.4 (3:7 EtOAc/hexane). 1H NMR (DMSO-Δ6) δ 3.56-3.44 (m, 3H), 1.90-1.85 (m, 4H), 1.84-1.80 (m, 2H), 1.51 (s, 9H). HRMS (CI) m/z calculated for $C_{10}H_{18}N_4O_2$ [M+]: 226.1430; found 226.1425.

Synthesis of Compound 30:

Boc-protected azide 29 (9.0 g, 39.8 mmol) was dissolved in diethyl ether (15 mL) in a 250 mL round bottomed flask equipped with a stir bar. The colorless solution as cooled to 4° C. using an ice bath and treated dropwise using an addition funnel with 2 M HCl/$Et_2O$ (80 mL, 158.8 mmol, 4 equiv. to 29). The resulting mixture was vigorously stirred at ambient temperature overnight. The next day, a white solid was noted suspended in the mixture and stuck to the walls of the flask. The solid was collected by vacuum filtration, washed with diethyl ether (3×20 mL) and dried under vacuum for 2 hours. The salts were found to be pure by NMR analysis and belonging to the HCl salt of compound 30 (5.67 g, 88%). Rf=0.3 (9:1 DCM/MeOH, basic form of 30). HRMS (CI) m/z calculated for $C_5H_{11}N_4$ [M+H+]: 127.0978; found 127.0984.

Synthesis of Compound 31:

Azidopyrrolidine salt 30 (0.9 g, 5.55 mmol) was taken up in ethanol and treated with triethylamine (0.91 mL, 6.66 mmol, 1.2 equiv. to 30), followed by ethyl glyoxylate oxime (520 mg, 4.44 mmol, 0.8 equiv.). The resulting mixture was heated to 65° C. overnight. The next day, the mixture was cooled to ambient temperature and partitioned (DCM/$H_2O$). The organic phase was washed with $H_2O$ (50 mL), brine (NaCl/$H_2O$, 2×50 mL), dried over $Na_2SO_4$ and volatiles evaporated in vacuum at 50° C. to yield a yellow colored oil. Purification of the oil via silica gel flash column chromatography (hexane→EtOAc) to give azido-oxime product as a pale yellow oil (153 mg, 14%). Rf=0.2 (1:1 EtOAc/hexane). HRMS (CI) m/z calculated for $C_7H_{11}N_5O_2$ [M+]: 197.0913; found 197.0911.

Synthesis of Compound 33:

Azido compound 31 (100 mg, 0.51 mmol) and terminal alkyne (0.51 mmol) were taken up in a 1:1 tBuOH:$H_2O$ mixture (6 mL) in a 20 mL scintillation vial equipped with a small stir bar. The suspension was treated sequentially with sodium ascorbate (10 mg, 0.05 mmol, 10 mol %) and copper iodide (CuI, 4.8 mg, 0.03 mmol, 5 mol %). The resulting mixture (suspension) was stirred vigorously at ambient temperature overnight. Usually after 4 hours, precipitates for some azide-alkyne combos begin to appear (i.e. triazole products), while in some other cases the mixture remains a solution at which point a work-up and purification (silica gel column) procedure is needed.

Example 16: Synthesis of AN Pyrrolidinyl/DN Triazole Oxime 18

Figure 17:
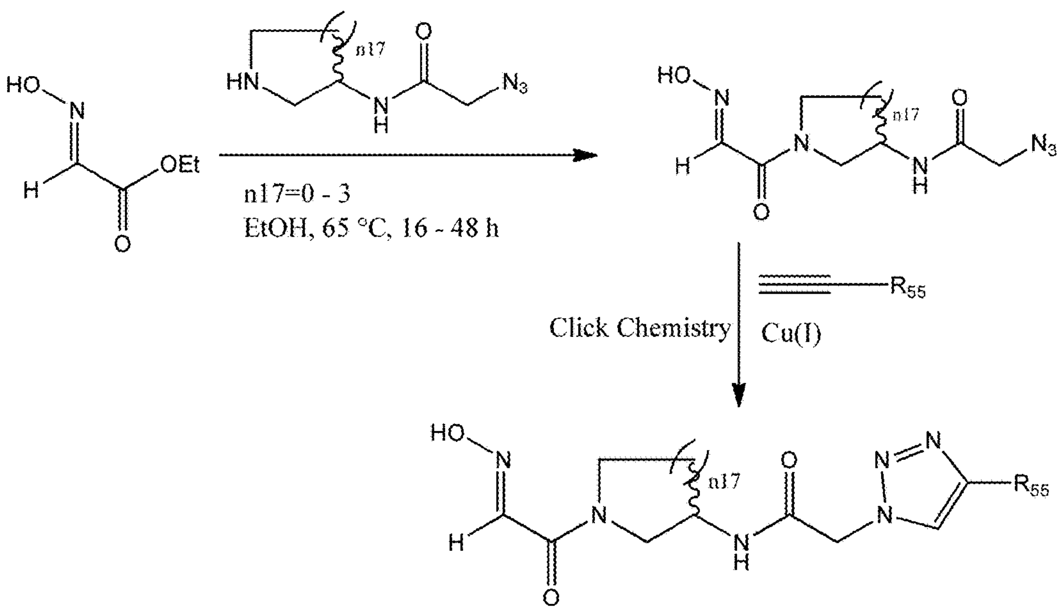
FIG. 17 shows a synthetic scheme for the synthesis of a triazolyl amide oxime compound 18 which applies Click Chemistry for the triazole moiety formation.

FIG. 17 shows a synthetic scheme for the synthesis of an oxime compound 18 which applies Click Chemistry for the triazole moiety formation. The wavy bond in the a molecular formula as used herein indicates either R, S configuration or a mixture of the two configurations.

Example 17: Integrated Method of Drug Discovery

Oximes of the present disclosure can be subjected to an integrated method of selecting and optimizing a biologically active compounds against a pharmaceutical target molecule.

Figure 5:
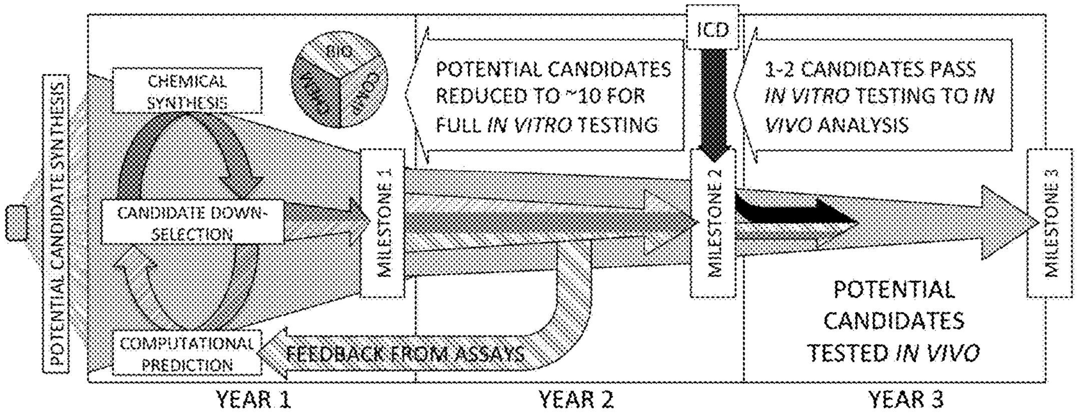
FIG. 5 shows a schematic illustration of an approach to drug discovery with milestones and yearly goals applicable to oximes of the present disclosure.

FIG. 5 shows a schematic illustration of the an integrated method of selecting and optimizing an biologically active compounds against a pharmaceutical target molecule.

Initially a biological target molecule is selected in association with a disease or physiological condition. A computational model is created based on the molecular parameters of the biological target molecule. A first generation candidate molecules are generated based on the Computational Binding Free Energy Calculations. The first generation candidate molecules are synthesized, optionally using combinatorial chemistry. The synthesized candidate molecules are subjected to preliminary in vitro testing for potential activities.

In milestone one, a selection (e.g. compounds 5-10 or compounds obtained through combinatorial library exemplified in Example 11), of the first generation candidate molecules which show most activity in the in vitro testing are identified by full in vitro testing, called first milestone one candidate molecules. Full in-vitro assays ascertain chemical and metabolic stability of candidate molecules. Based on the structures of the milestone one candidate molecules, computational model parameters are adjusted accordingly in a first iteration cycle to better fit the in vitro testing results of the milestone one candidate molecules.

A second generation of candidate molecules are generated based on the updated computational model parameters in the first iteration cycle. Those second generation of candidate molecules are synthesized, optionally using combinatorial chemistry. The synthesized candidate molecules are subjected to preliminary in vitro testing for potential activities.

In milestone one, a selection, for example 10 compounds, of the second generation candidate molecules which show most activity in the in vitro testing are identified by full in vitro testing, called second generation first milestone one candidate molecules.

The cycle of iteration was continued until at least one candidate molecule, a milestone two candidate molecule, was identified having a biological activity above a mile stone two threshold value in the full in vitro testing. The milestone two candidate molecule is subjected to an in vivo testing.

The results of the in vivo testing of the milestone two candidate molecule is analyzed against a threshold end point. The structures of milestone two candidate molecules are analyzed for favorable structural attributes and such information is fed back to selection for potential candidates for in vivo testing.

A structural attribute is an arrangement of atoms in a molecule that are known, based on the computational model disclosed herein and confirmed by in vivo screening (e.g. PAMPA and AChE reactivation assay), to enhance activity or a desired property including AChE reactivation and BBB permeability. Thus, evaluation of compounds that are already predicted by the present computational model not to have a great BBB crossing profile or a mediocre AChE active site binding for reactivation also provides information about the nature of what structural features (attributes) are not needed or should be avoided in the drug discovery process.

One of the features that separate the approach exemplified in this example from other approached used, is the fact that the exemplified approach has heavily relies on computational modeling. The exemplified method possesses not only the synthesis and in vitro/in vivo evaluation, can also rely on computational modeling in the drug-discovery process. In the present approach, computational chemistry serves to guide efforts as accentuated as in the present disclosure.

Example 19: Parallel Artificial Membrane Permeability Assay (PAMPA)

The Parallel Artificial Membrane Permeability Assay (PAMPA) is a commercially available platform used to screen drug compounds for passive diffusion across an artificial phospholipid bilayer. The platform available from Corning Life Sciences (Gentest Pre-coated PAMPA Plate System) is composed of two fluid-filled chambers separated by an artificial lipid bilayer. This bilayer is composed of structured layers of multiple phospholipids. Donor well volume is 0.3 mL, receiver well volume is 0.2 mL, and filter area is 0.3 $cm^2$. A compound of interest in solution (Hank's Balanced Salt Solution) at a concentration of approximately 100 μM is added to one chamber and allowed to diffuse across the membrane to another chamber for five hours at 25° C. Compound is measured by quantifying the material in solution using the Waters Acquity ultra performance liquid chromatography (UPLC) system This model was applied to a set of validation compounds, three existing oximes (2-PAM, HI-6, MMB4), the Taylor compound RS-194B (i.e. CV9-043 at LLNL), and 21 oximes according to the present disclosure. Validation compounds and existing oximes were obtained commercially. The Taylor compound and additional oximes were synthesized as described above.

Figure 6:
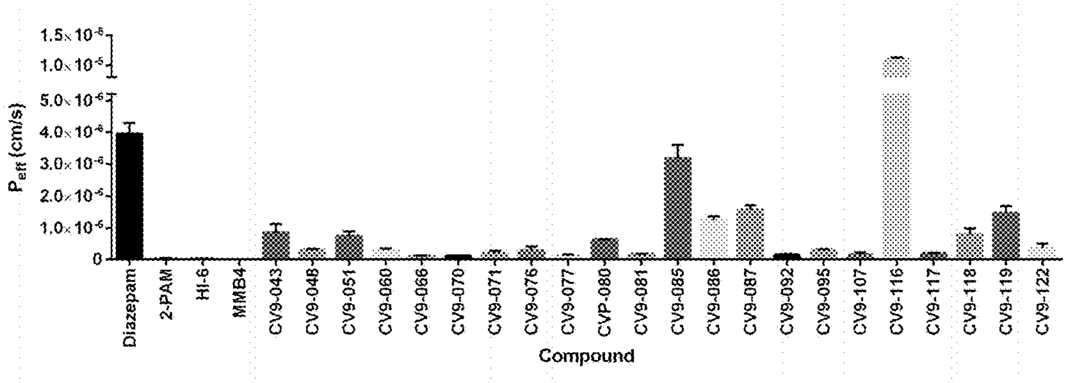
FIG. 6 shows a chart illustrating the effective PAMPA permeability ($P_{eff}$) of tested oximes. Compounds tested are shown along the x axis, and measured effective permeability values as measured in the PAMPA experimental model (centimeters per second) are shown along the y axis. Higher effective permeability values indicate increased permeability in the model. Diazepam is shown as a permeable positive control.
Figure 7:
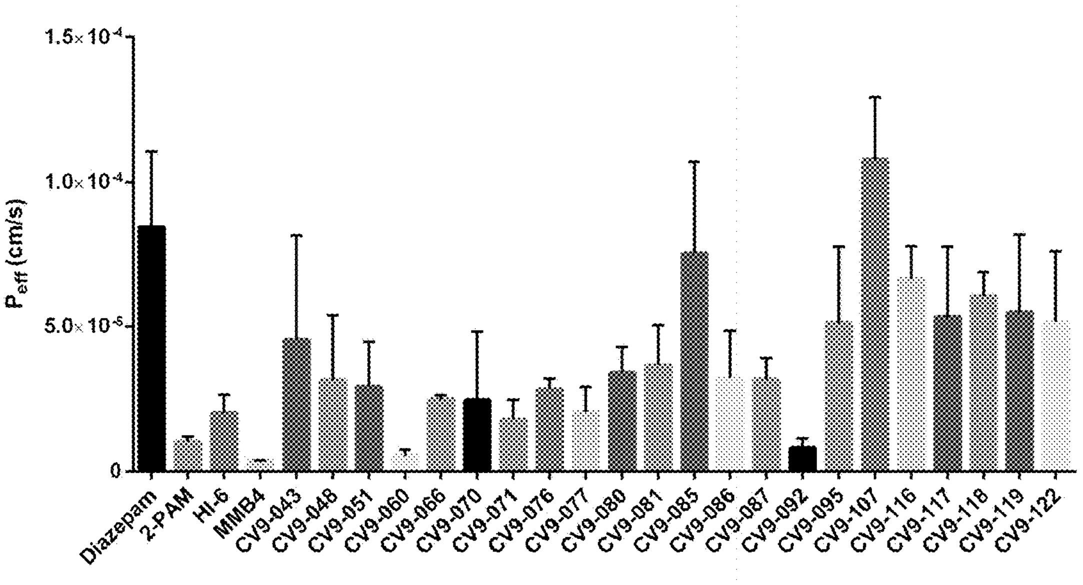
FIG. 7 shows a chart illustrating the permeability of oximes as indicated by brain endothelial cell assay. Compounds tested are shown along the x axis, and measured effective endothelial permeability values (centimeters per second) as measured in the HCMEC experimental model (centimeters per second) are shown along the y axis. Higher effective permeability values indicate increased permeability in the model. Diazepam is shown as a permeable positive control.

The results are shown in FIG. 6. Diazepam is shown as a positive control for permeability. All novel compounds exhibited permeability exceeding standard oximes. Of particular note is compound CV9-116, which demonstrated permeability exceeding Diazepam (FIG. 6). The PAMPA plates used are composed of 96-well filter plates with 0.45 μm pores. The filters are pre-coated by the manufacturer with a lipid/oil/lipid tri-layer artificial membrane (Chen et al. Pharmaceutical Res, 2008, 25:7, 1511-1520).

Example 20: HCMEC/D3 Brain Endothelial Cell Model

The brain endothelial cell assay measures ability of compounds to cross a 2D brain microvascular layer. The assay is composed of two liquid-filled chambers separated by a semi-permeable membrane. Cells are propagated in endothelial cell growth media. The assay is performed in Hank's Balanced Salt Solution (HBSS).

The semi-permeable membrane is made of a polycarbonate membrane with pores of size 0.4 μM at a density of $1\times10^8$ pores/$cm^2$ on which human cerebral microvascular endothelial cells (HCMECs) are grown in a monolayer. Cells were obtained under Material Transfer Agreement from Cornell University. A compound is added to the liquid in contact with the human cerebral microvascular endothelial cells on the membrane, and ability to pass through the cells is measured at 37° C. for time points ranging from zero to two hours. Compound is measured by quantifying the material in solution using the Waters Acquity ultra performance liquid chromatography (UPLC) system.

All oximes noted in Example 19 were also tested in this model. Nearly all oximes of the instant disclosure exhibited permeability superior to the standard oximes, and several were statistically equivalent to other oximes (see e.g. RS-194B).

Example 20: MDR1-MDCK Efflux Model

The MDR1 efflux assay measures whether a drug compound is pumped out of the brain by MDR1 (P-gp).

If a compound is an efflux substrate, it will likely not permeate the brain effectively. The assay is composed of two liquid filled chambers separated by a semi-permeable membrane. The semi-permeable membrane is made of a polycarbonate membrane with pores of size 0.4 μM at a density of $1\times10^8$ pores/$cm^2$. Cells are propagated in supplemented Dulbecco's Modified Eagle Medium (DMEM). When assessing compound permeability, the assay (when testing compounds of interest) is performed in Hank's Balanced Salt Solution (HBSS). The membrane is coated with MDCK cells modified to express MDR1.] Cells were obtained under Material Transfer Agreement from the National Institutes of Health. Permeability of tested compounds is measured in both the apical to basolateral direction and basolateral to apical direction at 37° C. after three hours. Further, permeability is measured in both MDR1-MDCK cells and parent MDCK cells to normalize for permeation via means other than efflux by MDR1. Compound is measured by quantifying the material in solution using the Waters Acquity ultra performance liquid chromatography (UPLC) system. The ratio of permeabilities is calculated as the net flux ratio (NFR) as described in Feng J et al. Drug Metabolism and Disposition, 2008, 36:2, 268-275.

An NFR value greater than one indicates that the compound is a potential efflux substrate, less likely to exhibit high permeability.

Figure 8:
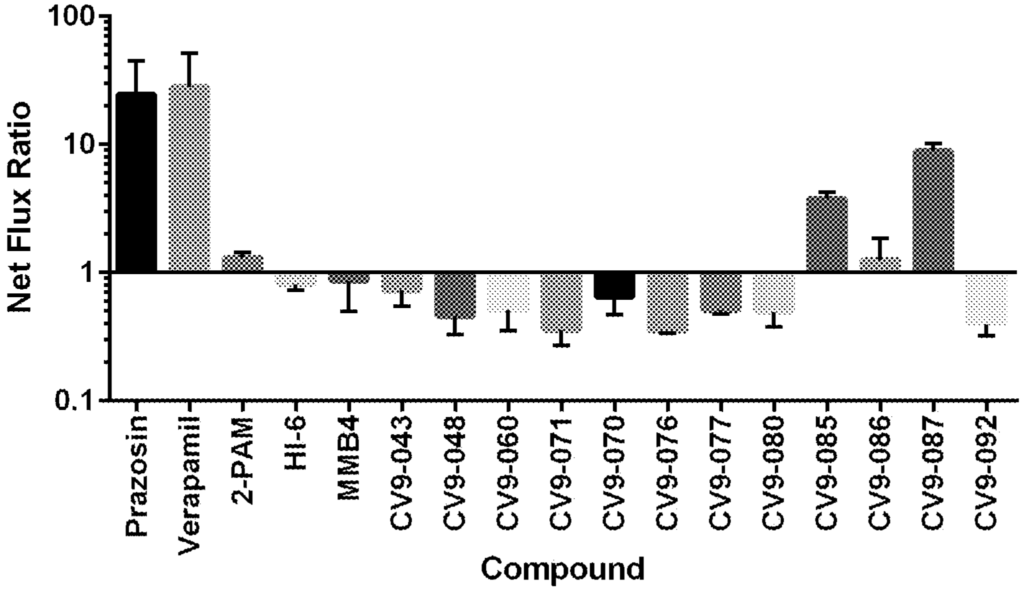
FIG. 8 shows a chart illustrating the net flux ratios of oximes as determined by the MDR1-MDCK assay in which prazosin and verapamil are shown as positive controls for efflux. Compounds tested are shown along the x axis, and measured net flux ratio values as measured in the MDR1-MDCK experimental model are shown along the y axis. A compound exhibiting a net flux ratio greater than one indicates that the compound may be a substrate of the efflux pump MDR1. Prazosin and verapamil are known substrates of MDR1.

FIG. 8 shows NFR of tested compounds. Prazosin and verapamil are shown as positive controls, as these compounds are known MDR1 substrates with NFR>1. Of the synthesized oximes tested, only CV9-085, 086, and 087 have demonstrated NFR>1, indicating possible identity as MDR1 substrates Example 21: AChE Reactivation Ability of compounds to reactivate human AChE was determined using a modified Ellman's assay [Ellman et al. 1961]. The molar ratio of AChE/GB required to achieve ~95% inactivation was determined empirically. Inactivated AChE was incubated with oxime at 100 μM for 15 min. Both acetylthiocholine and a colorimetric indicator (DTNB) were added, and absorbance was continuously measured at 410 nm for 30-60 min. All data were corrected for background auto- and oxime-induced hydrolysis.

Figure 9:
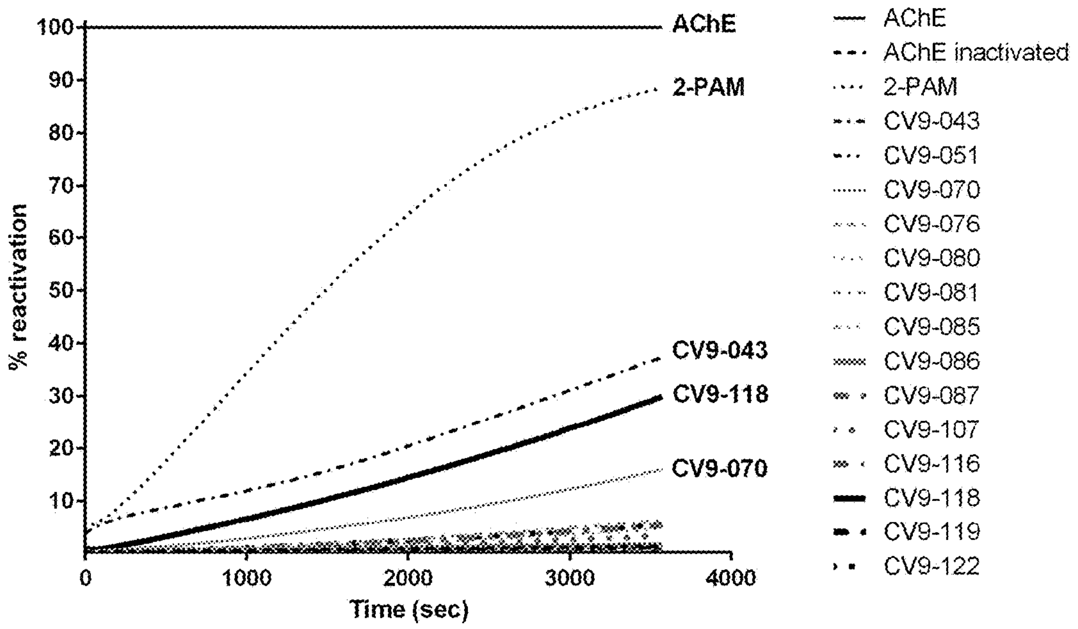
FIG. 9 shows percentage reactivation of human AChE by oximes over time.

FIG. 9 demonstrates the reactivation of acetylcholinesterase by oximes as measured by the modified Ellman's assay. Hydrolysis of the acetylthiocholine substrate and subsequent cleavage of DTNB is indicated by an increase in absorbance at 410 nm. The absorbance results are corrected for possible background hydrolysis. Results are then normalized to uninhibited acetylcholinesterase, to show activity of the oxime-treated acetylcholinesterase as a percentage of uninhibited acetylcholinesterase. An increase in the percent reactivation over time indicates reactivation of acetylcholinesterase by the relevant oxime. Reactivation by the standard existing oxime 2-PAM is shown as a control. A more rapid increase in percent reactivation (steeper upward slope) indicates improved efficacy. All oximes demonstrated slower reactivation relative to 2-PAM.

Example 22: BBB-Permeability Modeling

The free energy profile for a compound passing from bulk water into the center of a lipid bilayer is calculated using umbrella-sampling simulations. The technique is described in Carpenter et al. (Carpenter et al. 2014). As a first approximation, the passive permeability of a compound can be predicted from the relative free energy of the compound as it enters the hydrophobic core of the bilayer (<1 nm from the bilayer center). As a general rule, the more negative the free energy in this region, the more permeable the compound. Likewise, if the free energy is very positive, the compound will likely be impermeable.

Experiments were performed with the oximes of the disclosure (CV9-087, CV9-086) in comparison with another oximes (RS-194B). In particular, umbrella sampling simulations were performed where, a force is imposed on the molecule to maintain its position at a certain point within the membrane. The magnitude of the positional fluctuation of the molecule is correlated to the relative free energy of the molecule at this position the related free energy profiles are reported in FIG. 10. Oximes CV9-087 (black, dotted curve) and CV9-086 (light grey, dashed curve) possess more negative values than the lead, RS-194B and thus exhibit an expected better BBB permeability. Thus, as it can be observed in FIG. 10, the most BBB permeable compound corresponds to the one exhibiting the black, solid curve that provides the most negative value in the calculations.

Figure 10:
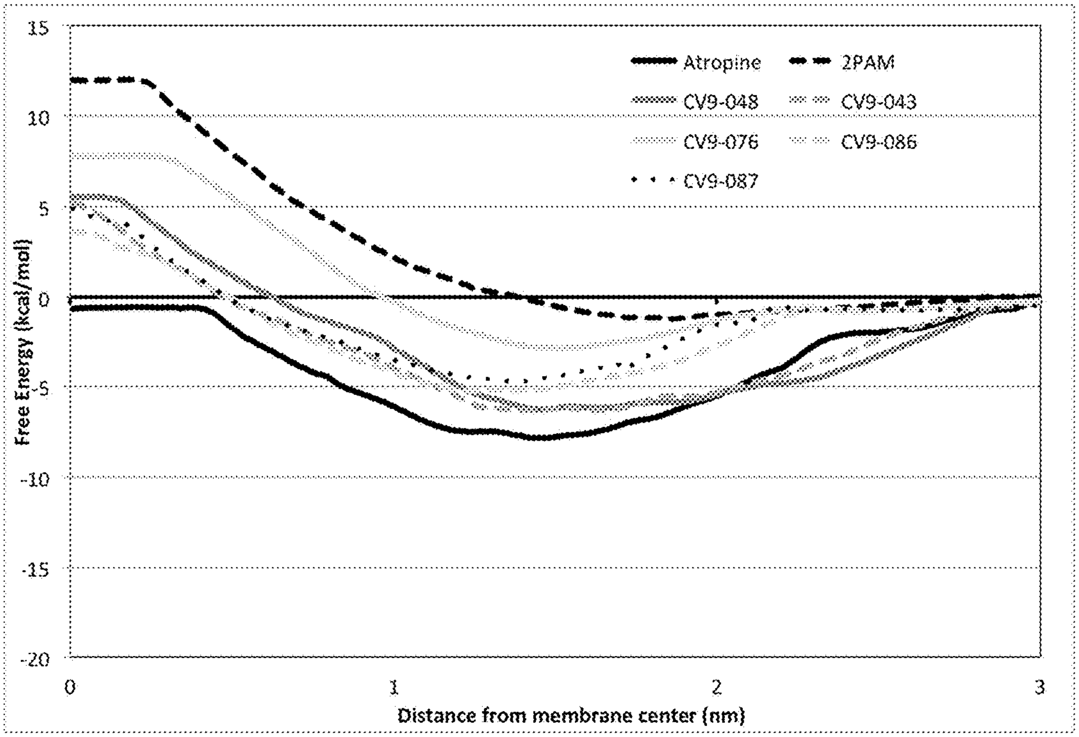
FIG. 10 shows free energy profiles for atropine (black, solid curve) representing a good BBB permeable compound and a panel of neutral oximes.

In this case, among the panel of compounds initially evaluated, Atropine (an outstanding BBB permeable compound) is the best candidate. The full structures of all the compounds in FIG. 10 are given in FIG. 11. Analysis and comparison of the curves show that the known compound RS-194B (i.e. CV9-043) shows moderate to low BBB permeability (gray dashes curve). Whereas compounds disclosed herein, such as CV9-087 (black dots) and CV9-086 (light gray dashes) seem to possess improved BBB permeability. Comparing the data garnered from the various cell-based assays described herein to these simulations provides a computational program that allows prediction of the BBB permeability of a given oxime before it gets synthesized.

The examples set forth above are provided to give those of ordinary skill in the art a complete disclosure and description of how to make and use the embodiments of the materials, compositions, systems and methods of the disclosure, and are not intended to limit the scope of what the inventors regard as their disclosure. Those skilled in the art will recognize how to adapt the features of the exemplified oxime and related uses to additional oximes and/or combinations therefore according to various embodiments and scope of the claims.

All patents and publications mentioned in the specification are indicative of the levels of skill of those skilled in the art to which the disclosure pertains.

The entire disclosure of each document cited (including patents, patent applications, journal articles, abstracts, laboratory manuals, books, or other disclosures) in the Background, Summary, Detailed Description, and Examples is hereby incorporated herein by reference. All references cited in this disclosure are incorporated by reference to the same extent as if each reference had been incorporated by reference in its entirety individually. However, if any inconsistency arises between a cited reference and the present disclosure, the present disclosure takes precedence.

The terms and expressions which have been employed herein are used as terms of description and not of limitation, and there is no intention in the use of such terms and expressions of excluding any equivalents of the features shown and described or portions thereof, but it is recognized that various modifications are possible within the scope of the disclosure claimed. Thus, it should be understood that although the disclosure has been specifically disclosed by embodiments, exemplary embodiments and optional features, modification and variation of the concepts herein disclosed can be resorted to by those skilled in the art, and that such modifications and variations are considered to be within the scope of this disclosure as defined by the appended claims.

It is also to be understood that the terminology used herein is for the purpose of describing particular embodiments only, and is not intended to be limiting. As used in this specification and the appended claims, the singular forms "a," "an," and "the" include plural referents unless the content clearly dictates otherwise. The term "plurality" includes two or more referents unless the content clearly dictates otherwise. Unless defined otherwise, all technical and scientific terms used herein have the same meaning as commonly understood by one of ordinary skill in the art to which the disclosure pertains.

When a Markush group or other grouping is used herein, all individual members of the group and all combinations and possible sub-combinations of the group are intended to be individually included in the disclosure. Every combination of components or materials described or exemplified herein can be used to practice the disclosure, unless otherwise stated. One of ordinary skill in the art will appreciate that methods, device elements, and materials other than those specifically exemplified may be employed in the practice of the disclosure without resort to undue experimentation. All art-known functional equivalents, of any such methods, device elements, and materials are intended to be included in this disclosure. Whenever a range is given in the specification, for example, a temperature range, a frequency range, a time range, or a composition range, all intermediate ranges and all subranges, as well as, all individual values included in the ranges given are intended to be included in the disclosure. Any one or more individual members of a range or group disclosed herein may be excluded from a claim of this disclosure. The disclosure illustratively described herein suitably may be practiced in the absence of any element or elements, limitation or limitations which is not specifically disclosed herein.

A number of embodiments of the disclosure have been described. The specific embodiments provided herein are examples of useful embodiments of the invention and it will be apparent to one skilled in the art that the disclosure can be carried out using a large number of variations of the devices, device components, methods steps set forth in the present description. As will be obvious to one of skill in the art, methods and devices useful for the present methods may include a large number of optional composition and processing elements and steps.

In particular, it will be understood that various modifications may be made without departing from the spirit and scope of the present disclosure. Accordingly, other embodiments are within the scope of the following claims.

REFERENCES

1. Xiaohua Zhang, Horacio Peréz-Sánchez, and Felice C. Lightstone, *Molecular Dynamics Simulations of Ligand Recognition Upon Binding Antithrombin: A MM/GBSA Approach Bioinformatics and Biomedical Engineering* (2015) 9044, 584-593.
2. Ekström F, Hörnberg A, Artursson E, Hammarström L-G, Schneider G, Pang Y-P (2009) Structure of HI-6•Sarin-Acetylcholinesterase Determined by X-Ray Crystallography and
3. Molecular Dynamics Simulation: Reactivator Mechanism and Design. PLoS ONE 4(6): e5957. doi:10.1371/journal.pone.0005957
4. Ellman G L, Courtney K D, Andres V Jr., Feather-Stone RML (1961) *A new and rapid colorimetric determination of acetylcholinesterase activity. Biochem Pharmacol* 7:88-95.
5. Timothy S. Carpenter, Daniel A. Kirshner, Edmond Y. Lau, Sergio E. Wong, Jerome P. Nilmeier, Felice C. Lightstone, A Method to Predict Blood-Brain Barrier Permeability of Drug-Like Compounds Using Molecular Dynamics Simulations, Biophysical Journal, Volume 107, Issue 3, 5 Aug. 2014, Pages 630-641, ISSN 0006-3495.
6. D. D. Haines, S. C. Fox, Acute and Long-Term Impact of Chemical Weapons: Lessons from the Iran-Iraq War, Forensic Sci. Rev. 26 (2014) 97-114.
7. A. T. Tu, Aum Shinrikyo's Chemical and Biological Weapons: More Than Sarin, Forensic Sci. Rev. 26 (2014) 115-120.
8. T. Okumura, T. Hisaoka, A. Yamada, T. Naito, H. Isonuma, S. Okumura, K. Miura, M. Sakurada, H. Maekawa, S. Ishimatsu, N. Takasu, K. Suzuki, The Tokyo subway sarin attack-lessons learned, Toxicol. Appl. Pharmacol. 207 (2005) 471-476.
9 T. Okumura, N. Takasu, S. Ishimatsu, S. Miyanoki, A. Mitsuhashi, K. Kumada, K. Tanaka, S. Hinohara, Report on 640 victims of the Tokyo subway sarin attack, Ann. Emerg. Med. 28 (1996) 129-135.
10. E. Dolgin, Syrian gas attack reinforces need for better anti-sarin drugs, Nat. Med. 19 (2013) 1194-1195.
11. Yang, Y-C.; Baker, J. A.; Ward, J. R. "Decontamination of chemical warfare agents" *Chem. Rev.* 1992, 92, 1729-1743.
12. Singh, B.; Prasad, G. K.; Pandey, K. S.; Danikhel, R. K.; Vijayaraghavan, R. "Decontamination of chemical warfare agents" *Def. Sci. J.* 2010, 60, 428-441.
13. Ajami, D.; Rebek, Jr., J. "Chemical approaches for detection and destruction of nerve agents" *Org. Biomol. Chem.* 2013, 11, 3936-3942.

The invention claimed is:

1. A compound, wherein the compound has Formula (IV)

Formula (IV)

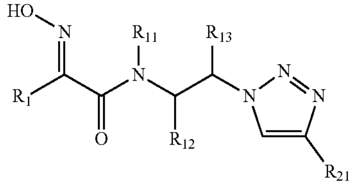

wherein R1=H, CH3, and wherein R11, R12, R13, and R21 are independently H, a linear or branched, alkyl, alkenyl, alkynyl, aryl, arylalkyl or alkylaryl group having equal to or less than 18 carbon atoms and optionally containing additional one to six heteroatoms or one to three substituents.

2. A compound having a Formula (IIId)

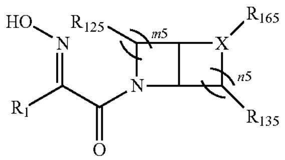

Formula (IIId)

wherein

X is N or C—R102,

R1=H, CH3, and

R102, R125, R135, and R165 are independently H, a linear or branched, alkyl, alkenyl, alkynyl, aryl, arylalkyl or alkylaryl groups having equal to or less than 18 carbon atoms, optionally containing additional one to six heteroatoms or one to three substituents, and wherein m5 and n5 are independent 0-5.

3. A compound of Formula (VI),

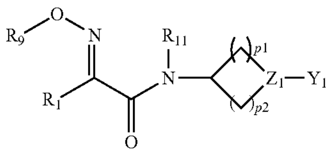

Formula (VI)

wherein R1=H, CH3, and

R11=H, a linear or branched, optionally additional one to six heteroatoms or one to three substituents containing, alkyl, alkenyl, alkynyl, aryl, arylalkyl or alkylaryl carbon atom or a heteroatom having equal to or less than 18 carbon atoms, p1=0 to 5, p2=0 to 5 and p1+p2 is 1 to 5, Z1 is N or C—R20, wherein R20=H, a linear or branched, optionally one to three substituents containing, alkyl, alkenyl, alkynyl, aryl, arylalkyl, alkylaryl, heteroalkyl, heteroalkenyl, heteroalkynyl, heteroaryl, heteroarylalkyl or heteroalkylaryl, each having 12 or less carbon atoms and 0-6 heteroatoms, Y1=H, a linear or branched, optionally one to three substituents containing, alkyl, alkenyl, alkynyl, aryl, arylalkyl, alkylaryl, heteroalkyl, heteroalkenyl, heteroalkynyl, heteroaryl, heteroarylalkyl or heteroalkylaryl, each having 12 or less carbon atoms and 0-6 heteroatoms, and wherein R9 has a Formulas R9a, R9b, R9c, R9d, R9e and R9f, R9a

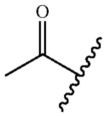

R9b

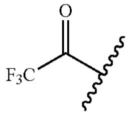

-continued

R9c

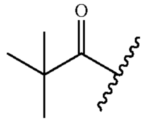

R9d

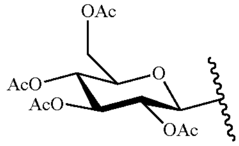

R9e

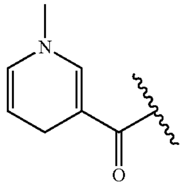

R9f

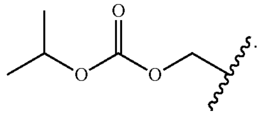

4. The compound of claim 1, wherein the compound has a c log P in the range of 2.0 to 4.5.

5. The compound of claim 1, wherein the compound has a c log P in the range of 0 to 2.

6. The compound of claim 1, wherein the compound has a pKa between 7 to 9.

7. A method to reactivate a nerve agent inhibited acetylcholinesterase in an individual, the method comprising:

administering to the individual an effective amount of at least one compound of claim 1 for a time and under a condition to allow contact between the at least one compound and a nerve agent inhibited acetylcholinesterase in the individual thus resulting in a reactivated acetylcholinesterase.

8. A method of treating and/or preventing a condition of an individual, the condition associated with exposure of the individual to a nerve agent, the method comprising:

administering to the individual a therapeutically effective amount of at least one compound of claim 1 for a time and under a condition to allow contact between the at least one compound and a nervous system of the individual.

9. A method of preventing a condition of an individual, the condition associated with exposure of the individual to a nerve agent, the method comprising:

administering to the individual a therapeutically effective amount of at least one compound of claim 1 capable of inactivating one or more nerve agent, the administering performed for a time and under a condition to allow contact between the at least one compound and a nervous system and/or vascular system of the individual.

10. A method for decontaminating an environment contaminated with at least one nerve agent, the method comprising:

contacting the environment with at least one compound of claim 1 to allow contact of the at least one compound with the at least one nerve agent and inactivation of the at least one nerve agent by the at least one compound.

11. The method of claim 7, wherein the nerve agent comprises the compound of Formula (VIII), (VIII)

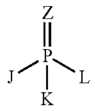

wherein Z is O or S,

J is hydrogen, a C1-C6 alkyl group, a methyl, ethyl, n-propyl, isopropyl, or an amino group NR71R72, wherein R71 and R72 are independently a C1 to C4 alkyl or heteroalkyl group, K is selected from F, Cl, Br, I, CN and SCH2CH2N[CH(CH3)2]2, and L is a C1 to C8 linear or branched alkoxy, a O-cyclohexyl, or a 3,3-dimethylbutan-2-yl group.

12. The method of claim 7, wherein the nerve agent comprises a compound of Formula (X), (X)

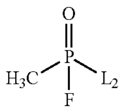

wherein L2 is a C1 to C8 linear or branched alkoxy group.

13. The method of claim 7, wherein the nerve agent comprises a compound of Formula (XI), (XI)

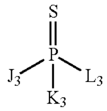

wherein

J3 is a N(CH3)2, N(CH3)(C2H5) or N(CH2CH3)2 group,

K3 is a thiolate group SR75, wherein R75 is a alkyl, alkenyl, alkynyl, aryl, arylalkyl, alkylaryl, heteroalkyl, heteroalkenyl, heteroalkynyl, heteroaryl, heteroarylalkyl or heteroalkylaryl, each having 12 or less carbon atoms and 0-3 heteroatoms, and L3 is selected from the group consisting of O—CH3, O—CH2CH3, O—CH2CH2CH3, O—CH(CH3)2, O-cyclohexyl, and 3,3-dimethylbutan-2-yl group.

14. A pharmaceutical composition to treat a condition associated with exposure of an individual to a nerve agent, the composition comprising at least one compound of claim 1 in a therapeutically effective amount and a pharmaceutically acceptable vehicle.

15. A composition for decomposing a nerve agent, the composition comprising at least one compound of claim 1 in an acceptable vehicle.

16. The composition of claim 15, further comprising at least one metal ion selected from the group consisting of $Cu^{2+}$, $Pt^{2+}$, $Pd^{2+}$, $Zn^{2+}$, $Y^{3+}$, $Sc^{3+}$, $Ce^{3+}$, $La^{3+}$, $Pr^{3+}$, $Nd^{3+}$, $Sm^{3+}$, $Eu^{3+}$, $Gd^{3+}$, $Tb^{3+}$, $Dy^{3+}$, $Ho^{3+}$, $Er^{3+}$, $Tm^{3+}$, and $Yb^{3+}$, or combinations thereof.

17. The compound of claim 1, wherein at least 20% of the compound is in the un-protonated form at pH 7.4.

18. The compound of claim 2, wherein at least 20% of the compound is in the un-protonated form at pH 7.4.

19. The compound of claim 2, wherein the compound has a c log P in the range of 2.0 to 4.5.

20. The compound of claim 2, wherein the compound has a c log P in the range of 0 to 2.

21. The compound of claim 2, wherein the compound has a pKa between 7 to 9.

22. A pharmaceutical composition to treat a condition associated with exposure of an individual to a nerve agent, the composition comprising at least one compound of claim 2 in a therapeutically effective amount and a pharmaceutically acceptable vehicle.

23. A composition for decomposing a nerve agent, the composition comprising at least one compound of claim 2 in an acceptable vehicle.

24. The composition of claim 23, further comprising at least one metal ion selected from the group consisting of $Cu^{2+}$, $Pt^{2+}$, $Pd^{2+}$, $Zn^{2+}$, $Y^{3+}$, $Sc^{3+}$, $Ce^{3+}$, $La^{3+}$, $Pr^{3+}$, $Nd^{3+}$, $Sm^{3+}$, $Eu^{3+}$, $Gd^{3+}$, $Tb^{3+}$, $Dy^{3+}$, $Ho^{3+}$, $Er^{3+}$, $Tm^{3+}$, and $Yb^{3+}$, or combinations thereof.

25. The compound of claim 3, wherein at least 20% of the compound is in the un-protonated form at pH 7.4.

26. The compound of claim 3, wherein the compound has a c log P in the range of 2.0 to 4.5.

27. The compound of claim 3, wherein the compound has a c log P in the range of 0 to 2.

28. The compound of claim 3, wherein the compound has a pKa between 7 to 9.

29. A pharmaceutical composition to treat a condition associated with exposure of an individual to a nerve agent, the composition comprising at least one compound of claim 3 in a therapeutically effective amount and a pharmaceutically acceptable vehicle.

30. A composition for decomposing a nerve agent, the composition comprising at least one compound of claim 3 in an acceptable vehicle.

* * * * *